United States Patent [19]

Van Tyne et al.

[11] 4,170,419
[45] Oct. 9, 1979

[54] OPTICAL WEB INSPECTION SYSTEM

[75] Inventors: Richard G. Van Tyne, Richardson; Weldon A. Sanders, Jr., Seagoville; Richard D. De La Matyr, Richardson; David L. Gates, Plano, all of Tex.

[73] Assignee: Camsco, Inc., Richardson, Tex.

[21] Appl. No.: 771,103

[22] Filed: Feb. 23, 1977

[51] Int. Cl.$^2$ .................. G01N 21/32; G01N 21/48; G01N 21/26
[52] U.S. Cl. .................. 356/431; 356/448; 250/563; 250/572
[58] Field of Search .............. 356/200, 199, 209, 212, 356/238; 250/561, 562, 563, 572

[56] References Cited

U.S. PATENT DOCUMENTS

| | | | |
|---|---|---|---|
| 3,388,261 | 6/1968 | Roberts et al. | 250/224 |
| 3,474,254 | 10/1969 | Piepenbrink et al. | 250/219 |
| 3,518,441 | 6/1970 | Selgin | 250/219 |
| 3,588,513 | 6/1971 | Akamatsu et al. | 356/200 X |
| 3,693,021 | 9/1972 | Lake et al. | 356/200 |
| 3,729,634 | 4/1973 | Niels Jensen et al. | 250/204 |
| 3,774,041 | 11/1973 | Kaneko et al. | 356/200 X |
| 3,781,117 | 12/1973 | Laycake et al. | 356/200 |
| 3,824,021 | 7/1974 | Axelrod et al. | 356/200 |
| 3,841,761 | 10/1974 | Selgin | 356/200 |
| 3,873,970 | 3/1975 | McMahon et al. | 340/146.3 E |
| 3,890,049 | 6/1975 | Collins et al. | 356/199 |
| 3,900,265 | 8/1975 | Merlen et al. | 356/200 |
| 3,917,414 | 11/1975 | Geis et al. | 356/200 |
| 3,972,624 | 8/1976 | Klein et al. | 356/200 |

*Primary Examiner*—Vincent P. McGraw
*Assistant Examiner*—Rodney B. Bovernick
*Attorney, Agent, or Firm*—Richards, Harris & Medlock

[57] ABSTRACT

The specification discloses an optical web inspection system for detecting imperfections in a web having a longitudinal axis and moving in a plane across an inspection area. Radiation means is disposed above the plane of the web and transverse to the longitudinal axis of the web for directing radiant energy on the web at the inspection area. A plurality of sensors are mounted transverse to the longitudinal axis of the web and above the inspection area for receiving reflected radiation from successive transverse portions of the web passing across the inspection area. The plurality of sensors generate electrical output signals representing the intensity of the reflected radiation from the successive transverse portions of the web. Circuitry for periodically summing the electrical output signals from selected ones of the sensors is provided to generate a summation signal representative of the sum of reflected radiation from selected discrete segments of a plurality of the transverse portions of the web. The system further includes circuitry for comparing at least one of the electrical output signals with the summation signal for determining whether an imperfection exists within the web.

9 Claims, 43 Drawing Figures

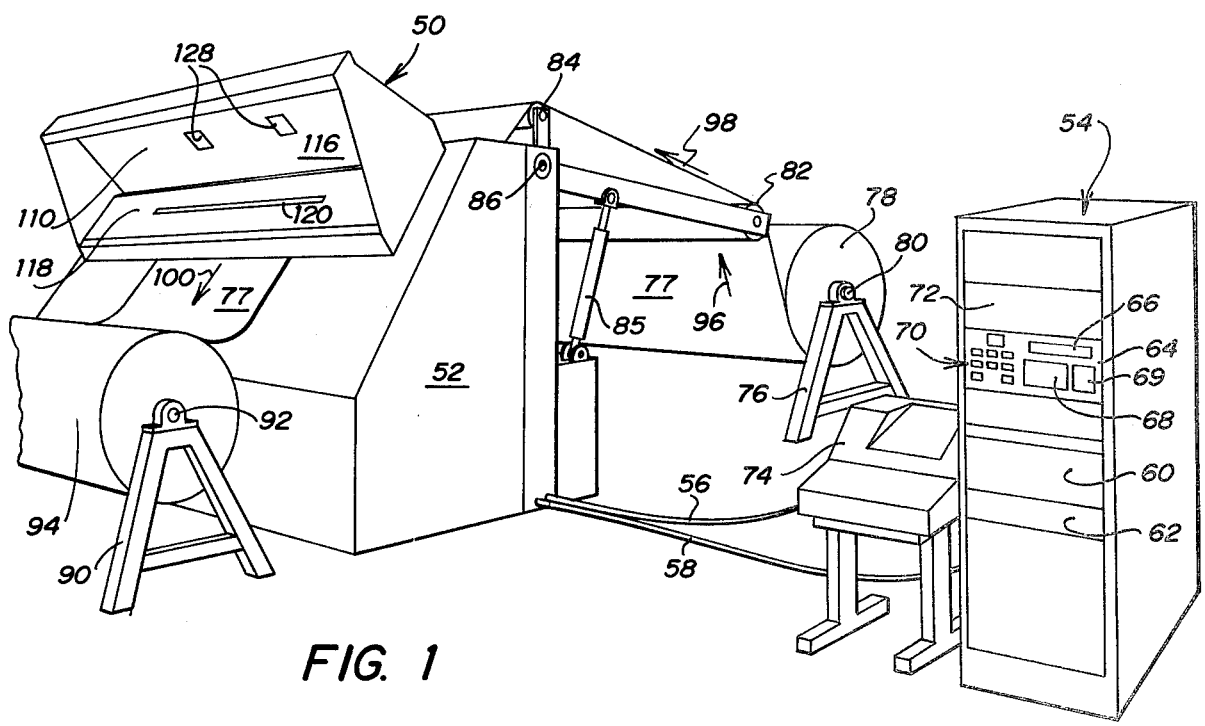
FIG. 1
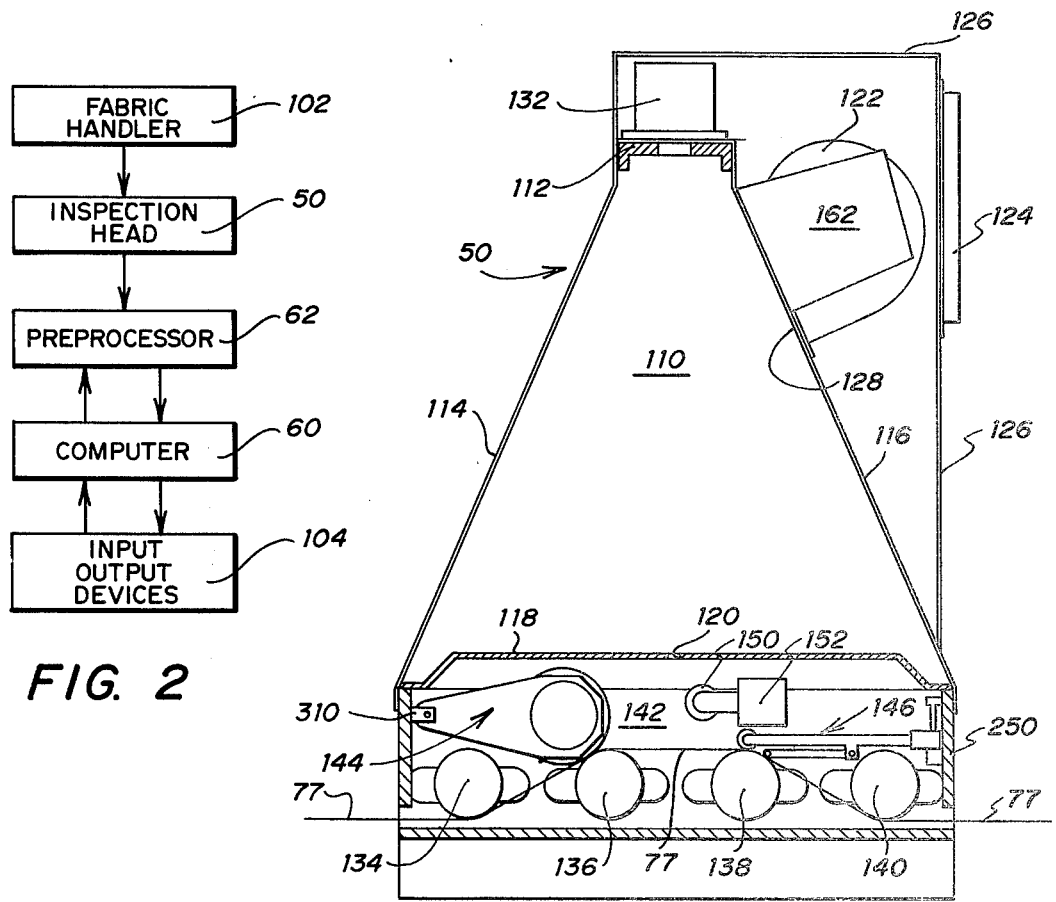
FIG. 2
FIG. 3

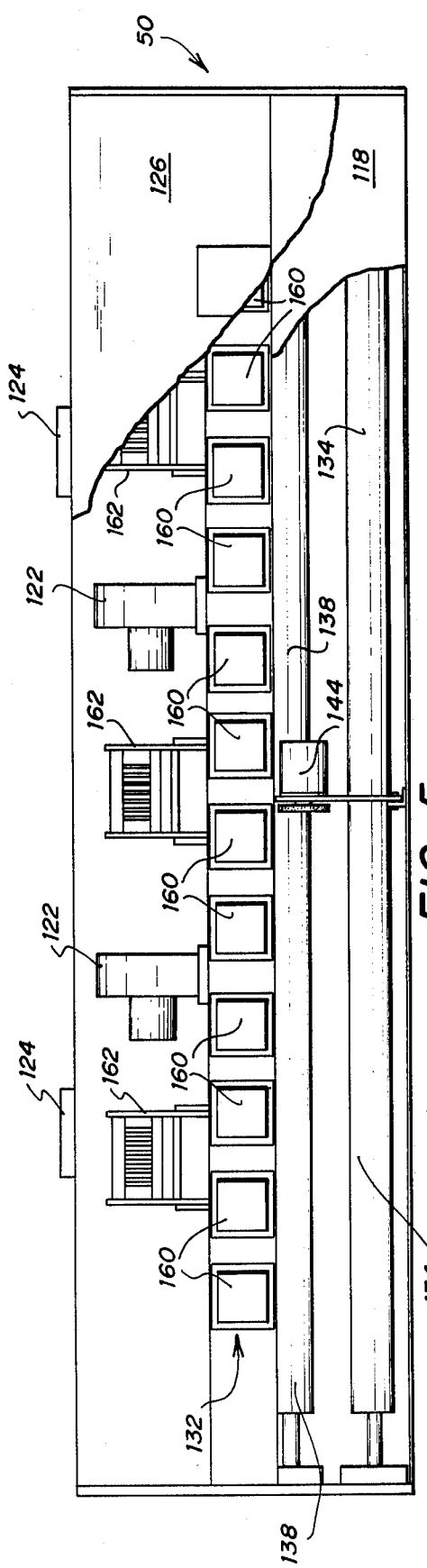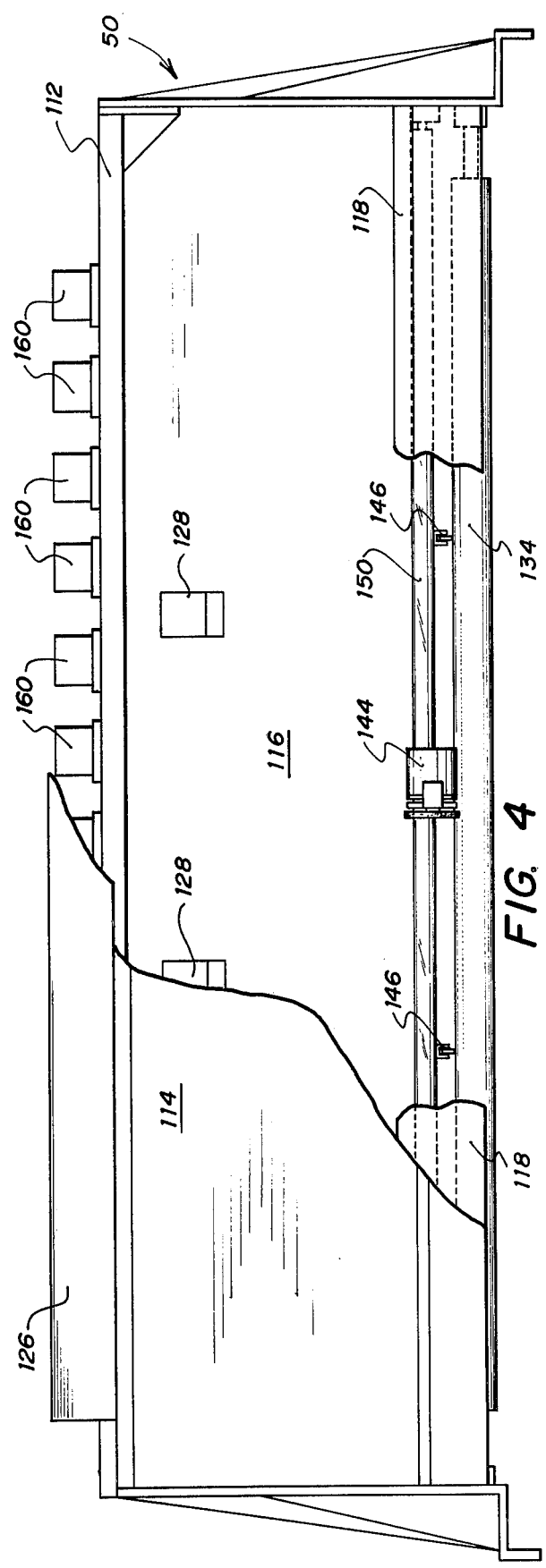

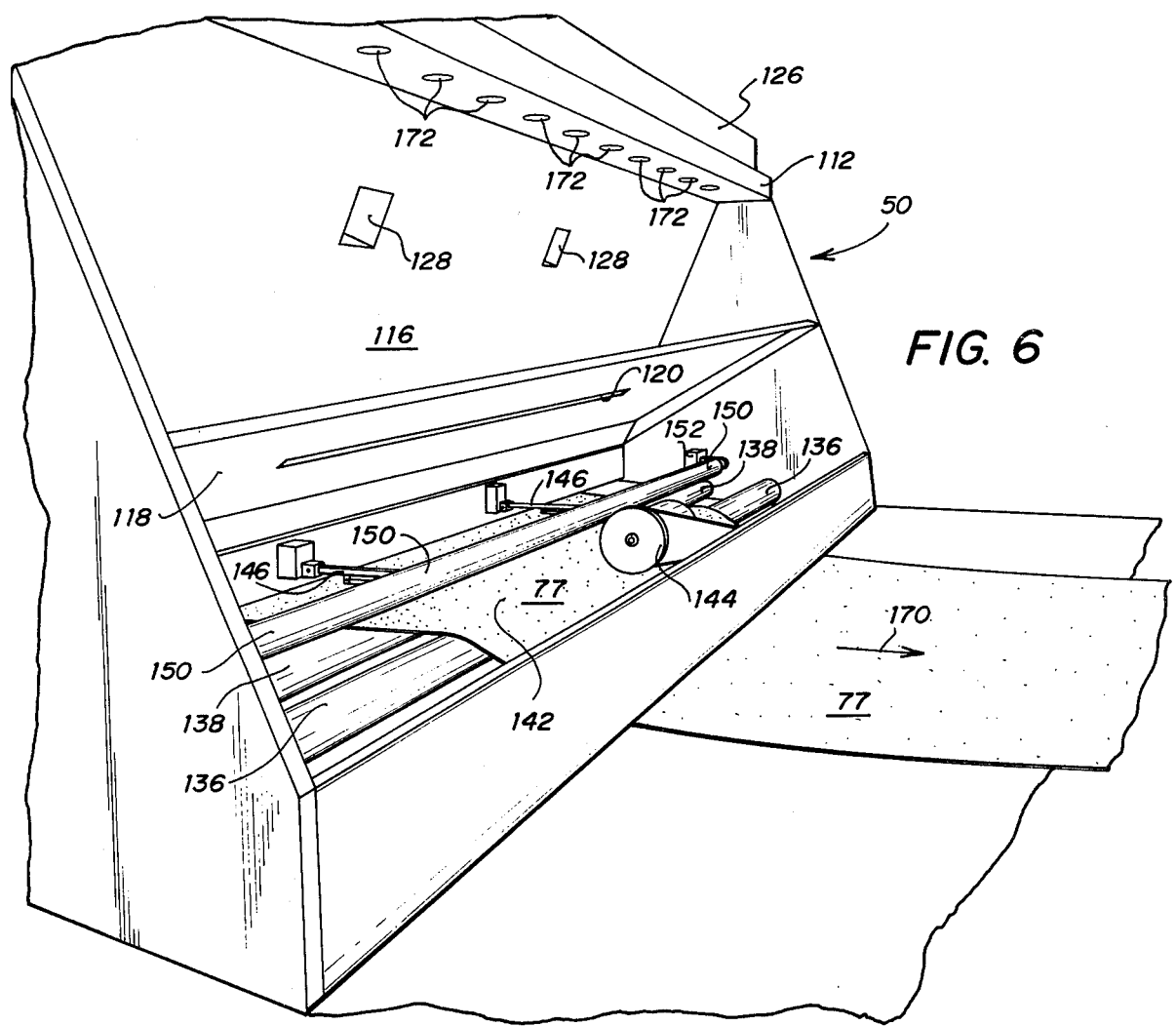

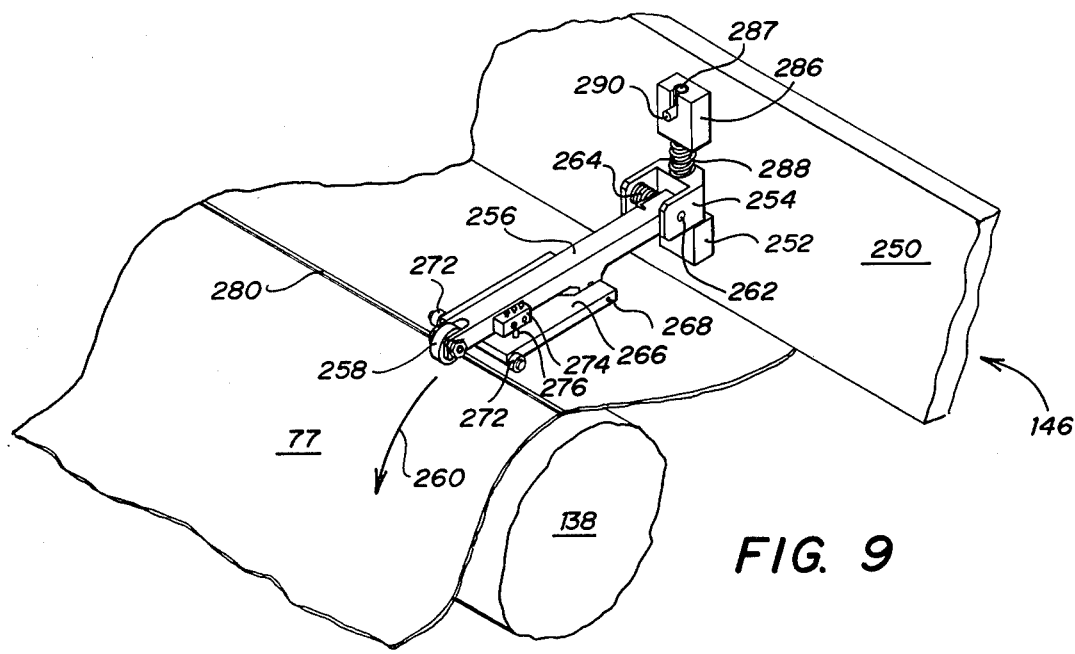
FIG. 9
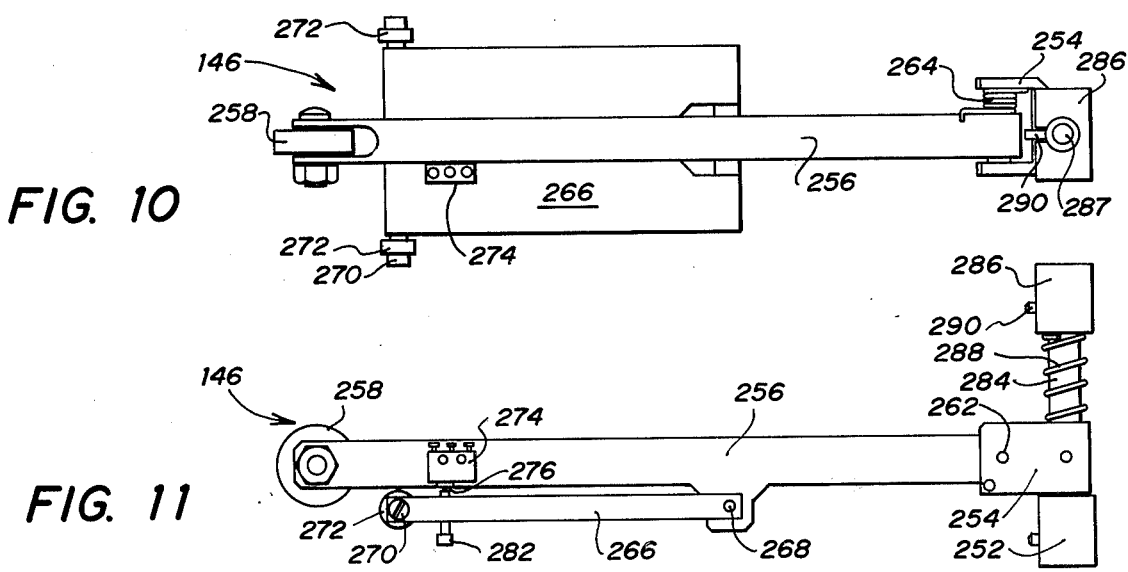
FIG. 10
FIG. 11
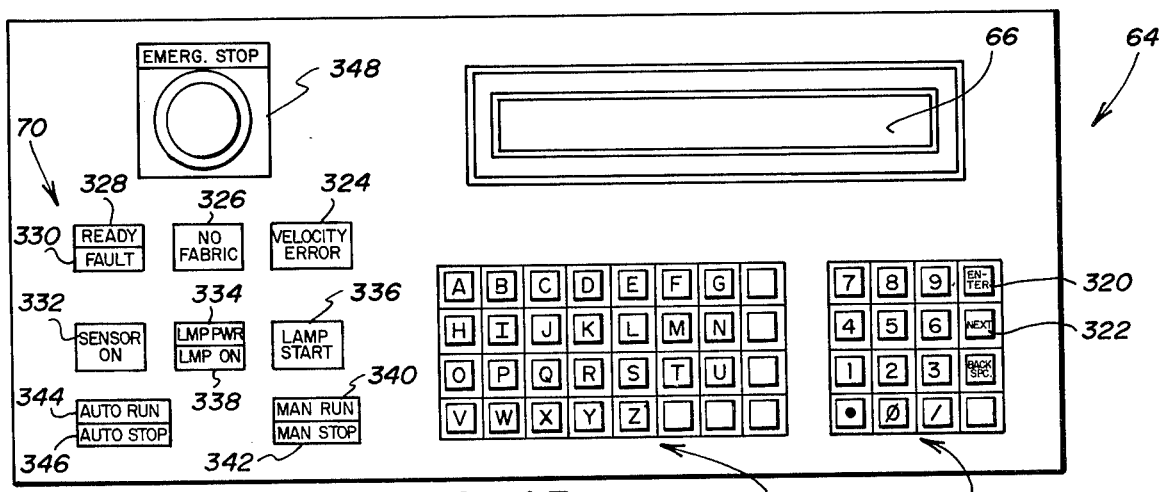
FIG. 15

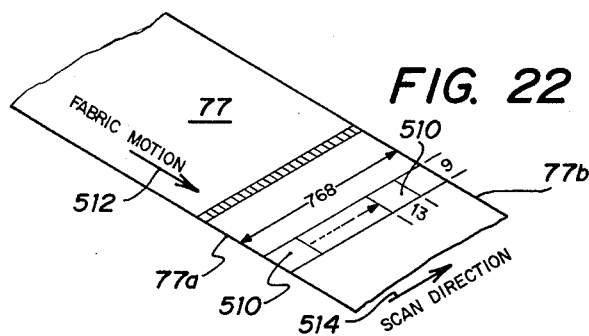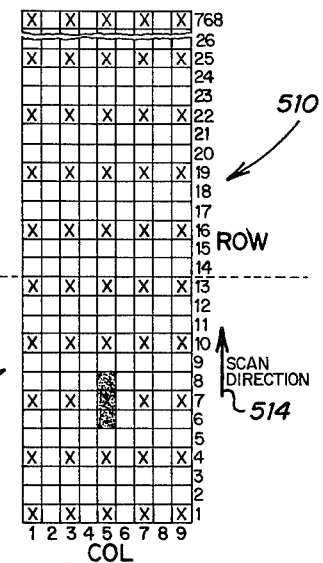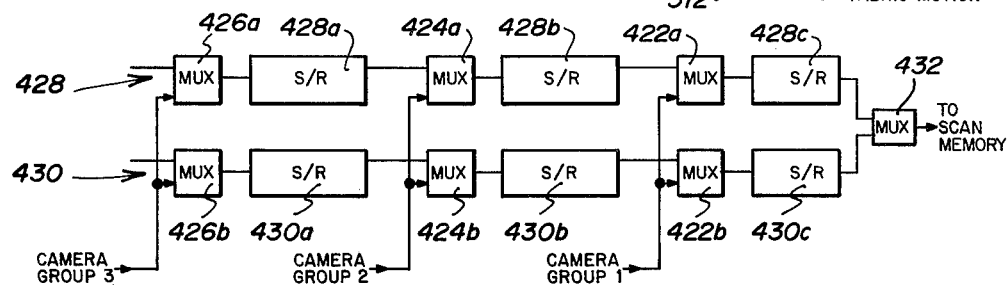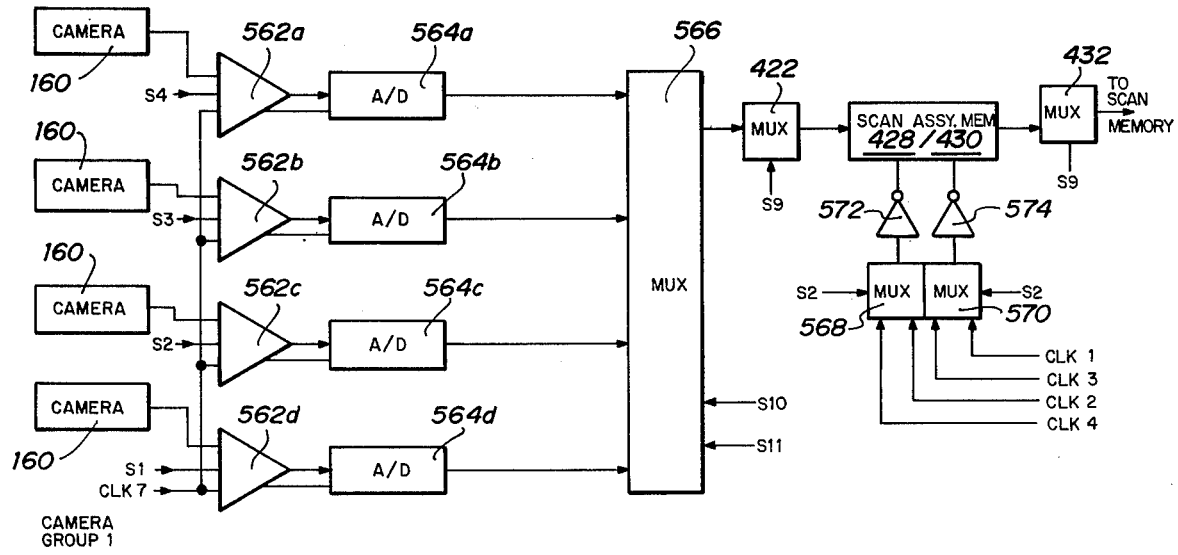

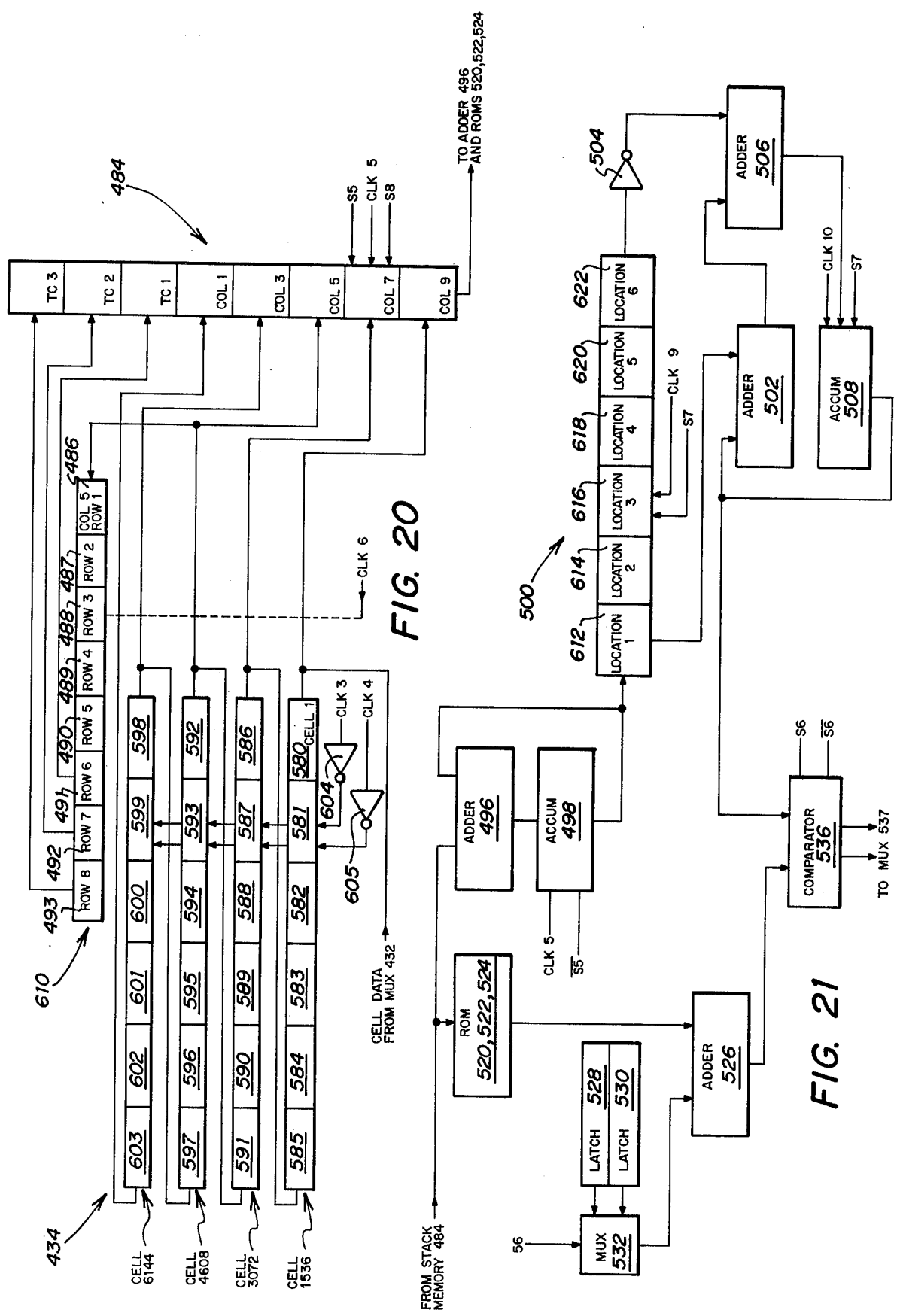

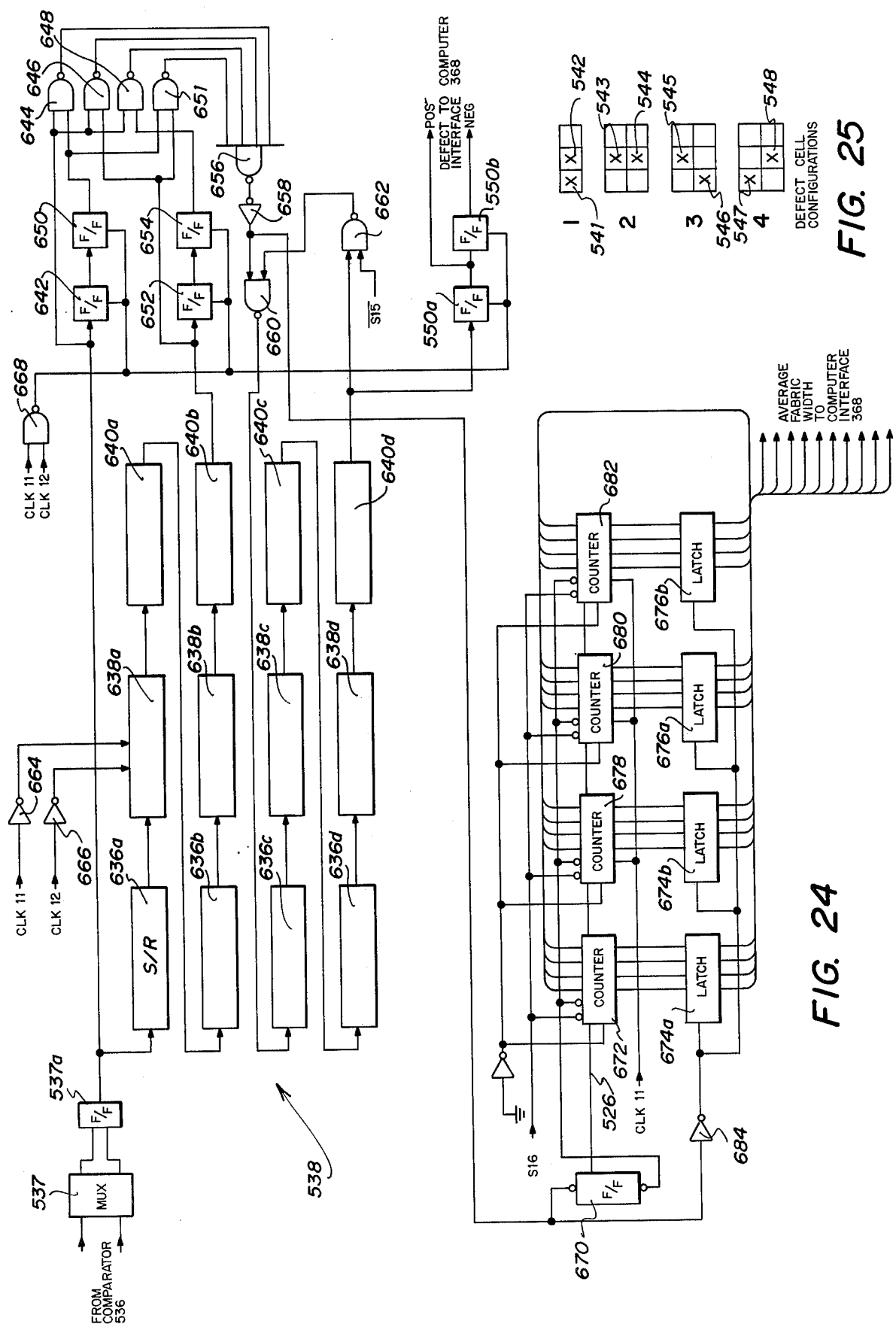

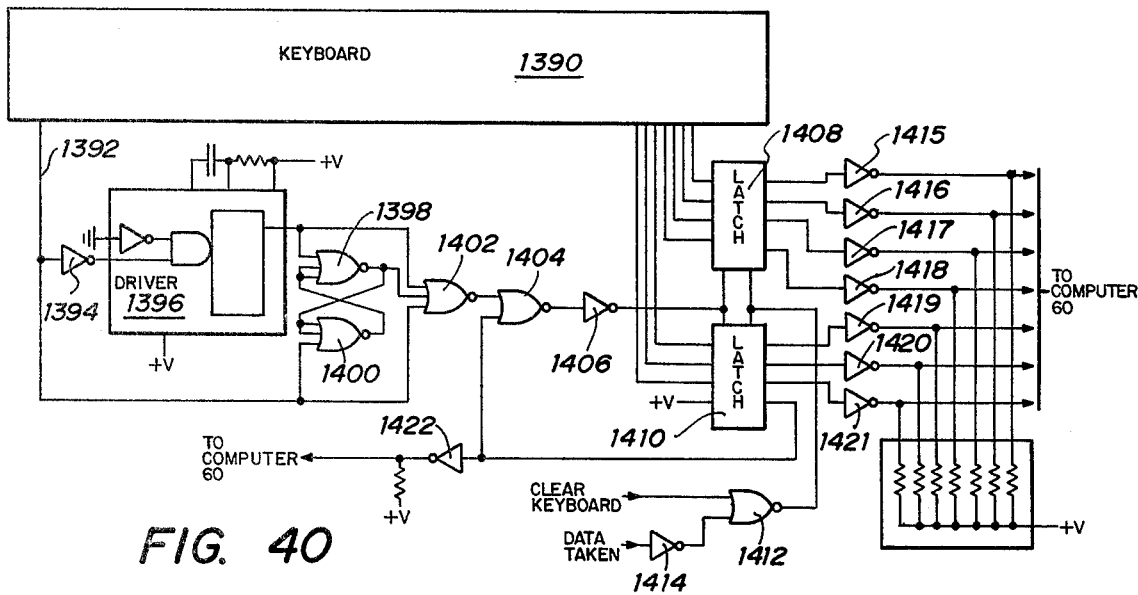
FIG. 40
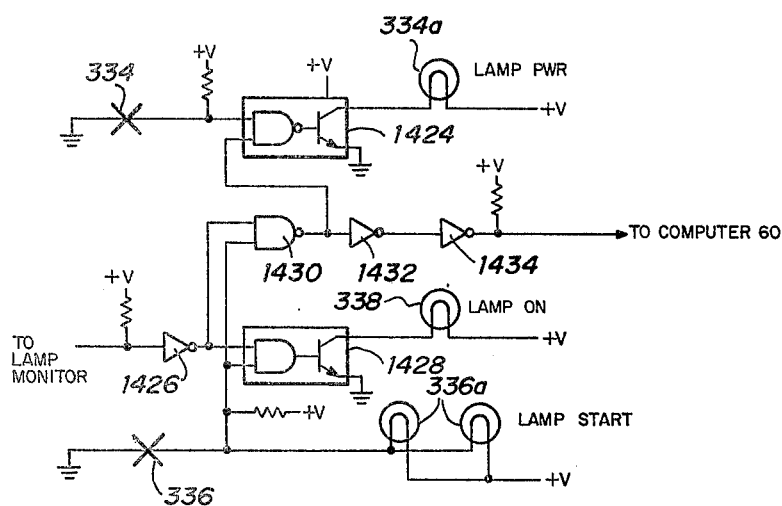
FIG. 41
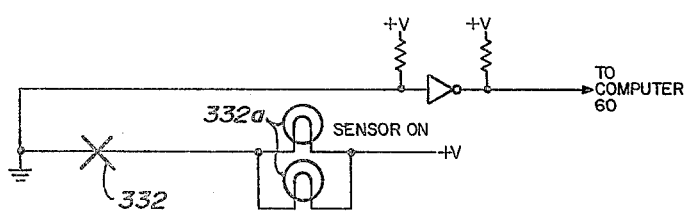

OPTICAL WEB INSPECTION SYSTEM

FIELD OF THE INVENTION

This invention relates to optical inspection systems, and more particularly to an inspection system for detecting and locating imperfections in a moving fabric web.

DESCRIPTION OF THE PRIOR ART

In the textile industry, after a bolt of fabric is manufactured, the fabric is typically inspected for defects or discontinuities in the fabric surface. After a texture fault is located, a determination is made as to whether the fault is considered serious enough, based upon possible customer acceptance or rejection, to warrant removal of the flawed area from the bolt of fabric. The textile industry has cataloged over 100 distinct types of flaws for textiles, and has graded these faults according to their weight in determining acceptability of yard goods by customers. For example, numerous fabric defects have been illustrated and defined in a *Manual of Standard Fabric Defects in the Textile Industry*, (Copyright 1975) compiled by the Graniteville Company of Graniteville, South Carolina. Typical fabric defects include broken picks, mispicks, knots, slubs, filling bands, thick and thin places, coarse threads, and contaminations.

With the increased productivity of textile manufacturing equipment, it has become increasingly difficult for human inspectors to perform their fabric inspection tasks consistently and accurately. The inspection for fabric defects in a moving fabric web is an extremely tedious type of task. Therefore, the fatigue factor of the inspector is quite significant in the ability of the inspector to accurately inspect fabric. An inspector may grade 100 yards of fabric very accurately during the early morning, but as the day progresses and as the inspector becomes tired and fatigued, the same 100 yards of fabric may be graded differently later that same day. An additional limitation in the quality of inspection performed by a human operator is the limitation of the human eye itself. Although the human eye is very accurate when focused on an isolated area, its accuracy is poor peripherally.

Prior systems heretofore developed to optically inspect fabric and a traveling web include those systems described in U.S. Pat. No. 3,474,254 by W. Piepenbrink et al, issued Oct. 21, 1969, U.S. Pat. No. 3,824,021 by N. Axelrod et al, issued July 16, 1974, U.S. Pat. No. 3,841,761 by P. Selgin, issued Oct. 15, 1974 and U.S. Pat. No. 3,917,414 by J. Geis et al, issued Nov. 4, 1975.

Although existing optical inspection systems have eliminated many of the problems associated with human inspection for defects in fabrics, these systems are not efficient for determining the exact location of a defect or discontinuity, nor the size and nature thereof. Generally, existing systems only indicate the existence of a defect, and the longitudinal location thereof on the fabric web. Moreover, such previously developed inspection systems have generally not enabled the differentiation between a fabric defect and the actual fabric surface. Although prior inspection systems have been utilized to inspect steel, paper and wood webs, these systems are inadequate to inspect textile where the signal to noise ratio is lower due to the texture of the fabric.

A need has thus arisen for a fabric inspection system which accurately distinguishes between fabric defects and the actual fabric texture. Such a system must not only detect the existence of surface flaws or discontinuities, but also must chart the location and sizes thereof while disregarding noise inherent in the inspection system. Moreover, a need has arisen for a fabric web inspection system which will uniformly grade a moving fabric web with the accuracy of the human eye from one edge of the web to the other edge of the web. A need further exists for an optical inspection system for detection of flaws in a moving fabric web which will simulate the inspection capabilities of a human operator.

SUMMARY OF THE INVENTION

The present invention is directed to an optical inspection system and method for detecting defects in a moving web, which substantially eliminates of reduces the disadvantages associated with prior art inspection systems. The present optical inspection system electronically inspects the web to simulate inspection by a human operator. Further, the present optical inspection system accurately distinguishes between actual defects and the normal texture of the web surface.

In accordance with the present invention, an optical inspection system for detecting imperfections in a web having a longitudinal axis and moving in a plane across an inspection area includes a radiation means disposed above the plane of the web and transverse to the longitudinal axis of the web. The radiation means directs radiant energy on the web at the inspection area. A plurality of sensor means are mounted transverse to the longitudinal axis of the web and above the inspection area for receiving reflected radiation from successive transverse portions of the web passing across the inspection area. The plurality of sensor means generate electrical output signals representing the intensity of the reflected radiation from the successive transverse portions of the web. The system further includes means for periodically summing the electrical output signals from selected ones of the sensor means to generate a summation signal representative of the sum of reflected radiation from selected discrete segments of a plurality of the transverse portions of the web. The optical inspection system further includes means for comparing at least one of the electrical output signals with the summation signal for determining whether an imperfection exists within the web.

In accordance with another aspect of the invention, an optical inspection system for detecting imperfections in a web having a longitudinal axis and moving in a plane across an inspection area includes a housing disposed above the plane of the web. A radiation means is disposed in the housing above the plane of the web and transverse to the longitudinal axis of the web for directing radiant energy on the web at the inspection area. A plurality of sensor means are positioned within the housing and spaced from the radiation means and transverse to the longitudinal axis of the web for receiving reflected radiation from successive transverse portions of the web passing across the inspection area. Each of the sensor means is responsive to different discrete segments of a transverse portion of the web to generate electrical output signals representing the intensity of the reflected radiation from the plurality of discrete segments. The system further includes means for scanning the electrical output signals from the plurality of sensor means corresponding to successive transverse portions of the web. Circuitry is provided for storing selected ones of the scanned electrical output signals from the successive transverse portions of the web. The system further includes means for periodically summing the stored scanned electrical output signals to generate a summation signal representative of the sum of reflected radiation from selected ones of the discrete segments within the successive transverse portions of the web. Circuitry for extracting at least one of the electrical output signals corresponding to one of the discrete segments from the means for storing electrical output signals is also provided. The system further includes means for comparing the extracted electrical output signal with the summation signal for generating a defect signal indicative of whether an imperfection exists within a discrete segment within one of the successive transverse portions of the web.

In accordance with another aspect of the invention, an optical inspection system for detecting imperfections in a fabric web having a longitudinal axis and moving across an inspection area includes a radiation means disposed above the plane of the web and transverse to the longitudinal axis of the fabric web for directing radiant energy on the fabric web at the inspection area. A first plurality of sensor means is mounted transverse to the longitudinal axis of the fabric web. At least a second plurality of sensor means is mounted contiguously with the first plurality of sensor means and transverse to the longitudinal axis of the fabric web. The first and second plurality of sensor means are disposed above the inspection area and together extend across the width of the fabric web for receiving reflected radiation from successive transverse portions of the fabric web passing across the inspection area. Each of the sensor means receives reflected radiation from a different discrete segment of the transverse portions of the fabric web. The first and second plurality of sensor means further includes means for generating electrical output signals representing the intensity of the reflected radiation from the plurality of discrete segments. Cicuitry is provided for individually scanning the electrical output signals of the first and second plurality of sensor means such that the individual scanning means simultaneously operate in synchronism. The system further includes means for storing the scanned electrical output signals of the first and second plurality of sensor means corresponding to successive transverse portions of the fabric web. The stored electrical output signals are stored serially representing the reflected radiation of the discrete segments extending across the width of the fabric web. Circuitry is provided for periodically summing the stored scanned electrical output signals of transverse portions of the fabric web to generate a summation signal representative of the sum of reflected radiation from selected ones of the discrete segments stored within the means for storing. The system further includes means for extracting at least one of the stored electrical output signals corresponding to one of the discrete segments from the means for storing. The system further includes means for comparing the extracted electrical output signals with the summation signal for determining whether an imperfection exists within the discrete segment corresponding to the extracted electrical output signal.

In accordance with yet another aspect of the invention, a method for detecting imperfections in a web of moving material having a longitudinal axis and moving across an inspection area includes subjecting the web to a source of radiation at the inspection area. Reflected radiation from successive transverse portions of the moving web is detected by a plurality of sensor means. The sensor means generate electrical output signals representing the intensity of the reflected riadation from contiguous segments of the successive transverse portions of the web. The electrical output signals representative of selected discrete segments within the transverse portions of the moving web are periodically summed to generate a summation signal. At least one of the electrical output signals generated by the plurality of sensor means is compared with the summation signal for determining whether an imperfection exists within the moving web.

DESCRIPTION OF THE DRAWINGS

For a more complete understanding of the present invention and for further objects and advantages thereof, reference is now made to the following description taken in conjunction with the accompanying Drawings, in which:

FIG. 1 is a perspective view of the present optical web inspection system;

FIG. 2 is a block diagram of the basic components of the system shown in FIG. 1;

FIG. 3 is an end-sectional view of the web inspection system head assembly of the present invention shown in FIG. 1;

FIG. 4 is a front view, partially broken away, of the web inspection system head assembly shown in FIG. 1;

FIG. 5 is a top plan view, partially broken away, of the web inspection system head assembly shown in FIG. 4;

FIG. 6 is an enlarged perspective view of the web inspection system head assembly with the baffle in a raised position to view the inspection area;

FIG. 7 is a side elevation view, in section, of a camera assembly of the web inspection system head;

FIG. 8 is a sectional view taken generally along sectional lines 8—8 of FIG. 7 of the camera assembly of the web inspection system head;

FIG. 9 is an enlarged perspective view of the seam detector of the present invention shown in FIG. 6;

FIG. 10 is a top plan view of the seam detector shown in FIG. 9;

FIG. 11 is a side elevation view of the seam detector shown in FIG. 9;

FIG. 15 is a front view of the control panel of the web inspection system shown in FIG. 1;

FIG. 19A is a detailed block diagram of the scan assembly memory of the memory circuitry shown in block diagram of FIG. 18;

FIG. 19B is a block diagram of the sensor head circuitry shown in block diagram of FIG. 16;

FIG. 20 is a detailed block diagram of the scan memory circuitry of the memory circuitry shown in block diagram of FIG. 18;

FIG. 21 is a detailed block diagram of the area sum arithmetic function circuitry shown in block diagram of FIG. 18;

FIG. 22 is an illustration of a transverse portion of a web, showing the scan of the web and the motion of the area sum matrix;

FIG. 23 is an illustration of the successive transverse portions of a web and the discrete segments within the transverse portions of the area sum matrix utilized to calculate the area sum;

FIG. 24 is a detailed block diagram of the defect detection, data and width circuitry shown in block diagram of FIG. 18;

FIG. 25 is an illustration of the defect cell configurations resulting in a defect determination;

FIG. 34 is a detailed schematic diagram of the width circuitry shown in block diagram of FIG. 24;

FIG. 40 is a detailed schematic diagram of the control panel keyboard circuitry; and FIG. 41 is a detailed schematic diagram of a portion of the control panel display circuitry.

DESCRIPTION OF THE PREFERRED EMBODIMENT

System Components

Figure 14:
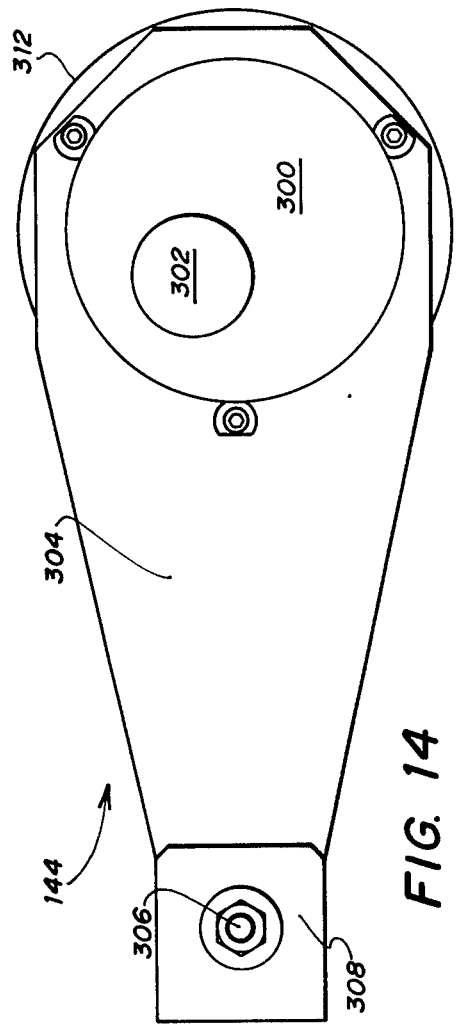
FIG. 14 is a side elevation view of the yardage encoder assembly shown in FIG. 12.

Referring to FIG. 1, the optical web inspection system of the present invention is illustrated. The web inspection system includes an inspection head assembly identified generally by the numeral 50. The inspection head assembly 50 is mounted on an inspection housing 52 for an off-line inspection operation. The inspection head assembly 50 is interconnected to an electronic console unit 54 through interconnecting cables 56 and 58. The electronic console unit 54 includes a digital computer 60 and a preprocessor 62. A control panel 64 is provided to allow an operator to enter data into the computer 60. The control panel 64 includes an alphanumeric display 66, functionalized keyboards 68 and 69 and status lights identified generally by the numeral 70. Storage memory for the comuter 60 is provided by a magnetic disc assembly 72, which is also contained within the electronic console unit 54. A printer 74 is interconnected to the computer 60 to provide an output report of the defects detected during the inspection process.

The fabric handler system for a stand-alone batch processor, as illustrated in FIG. 1, includes an A-frame support 76 positioned to the rear of the fbric inspection housing 52. Support 76 rotatably supports a roll of fabric 78 to be inspected. A motor 80 contained within the A-frame support 76 drives a fabric web 77 from the roll 78 upwardly over a roller 82 to a roller 84 mounted at the top of the inspection housing 52. A cylinder 85 is utilized to support the roller 82 on the inspection housing 52. A second drive motor 86, mounted within the inspection housing 52, ensures that the fabric web 77 moves uniformly across the inspection housing prior to the fabric web 77 being drawn through the inspection head assembly 50. A batcher 90 serves as a take-up device that actually re-rolls the fabric web once inspected. A drive motor 92 is mounted on the batcher 90 to re-roll the fabric on a roll 94. The batcher 90 also provides an automatic edge guide to re-roll the inspected fabric guided to one end of the batcher 90.

It therefore can be seen that the path of the fabric through the inspection head assembly 50 and inspection housing 52 conforms to the direction of arrows 96 from the uninspected roll of fabric 78, arrow 98 towards the top of the inspection table 52 and arrow 100 as the fabric web 77 leaves the inspection head assembly 50 to the batcher 90. If it is desired to have an in-line system, as opposed to off-line or stand alone batch operation, the inspection head assembly 50 can be mounted on a frame located at the end of a production line prior to the batching operation. In this in-line mode of operation, the motivating force for pulling the fabric through the head is provided by the in-line batcher.

FIG. 2 illustrates a block diagram of the interconnection of the basic components of the present system. The fabric handler 102 varies depending upon whether batch or in-line inspection is to be performed. The fabric take-up devices provide the force to drive the fabric web 77 through the inspection head 50. The inspection head 50 includes a plurality of self-scanning photosensitive detectors. These detectors electronically visually view the surface of the fabric to be inspected and convert the fabric surface into electrical information such that the fabric can be analyzed for flaws. The inspection head assembly 50 also includes an encoder assembly to produce electrical signals for measuring yardage and velocity information, the operation of which will subsequently be described. A mechanically actuated device for detecting seams in the fabric web 77 is also included within the inspection head assembly 50, which will also be subsequently described.

Still referring to FIG. 2, the electrical data gathered by the optical detectors located within the inspection head assembly 50 is applied to the preprocessor 62, which accumulates the data and has an input into the computer 60.

An important aspect of the present invention is the generation of a reference value corresponding to reflected radiation of a predetermined area or area matrix surrounding a discrete segment of the fabric web. The preprocessor 62 differentiates a detected defect from the normal background variations found in the fabric surface by comparing the reflected radiation of a discrete segment of the web with the reflected radiation from the area matrix. The preprocessor 62 also performs a data compaction function upon the defect data to reduce the work load of the computer 60. The preprocessor 62 also contains all timing generation circuitry for the inspection system and the logic circuitry for the yardage counter and velocity correction circuitry.

The computer 60 provides the defect grading function according to any of the standard fabric grading rules adopted by the textile industry. The computer 60 receives the defect data from the preprocessor 62 and assigns the grading points to that defect based upon its length, in either the warp or the fill directions. The number of points assigned to the defect is under software control. The computer 60 then generates an output defect report detailing the type and location of a particular defect. The output report is printed by the printer 74.

The input-output devices identified generally by the numeral 104 in FIG. 2 include the printer 74, the operator controls located on the control panel 64 and the disc assembly 72. The operator through the keyboards 68 and 69 can enter general information concerning the roll of fabric, such as style, loom number and bale number. The operator can also start or stop the inspection process through the control panel 64. The disc system 72 provides software initialization at the beginning of an inspection cycle as well as provides overflow capacity for defect reports if the printer 74 is over loaded. The disc system 72 may also be utilized to accumulate information used by another computer to analyze the defect data. The output device, in addition to including a printer, could also include a computer to perform additional analysis on the data or a graphic display terminal to display a visual map of the fabric defects.

A number of digital computers may be utilized in conjunction with the present system. However, in the preferred embodiment of the invention, the computer 60 comprises a general purpose digital computer such as a Hewlett Packard 2105MX series manufactured and sold by Hewlett Packard of Palo Alto, Calif. For further description of the construction and operation of the Model HP 2105MX computer, reference is made to the Hewlett Packard Reference Manual which is incorporated herein by reference. The disc system 72 may comprise, for example, a Sykes Model 7250 system manufactured and sold by the Sykes Corporation.

In the preferred embodiment, the printer 74 comprises a Centronics Model 588 system manufactured and sold by the Centronics Data Computer Corporation of Hudson, New Hampshire. For a further description of the construction and operation of the printer, reference is made to the Centronics Model 588 Reference Manual which is incorporated herein by reference.

The alphanumeric display 66 may comprise any suitable self-scan display. For example, the Burroughs Corporation Gas Discharge Display Model SSD0132-0040 manufactured and sold by the Burroughs Corporation, Plainfield, N.J., may be utilized with the present system. The keyboard 68 may comprise, for example, the keyboard Model PX1-2 manufactured and sold by Micro Switch of Freeport, Ill.

Inspection Head Assembly

Plenum

Referring simultaneously to FIGS. 1 and 3, the inspection head assembly 50 includes a plenum or light box 110. The plenum 110 is defined by a beam 112 at its upper end, a front cover 114 and a rear cover 116. Front cover 114 has been removed from the illustration of the inspection head assembly 50 in FIG. 1. The lower end of the plenum 110 is defined by a light baffle 118, which includes an aperture 120.

The plenum 110 is pressurized by fans 122, which are mounted to the rear cover 116 of the plenum 110. Outside air is drawn into the plenum 110 by the fans 122 through a filter 124 mounted to a housing cover 126. The pressurized air flows from the fans 122 through an aperture 128 into the plenum 110. The pressurization of plenum 110 serves to prevent dirt and lint from entering or accumulating within the inspection head assembly 50. Aperture 120 in the light baffle 118 provides a controlled orifice for the air inside the plenum 110 to escape. In this manner, the plenum 110 can be positively pressurized to a pressure sufficient to keep dirt and lint from entering the plenum 110, while not distorting the fabric web 77 as it moves through the inspection head assembly 50. Also contained within the rear housing cover 126 is an imager assembly generally identified by the numeral 132, which will subsequently be described.

Referring simultaneously to FIGS. 3, 4, 5 and 6, the fabric web 77 is positioned within the inspection head assembly 50 using four fabric rollers 134, 136, 138 and 140. The fabric rollers 134, 136, 138 and 140 are not powered within the inspection head assembly 50 but are free running. Rollers 134, 136, 138 and 140 introduce sufficient friction to the flow of the fabric web 77 to ensure that the fabric web 77 lies flat and is maintained within the object space or inspection area identified by the numeral 142. Fabric rollers 136 and 138 maintain the surface of the fabric web 77 flat and uniform to prevent any wrinkles from occurring as the fabric web 77 moves through the object space 142. Fabric rollers 134 and 140 ensure that the fabric web 77 is maintained tightly against rollers 136 and 138. The fabric web 77 as it is pulled through the inspection head assembly 50 by an on-line or off-line batcher travels under fabric roller 140, above fabric rollers 138 and 136 and finally under fabric roller 134.

Fabric roller 136 also functions as a planar reference surface for a yardage encoder assembly generally identified by the numeral 144. The yardage encoder 144 is an electrical encoder utilized to measure the length of the fabric web 77 as it passes through the inspection head assembly 50. The yardage encoder 144 also serves to generate an output signal that is used to derive the basic timing signals for the inspection system, which correct for velocity changes in the fabric web 77 as it passes through the inspection head assembly 50. The velocity correction signals generated by the yardage encoder 144 provide an input to the preprocessor 62 to correct for velocity changes in the fabric web 77 in the processing of the data produced by the imager assembly 132.

Fabric roller 138 provides a planar reference surface for a mechanical seam detector identified generally by the numeral 146. Although a seam in the fabric web 77 will be detected optically by the imager assembly 132, it is also necessary to detect seams mechanically to distinguish between an actual seam and a defect which extends across the fabric web 77. The operation of the seam detector 146 will be subsequently described in connection with FIGS. 9, 10 and 11.

The illumination source for the imager assembly 132 is provided by a fluorescent lamp 150 positioned below the light baffle 118 and transverse to the direction of the moving fabric web 77. The fluorescent lamp 150 is mounted within the inspection head assembly 50 using a bracket 152. The baffle 118 provides a light shield from the direct rays of the fluorescent lamp 150 from reflecting upwardly to the imager assembly 132. In the preferred embodiment, the fluorescent lamp 150 is 96 inches long to provide a uniform source of illumination within the inspection area 142 to incident on the fabric web 77. Other uniform light sources may be substituted for the fluorescent lamp 150. For example, a tungsten light source employing filters to eliminate the infrared component of the light may be utilized. The fluorescent lamp 150 operates from a direct current source to eliminate the 60 Hz flicker present in fluorescent lamps.

Imager Assembly

Referring to FIGS. 4 and 5, the imager assembly 132 includes an array of cameras or sensors, identified individually by the numeral 160. In the preferred embodiment, twelve such cameras 160 extend transversely across the inspection head assembly 50. In the alternative, a smaller number of cameras can be utilized having an enlarged field of view. Each camera 160 views a 6.4 inch section of the total field of view within the inspection area 142. The total field of view, therefore, is 76.8 inches, which allows for a 4.8 inch over-scan on a typical fabric web having a width of 72 inches.

Each camera 160 includes a photosensitive detector, which in the preferred embodiment, contains 64 elements. Therefore, utilizing a total of twelve cameras, each having a 64 element detector, there are present a total of 768 detector elements in the imager assembly 132. Each of the 768 detector elements thus views a 0.1 inch segment across the 76.8 inch inspection area transversing the fabric web 77. The fabric web 77 is viewed by the imager assembly as a 0.1 inch wide strip transversing the width of the fabric web 77. This strip or transverse portion of the fabric web 77 is segmented by the detector elements into 768 equally-spaced discrete segments. An alternative to the use of twelve cameras 160 each including a 64 element photosensitive detector would be to utilize three cameras 160 each employing a photosensitive detector having 256 elements. A short focal length lens of from 10–13 millimeters is utilized in each of the cameras 160. This focal length in combination with the 0.1 inch resolution per detector element provides a visual acuity similar to that of a human inspector viewing the inspection area from a distance of about 3.5 feet. The system therefore, is capable of detecting flaws in the fabric web 77 which a human operator would detect. The fabric inspection system utilizing these parameters is designed not to identify defects that a human operator would not or that are very difficult for the human operator to see.

Referring to FIG. 5, associated with each group of four cameras 160 is a printed circuit board rack assembly 162. Each rack assembly 162 contains a printed circuit board containing the amplifiers and analog to digital converters associated with each of the cameras 160 in the four camera group. Also included in the circuitry contained by the rack 162 is a 4 to 1 multiplexer which sequences through the four cameras within each group.

As previously discussed, the fans 122 serve to pressurize the plenum 110. Fans 122 also serve to circulate air within the imager assembly 132 to cool the electronic components housed within the rack assemblies 162.

Referring to FIG. 6, the inspection head assembly 50 is illustrated. The front plenum cover 114 has been removed and the light baffle 118 has been raised from its normal position as shown in FIGS. 1 and 3. The direction of the movement of fabric web 77 through the inspection head assembly 50 is indicated by the arrow 170. Cameras 160 are enclosed by the housing cover 126 at the top of the inspection head assembly 50. The cameras 160 are mounted to the beam 112 and receive the reflected radiation from the surface of fabric web 77 in the object space 142 through aperture 120 and lens apertures 172 contained within the beam 112.

Referring simultaneously to FIGS. 7 and 8, a camera 160 is illustrated. Each camera 160 includes a self-scanning photosensitive detector 180, such as a solid state line scanner Model RL-64P manufactured and sold by Reticon Corporation of Mountainview, Calif. Alternatively, charge couples, charge injection, or bucket brigade devices may be utilized as detectors. The detector 180 is glued to a positioning plate 182. Positioning plate 182 is adjustable within a guide plate 183 in the direction indicated by the arrows labeled "Y" by setting screws 184. A second positioning plate 186 adjustable within a guide plate 187 permits the detector 180 to be positioned in the direction of arrows labeled "X" through the adjustment of screws 188. A third positioning plate 190 allows the detector 180 to be rotated in the direction indicated by the arrows labeled "Φ" by adjusting screws 192. Through the adjustment of plates 182, 186 and 190, the detector 180 can be properly positioned within each camera 160.

Reflected light from the fabric web 77 within the inspection area 142 impinges upon the detector window 194 through the camera lens 196. Focus of the camera lens 196 is accomplished by turning the focus ring 198. A number of lenses may be utilized in conjunction with the present camera. However, in the preferred embodiment of the invention, the lens utilized has a focalling of 12.5 millimeters and is lens Model 87022 manufactured and sold by Cosmicar Optical Company of Tokyo, Japan.

The 16 pins 200 of detector 180 are plugged into a socket 202, which is interconnected to an extender cable 204 having plugs 206 and 208 at its ends. Plug 206 mates with socket 202, and plug 208 mates with a socket 210. Socket 210 is mounted to an amplifier printed circuit board 212, which is mounted by spacers 214 to a mounting plate 216. Mounting plate 216 is utilized to mount the camera 160 to the beam 112 (FIG. 6). The entire amplifier card 212, detector 180 and positioning plates 182, 186 and 190 are enclosed by a cover 218, which is positioned in a slot 220 within the mounting plate 216. A rubber O-ring 222 is positioned in the slot 220 to provide a gasket-type seal between the cover 218 and mounting plate 216. The cover 218 is mechanically attached to the mounting plate 216 using brackets 224 and screws 226.

Positioning and alignment of the sensor 180 is accomplished using an alignment fixture. Alignment of each camera is accomplished on an optical bench using reference pin holes which are identical to the pin holes located on the beam 112 (FIG. 6). Each camera 160 can therefore be independently aligned prior to being installed within the inspection head assembly 50 without the field of views of each camera overlapping.

Mechanical Seam Detector

Referring simultaneously to FIGS. 9, 10 and 11, the mechanical seam detector assembly 146 is illustrated. The seam detector 146 is mounted within the inspection head assembly 50 to wall 250 (FIG. 3) using a mounting block 252. A clevis 254 is pivotally mounted to the block 252, and receives a first arm member 256. Mounted to the end of arm 256 is a bearing 258. The bearing 258 is constantly in contact with the fabric web 77 as the fabric web 77 moves across fabric roller 138 in the direction indicated by the arrow 260. Arm 256 is mounted to the clevis 254 using a pin 262 and a torsion spring 264.

A second arm member 266 is pivotally mounted using a pin 268 to arm member 256. Mounted to the end of arm 266 is a rod 270, which includes bearing 272. Bearings 272 are smaller in diameter than the bearing 258. Due to the relative position of arms 256 and 266, bearings 272 contact a portion of the fabric web 77 prior to the contact of the same portion of fabric web 77 with the bearing 258. Bearings 272 are always in contact with the fabric web 77 as the web 77 moves across the fabric roller 138.

A micro switch 274 is mounted on the arm member 256 and has a normally open contact 276. Because arm member 266 is free to move independently of arm member 256, the arms 256 and 266 act as a fabric thickness differentiator. As a fabric seam 280 (FIG. 9) approaches the mechanical seam detector 146, the seam will contact the bearing 272 mounted on arm 266 and cause arm 266 to be pivoted upwardly. This upward motion towards arm member 256 will cause a contact 282 mounted on arm member 266 to engage contact 276 of the micro switch 274, which will then generate an electrical signal indicating that a change in thickness of the fabric web 77 has been detected. This change in thickness is caused by the passage of the fabric seam 280 under bearings 272.

Arm members 256 and 266 measure the relative difference between the thickness of the fabric web 77 as the web 77 contacts the bearing 258 as compared to the thickness of the web 77 where it contacts the bearings 272. The detection of a seam is, therefore, accomplished by measuring the relative differences in the fabric web thickness as a point on the fabric moves across the bearings 272 and 258. This measurement avoids the necessity of making a precise thickness determination and comparisons to that initial measurement.

Mounted through the clevis 254 and mounting block 252 is a shaft 284 on which a block 286 is mounted. Block 286 includes an aperture 287, which permits the shaft 284 to move vertically up and down through the block 286. A compression spring 288 is mounted around shaft 284 between the clevis 254 and the block 286. The rod 284, block 286 and compression spring 288 permit the mechanical seam detector 146 to be rotated to a position parallel to the wall 250 of the inspection head assembly 50 such that the seam detector assembly 146 will be disengaged from the fabric roller 138. This disengagement permits easy threading of the fabric web 77 through the inspection head assembly 50 prior to beginning the inspection process. The positioning process is accomplished by raising arm member 256 such that the clevis 254 contacts the block 286 thereby compressing the spring 288. The arm member 256 is then rotated to a position parallel to wall 250 to cause a pin 290 mounted to the shaft 284 to engage the upper surface of the block 286, thereby maintaining the spring 288 in its compressed state.

Yardage Encoder Assembly

Figure 12:
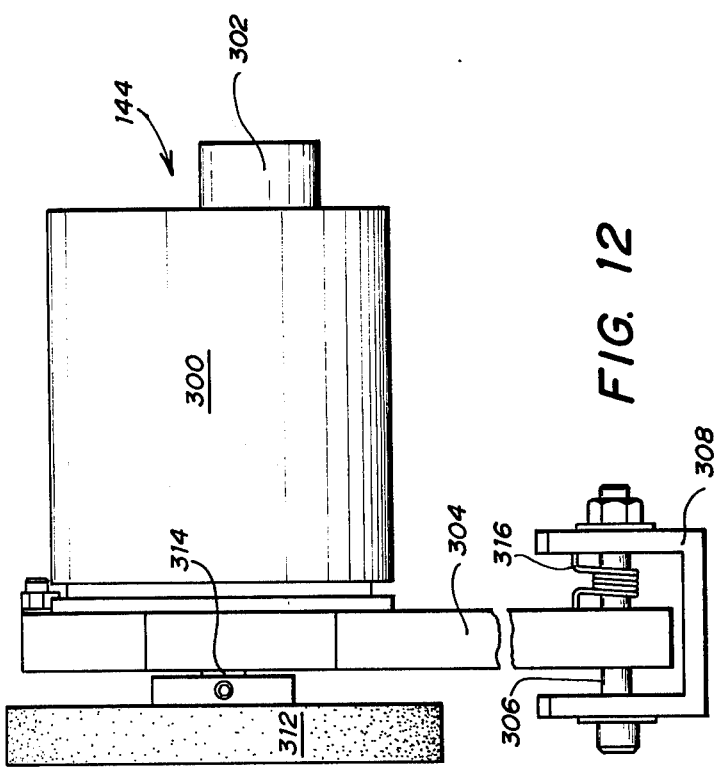
FIG. 12 is a top plan view of the yardage encoder assembly shown in FIG. 6.
Figure 13:
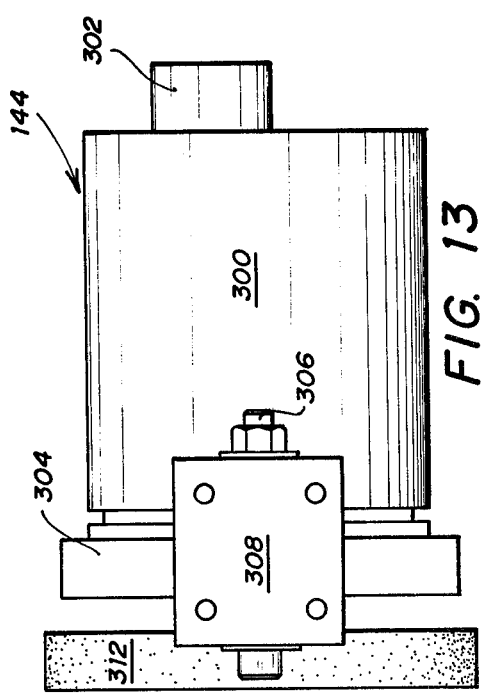
FIG. 13 is an end view of the yardage encoder assembly shown in FIG. 12.

Referring simultaneously to FIGS. 12, 13 and 14, the yardage encoder assembly 144 is illustrated. The encoder assembly 144 includes an optical encoder 300. A number of encoders may be utilized in conjunction with the present system. However, in the preferred embodiment of the invention, the encoder 300 may comprise, for example, a Model 30-HDE-600 encoder manufactured and sold by Renco Corporation of Golet, Calif. Power is supplied to the encoder 300 through a plug 302. An arm 304 is rigidly attached to the encoder 300, and is mounted through a shaft 306 to a mounting bracket 308. Mounting bracket 308 is mounted to a rail 310 (FIG. 3) which extends across the length of the fabric inspection head assembly 50.

An encoder wheel 312 is mounted on an encoder shaft 314. The encoder wheel 312 contacts the fabric web 77 as the fabric web 77 moves across the fabric roller 136 (FIG. 3). The encoder wheel 312 constantly engages the fabric web 77 as it passes over the roller 136 through the use of a torsion spring 316. Torsion spring 316 causes the arm 304 to apply sufficient pressure to the encoder wheel 312 to maintain contact with the fabric web 77. The output of the encoder 300 generates 600 pulses per revolution of the encoder shaft. In the preferred embodiment, the circumference of the encoder wheel 312 is one foot, such that the encoder generates 600 pulses per revolution or 600 pulses per one foot of fabric passing under the encoder wheel 312. The output of the encoder 300 is then applied to the control and timing circuitry of the preprocessor 62 to be subsequently described.

Control Panel

Referring to FIG. 15, the control panel 64 of the fabric inspection system of the present invention is illustrated. The control panel 64 includes a self-scan panel display 66, alpha key set 68 and a numeric key set 69. To enter initialization data through key sets 68 and 69 the operator first depresses the key 320 labeled "ENTER." The display 66 will then request the operator to supply a fabric bale identification number. The operator will then enter through the key set 69 a bale number, which can have a maximum of 10 digits. The operator will then depress key 322 labeled "NEXT," which will cause the display 66 to request the operator to supply a fabric loom number. The loom number can be any number up to 32,000. The operator will then depress key 322, which will cause the display 66 to display a message inquiring as to the width of the fabric to be inspected. The operator then using key set 69 will enter the width of the fabric to be inspected and again depress the key 322. The display 66 will then display a message inquiring as to the style number of the fabric to be inspected. The operator will then enter through the key sets 68 and 69 an alpha/numeric designation to indicate the style. The operator will then depress key 322, and display 66 will indicate that the fabric bale number previously entered is being inspected. The printer 74 (FIG. 1) will begin to print the data entered by the operator, bale number, loom number, width and style on the defect output report. The inspection process will begin after the fabric web 77 has achieved the desired inspection velocity through the inspection head assembly 50.

The diagnostic indicators and switches 70 include a "VELOCITY ERROR" indicator 324, which is illuminated if the velocity of the fabric web 77 is either too high or too low for proper inspection to take place. The "NO FABRIC" indicator 326 is illuminated if there is an absence of fabric within the inspection head assembly 50 during an inspection process. The "READY" indicator 328 is illuminated to indicate that the necessary information has been entered into the computer 60 and that the system is ready to begin the inspection process. A "FAULT" indicator 330 is illuminated to indicate that a problem exists in the system's hardware. A diagnostic error message will then be output from the computer 60 to the printer 74.

A push button switch 322 identified as "SENSOR ON" is depressed to supply power for all of the electronics within the inspection head assembly 50. A push button switch 334 is depressed to supply power to the fluorescent lamp 150 and is labeled "LMP PWR." A "LAMP START" push button switch 336 is depressed for approximately 10 seconds to energize the lamp 150. Upon release of the push button switch 336 the "LPM ON" indicator 338 will be illuminated to indicate to the operator that the lamp 150 is actually on. Since the lamp 150 is totally enclosed within the inspection head assembly 50 the only indication the operator has as to whether the lamp is properly functioning is the indicator 338.

Push button switches labeled "MAN RUN" 340 and "MAN STOP" 342 permit the operator to manually run or stop the inspection process. An indicator labeled "AUTO RUN" 344 will be illuminated when the operator has depressed key 322 after entering the style information through the key set 69. The illumination of indicator 344 will indicate that the system is inspecting fabric. An indicator labeled "AUTO STOP" 346 is illuminated when the system has detected a hardware fault and will automatically discontinue fabric inspection. An emergency stop switch 348 when depressed will disconnect all power from the inspection head assembly 50 and the electronics console 54 (FIG. 1).

As the system is performing an inspection of the fabric web 77, the operator can enter through the control panel key sets 68 and 69 updated fabric information relative to a new piece or style of fabric which will subsequently be inspected. When the seam joining the different fabric webs is detected, the computer 60 will cause the printer 74 to print out this new fabric identification information.

SYSTEM BLOCK DIAGRAMS

Basic Block Diagram

Figure 16:
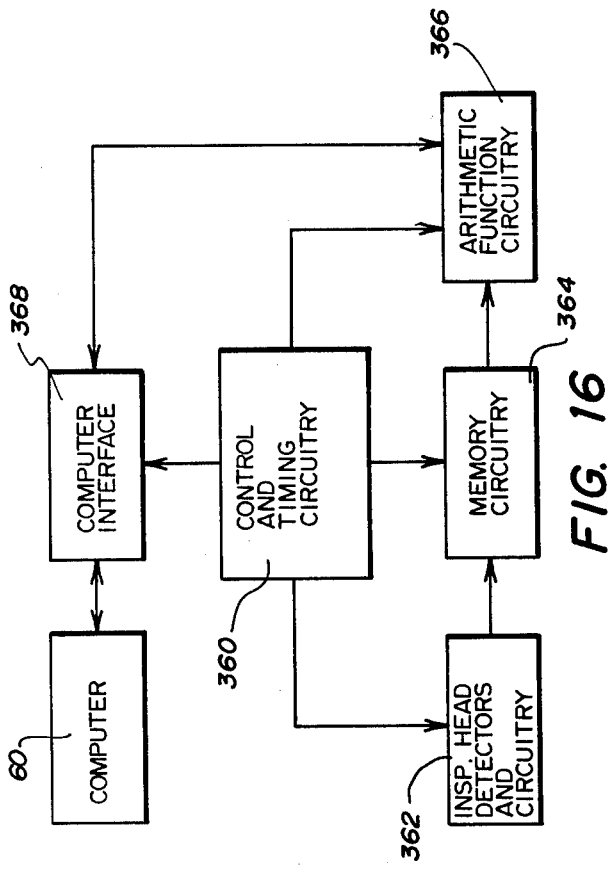
FIG. 16 is a block diagram of the basic electrical circuitry of the present web inspection system.

Referring to FIG. 16, a block diagram of the basic electronic circuitry for the fabric inspection system of the present invention is illustrated. The control and timing circuitry 360 includes a basic oscillator to generate all of the clock and strobe timing signals for the inspection head detectors and their associated circuitry 362, the preprocessor memory circuitry 364, the preprocessor arithmetic function circuitry 366 and the interface circuitry 368 to the computer 60 (FIG. 1). The fabric inspection head assembly 50 consisting of the twelve cameras 160 (FIGS. 4 and 5), for purposes of further discussion these twelve cameras are considered to be associated in three groups. Each camera group, therefore, consists of four cameras. An associated amplifier and analog to digital converter is associated with each of the twelve cameras.

The control and timing circuitry 360 causes the three camera groups to be simultaneously scanned while at the same time successively scanning the four cameras within each group. As previously stated, each camera includes a 64 element detector such that a total of 768 detectors span across the width of the fabric web 77. Each of the 768 detectors view a one-tenth inch square segment of the fabric web during one complete scan of the 768 detectors. For purposes of discussion, the term "cell" or "discrete segment" will represent one of the one-tenth inch square segments viewed by one of the elements of the 64 element camera detector. Assuming that the cameras 160 are arranged and scanned under the control of the control and timing circuitry 360 from left to right, the first four cameras, group 1, located on the left side of the inspection head assembly 50 will scan detectors 1–256, the middle four cameras, group 2, will scan detectors 257–512 and the third group of four cameras located on the right side of the inspection head assembly 50 will scan detectors 513–768. The control and timing circuitry 360 will cause the inspection head detectors and associated circuitry 362 to output data to the memory circuitry 364 in the form of three parallel sets of data, one set from each of the camera groups. These three sets of parallel data comprise the outputs of the cameras of group 1 representing cells 1–256, the output of the cameras of group 2 representing cells 257–512, and the output of the cameras of group 3 representing cells 513–768.

The memory circuitry 364 also receives clock and strobe timing signals from the control and timing circuitry 360. The memory circuitry 364 reconstructs the three sets of parallel input data from the inspection head detectors 362 to a serial representation of the data. This serial reconstruction of the data to represent the output of the three groups of cameras in sequential order from cell 1 to cell 768 is accomplished in a scan assembly memory portion of the memory circuitry 364. The output of the scan assembly memory represents the output data of the cameras 160 in serial form representing a complete scan of the 768 cells across the width of the fabric web 77. Each scan represents the output of the detectors measuring the reflected radiation from a transverse portion of the fabric web 77 measuring one-tenth inch in length across the width of the web 77.

The output of the scan assembly memory is applied to a scan memory portion of the memory circuitry 364, which stores a total of eight scans of data representing the output of the twelve cameras during eight transversals of the fabric web 77. The data from the eight sequential scans of the fabric web 77 is stored in the scan memory portion of memory circuitry 364 with access to that data at 1536 cell intervals. New data is continually shifted into the scan memory, pushing out previously stored data to create a rolling memory, which is continuously changing as new scans of data are added to the memory circuitry 364.

The storage of eight sequential scans of the fabric web 77 create parallel access to five cells corresponding to the same cell location in each of the eight sequential scans. The combination of the same cell location for sequential scans for purposes of discussion will be termed a "row" of cells. The output values of the five cells constituting a row are parallel input into a stack memory of the memory circuitry 364 for input into the arithmetic function circuitry 366. In addition to the row data being tapped from the scan memory, the output data of three contiguous cells located in a single scan are tapped off and input parallel into the stack memory for storage. The three contiguous cells are termed "test" cells. The five cells from a row and the three test cells stored in the stack memory is then output serially to the arithmetic function circuitry 366.

The arithmetic function circuitry 366 includes circuitry to generate the area of matrix sum which represents the sum of the value of the five cells stored in the stack memory plus four additional row sums to constitute the data from 25 different cells. This calculation of an area sum for the value of 25 cells is calculated each time a complete scan of the 768 elements across the fabric web 77 is made by the twelve cameras 160. The sum of the 25 cells creates a moving low resolution field representing the normal background variations of the fabric web 77 over the particular rows and scans which constitute the area from which the 25 cells are selected.

The output values of the three test cells selected from within the area utilized to calculate the area sum are each compared to the area sum. Through this comparison of a single test cell to the area sum of 25 cells, the determination of whether the test cell represents a defect present within the fabric web 77 is made. If the test cell value is greater or less than the area sum value by more than a predetermined amount for the particular fabric being inspected a defect signal is generated and applied to the data compaction circuitry within the arithmetic function circuitry 366.

The defect data is applied to the computer interface 368, which correlates the particular defect with the yard at which the defect occurred along the fabric web 77. The computer interface 368 compensates for any changes in velocity of the fabric web as it moves through the fabric inspection head assembly 50 utilizing the clock and strobe timing signals generated by the control and timing circuitry 360. The location and defect information is then output from the computer interface 368 to the computer 60 for the assignment of grading points to the particular defect and for preparation of the output report analysis.

Control And Timing Functions

Figure 17:
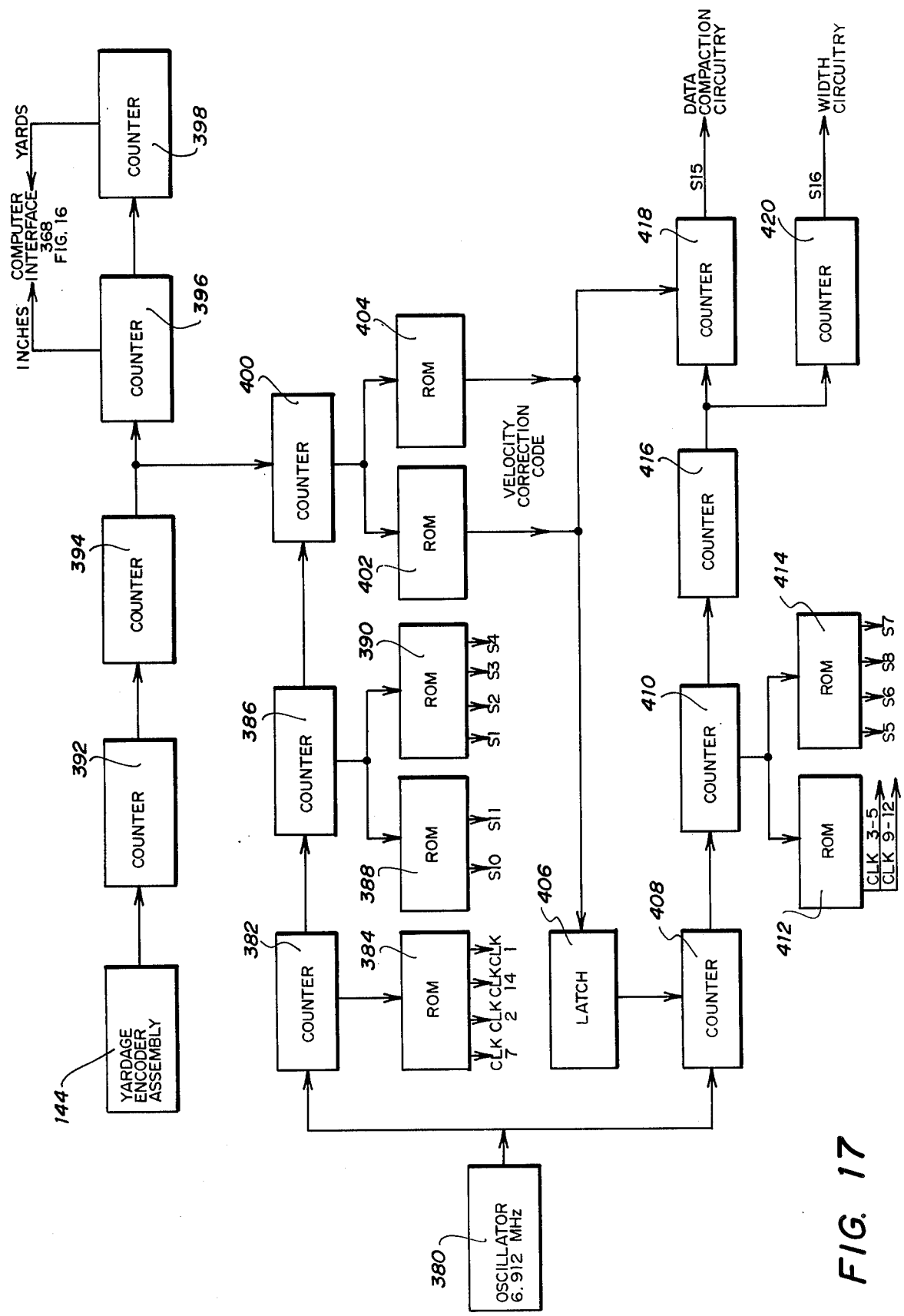
FIG. 17 is a block diagram of the control and timing circuitry shown in block diagram of FIG. 16.

Referring to FIG. 17, a block diagram of the control and timing circuitry 360 (FIG. 16) is illustrated. An oscillator 380 having a frequency of 6.912 MHz supplies an output to a counter 382. Counter 382 performs a divide by 30 function to generate a timing signal for each cell time. The output of counter 382 is applied to a read only memory 384 to generate clock timing signals CLK1, CLK2, CLK7 and CLK14. Clocking signal CLK7 is utilized to clock the cameras 160. Clocking signal CLK14 is utilized to clock the analog to digital converters associated with each camera 160 and the clocking signals CLK1 and CLK2 are utilized to clock various functions within the scan assembly memory of the memory circuitry 364.

The output of counter 382 is also applied to a counter 386. Counter 386 performs a divide by 256 function to generate timing pulses for each of the 256 cells within each of the three camera groups. The output of counter 386 is applied to read only memories 388 and 390. The output of read only memory 388 generates the S10 and S11 timing signals, which are applied to the multiplexer associated with each group of cameras 160. Read only memory 390 generates the S1, S2, S3 and S4 timing signals, which provide the start pulses for each camera 160. The outputs of read only memories 384, 388 and 390 provide all of the timing pulses for the cameras 160 and imager assembly 132 circuitry contained within the fabric inspection head assembly 50. The scan rate of the number of pulses generated or needed to transverse the full 768 cells across the fabric web 77 is maintained constant regardless of changes in the velocity of the fabric web as it moves through the inspection head assembly 50. In the preferred embodiment, the scan rate is approximately 1.1 milliseconds. This rate would equate to approximately 10 scans per linear inch of fabric having a velocity of 150 yards per minute. Compensation for changes in velocity of the fabric web is controlled by the timing pulses supplied to the memory circuitry 364, arithmetic function circuitry 366 and computer interface circuitry 368 (FIG. 16).

To correct for changes in velocity of the fabric web 77 as it moves through the inspection head assembly 50, an adjustment in the number of scans of data supplied to the memory circuitry is made. If the velocity increases above a predetermined amount, certain ones of the scans are accumulated to compensate for lost data. Should the velocity of the fabric web decrease below a specified value, the number of scans per linear inch of fabric will increase and it will be necessary to disregard or skip scans before the data is entered into the memory circuitry 364. Correction for velocity of the fabric web by ignoring some scans or adding scans is utilized as an alternative to changing the exposure time the cameras 160 view a portion of the fabric web. It has been found that to either alter the amount of radiation impinging upon the fabric web or altering the amount of reflected radiation impinging upon the camera lens is difficult to perform in a real time mode. Therefore, in the present invention the exposure time is maintained constant, there is a constant scan interval maintained by the cameras, there is a constant iris opening on the lens of each camera and there is a constant light output from the radiation source.

Compensation for changes in the velocity of the fabric web 77 is performed by the velocity correction circuit, which is contained within the control and timing circuitry 360 (FIG. 16). The velocity correction circuitry includes the yardage encoder assembly 144, which generates an output of 600 pulses per foot for application to a counter 392 (FIG. 17). Counter 392 performs a divide by five function and has its output applied to a counter 394. Counter 394 provides a divide by ten function to generate an output pulse representing one pulse per inch. The one pulse per inch output of counter 394 is applied to a counter 396 which counts the number of inches of the fabric web passing through the inspection head assembly 50. The output of counter 396 is applied to the computer interface 368 (FIG. 16) and to a counter 398. Counter 398 counts the number of yards of fabric which have passed through the fabric inspection head assembly 50 and provides an output to the computer interface 368 indicating yardage information.

The output of counter 394 representing one pulse per inch is applied to a counter 400, which also receives the output of counter 386. The output of counter 386 represents the number of scans, while the output of counter 394 represents pulses per inch. Counter 400 therefore counts actual scans per inch. The output of counter 400 is applied to read only memories 402 and 404. Read only memories 402 and 404 generate a velocity correction code, which is dependent upon the output of counter 400. The velocity correction code is a number having a value from one to seven, in which one indicates no correction is necessary and seven indicates a maximum correction is required. The velocity correction code is then held in a latch 406 and applied to a counter 408.

Applied to counter 408 is the basic oscillator frequency from the oscillator 380. Counter 408 performs a division of the basic oscillator frequency, dividing by the number, one through seven, generated by the read only memories 402 and 404 representing the velocity correction code. The output of counter 408 is applied to a counter 410, which performs a divide by thirty function to generate an output which represents corrected cell time. The output of counter 410 is an output equivalent to that of the counter 382 but corrected by the velocity correction code to compensate for changes in the velocity of the fabric web 77. The output of counter 410 is applied to read only memories 412 and 414, which generate all of the timing pulses for the memory circuitry 364, arithmetic function circuitry 366 and computer interface circuitry 368 (FIG. 16). Read only memory 412 generates the CLK3, 4, 5, 9, 10, 11 and 12 timing signals. Read only memory 414 generates the S5, 6, 7 and 8 timing signals.

The output of counter 410 is also applied to a counter 416. Counter 416 provides a divide by 256 function to provide an output that represents cell time per scan similar to the function of counter 386 but which has been corrected by the velocity correction code. The output of counter 416 is applied to a counter 418 together with the velocity correction code generated by read only memories 402 and 404. The output of counter 418, the S15 timing signal, is applied to the data compaction circuitry, whose function will be subsequently described. The output of counter 416 is also applied to a counter 420, whose output, the S16 timing signal, is applied to the width circuitry.

Memory And Arithmetic Functions

Figure 18:
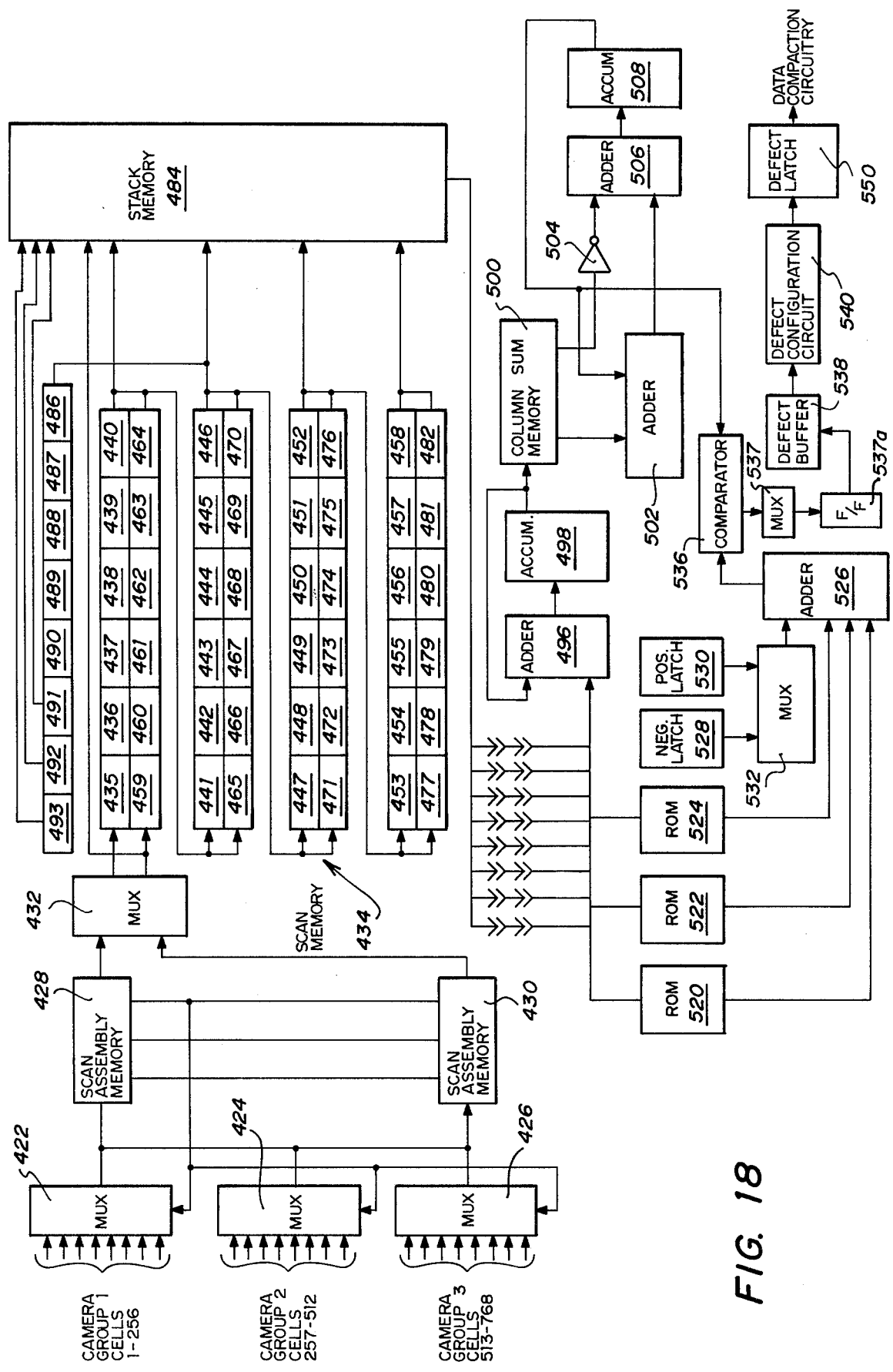
FIG. 18 is a block diagram of the memory and arithmetic function circuitry shown in block diagram of FIG. 16.

Referring to FIG. 18, the memory circuitry 364 and arithmetic function circuitry 366 (FIG. 16) are illustrated in block diagram. The outputs of the four cameras within camera group 1 representing the outputs of the camera detectors corresponding to cells 1-256 are applied to a multiplexer 422. Similarly, the outputs of the four cameras comprising the camera group 2 are applied to a multiplexer 424. The outputs of the four cameras comprising camera group 3 are applied to a multiplexer 426. The output of the inspection head detector circuitry 362 (FIG. 16) is in the form of three parallel inputs of eight bits each to the three multiplexers 422, 424, and 426.

The multiplexers 422, 424 and 426 are 2 to 1 multiplexers that determine whether the scan data is applied to a scan assembly memory 428 or a scan assembly memory 430. The input data to either scan assembly memory 428 or 430 is in the form of three input parallel while the output of the scan assembly memories 428 and 430 is one output serial. The scan assembly memories 428 and 430 assemble the scans from the three parallel inputs representing cells 1-256, 257-512, and 513-768 into a continuous scan of cells 1-768. Because the scan assembly memories 428 and 430 are assembling the three input parallel data to a single serial output, the data must be shifted out of scan assembly memories 428 and 430 at a rate of three times the parallel input rate. The mulitplexers 422, 424, and 426 alternately supply inputs to either scan assembly memory 428 or scan assembly memory 430. When either scan assembly memory 428 or 430 is receiving data, the other is serially unloading data to a multiplexer 432. Scan assembly memories 428 and 430, therefore, alternate functions; as one is receiving data, the other scan assembly memory is transferring a serial output to the scan memory circuitry of the memory circuitry 364 (FIG. 16). The operation of the scan assembly memories 428 and 430 will be further described in conjunction with FIG. 19A.

The output of multiplexer 432 (FIG. 18) is applied to a scan memory identified generally by the numeral 434. The scan memory 434 comprises forty-eight 1024, bit shift registers 435-482. Each of the shift registers 435-482 store 256 words by 4 bits per word. Data from eight sequential scans of the fabric web 77 is stored in the scan memory 434, such that the data from 6144 cells (eight scans times 768 cells per scan) are stored within the scan memory 434. Access to the data stored within scan memory 434 is accessed at 1536 cell intervals. For example, the interval between the cell data stored in shift register 435 and that stored in shift register 441 is 1536 cells. New data is continually shifted into the scan memory 434, which shifts out one scan of data during each scan of the twelve cameras 160.

The same cell within five scans or a row of cells is tapped off from the scan memory 434 to a stack memory 484. The stack memory 484 comprises eight, 8 bit parallel in/serial out shift registers. In addition to tapping off five cells located in the same position within five scans, one cell located within the fifth scan is tapped off from shift register 446 of the scan memory 434 and stored in shift registers 486-493. Shift registers 486-493 are 8 bit serial in/parallel out shift registers and comprise the test cell delay memory. The outputs of shift registers 491, 492 and 493 are applied to three inputs of each of the eight shift registers within stack memory 484. The cell data contained in shift registers 491, 492 and 493 comprises the data from three cells, which represent the test cells to be compared with the area sum or reference value. The reference value is calculated from summing the detector outputs corresponding to twenty-five cells located in a matrix having the center of the matrix as the test cell. The test cell selected and those cells selected for the calculation of the area sum value will be subsequently described in connection with the illustrations of FIGS. 22 and 23, and the block diagram of FIG. 20.

The output of the stack memory 484 is applied to the arithmetic function circuitry 366 (FIG. 16). The five cell values stored in the stack memory 484 representing the same cell location in five scans of data stored in scan memory 434 are applied individually to an adder 496. The output of adder 496 is applied to an accumulator 498. Adder 496 and accumulator 498 are initially cleared to have a content of zero. The output of the accumulator 498 is also applied to the adder 496, which generates a sum of the contents of the accumulator 498 and each of the five cell values applied from stack memory 484. The adder 496 and accumulator 498 operate to generate a sum of the five cells stored in the stack memory 484. These five cells represent a row in the area sum matrix. Briefly, the summation operation is performed as follows:

Step 1. Adder 496 and accumulator 498 are cleared.

Step 2. Cell value 1 is shifted to adder 496 and summed with the contents of accumulator 498, zero, and shifted into accumulator 498.

Step 3. Cell value 2 is shifted into adder 496 and summed with the contents of accumulator 498 (cell 1) and the summation value of cell 1 plus cell 2 is shifted into the accumulator 498.

Step 4. Cell value 3 is shifted into adder 496 and summed with the contents of accumulator 498 (cell 1 plus cell 2) and the resultant sum is shifted to accumulator 498, which now contains the summation of cells 1, 2 and 3.

Step 5. Cell value 4 is shifted into adder 496, and summed with the contents of accumulator 498 and shifted into accumulator 498. Accumulator 498 now contains the sum of cells 1, 2, 3 and 4.

Step 6. Cell value 5 is shifted into adder 496 and summed with the contents of accumulator 498. This resultant sum is shifted to accumulator 498, which now contains the sum of cells 1, 2, 3, 4 and 5, which were previously stored in stack memory 484.

Having totalled the value of a row of five cells, the output of accumulator 498 is applied to a column sum memory circuitry 500, which stores the value of accumulator 498. Column sum memory circuitry 500 includes eleven, 8 bit serial in/parallel out shift registers.

Since the contents of the scan memory 434 is continuously changing with each scan of the 768 cells across the fabric web 77, the five values of the cells tapped off from the scan memory 434 and stored in stack memory 484 also continuously change. The summation operation formed by the adder 496 and accumulator 498 is performed six times to accumulate within the column sum memory circuitry 500 six individual sums. Each of these six individual sums represent the sum of a row of cells outputted from stack memory 484.

The output of the column sum memory 500 is applied to an adder 502 and is applied through an inverter 504 to an adder 506. The output of adder 506 is applied to an accumulator 508, whose output is applied to adder 502. The function of adders 502 and 506, together with accumulator 508, is to create a sum of five of the row sum values stored within the column sum memory 500, which represents a sum of 25 cells. Since the contents of the column sum memory 500 is continuously changing, after each scan the oldest value stored within the memory 500 is subtracted through the inverter 504 by adder 506. The matrix sum of 25 cells is therefore continuously changing as new data is inputted into the column sum memory 500. The effect of this change in the cells which make up the 25 cells within the area sum matrix is illustrated in FIG. 22. The apparent motion of the area sum matrix is to progress from one edge of the fabric web 77 to the opposite edge of the fabric web.

Referring to FIG. 22, the area sum matrix is illustrated and identified by the numeral 510. In the preferred embodiment, the dimensions of the area sum matrix 510 is thirteen cells or rows long and nine cells wide. The total number of cells, 768, is also illustrated in FIG. 22 as transversing across the fabric web 77. The direction of the fabric web motion is indicated by the arrow 512, and the direction of the scan of the twelve cameras 160 is indicated by the arrow 514.

Referring to FIG. 18, the three test cell values stored in the stack memory 484 are applied individually to read only memories (ROMs) 520, 522 and 524. Read only memories 520, 522 and 524 are programmable ROMs and function to multiply by 25 each of the test cell values. The test cell value can then be compared to the value of the area sum matrix to determine whether the test cell value is either greater or less than the value of the area sum matrix for the determination of whether a defect exists in the test cell. The read only memories 520, 522 and 524 each has an address location which is a binary value equivalent to 25 times the address to generate a value which is 25 times the test cell value applied to the read only memory. This output value is then applied to an adder 526. Adder 526 also receives a predetermined value supplied by the computer 60 through the computer interface 368 (FIG. 16) to latches 528 and 530 through a multiplexer 532. This predetermined value supplied by the computer software is referred to as "offset" and is dependent upon the style of the fabric being inspected. The library of the computer 60 stores both a positive value and a negative value for each type of value to be inspected. The purpose of the offset value is to in effect reduce the sensitivity of the detectors within the cameras 160 to ensure that the value of the test cell is not merely noise when compared with the value of the area sum matrix.

The adder 526 performs an addition function to add the output value from the read only memories 520, 522 and 524 to the offset value selected through multiplexer 532. The output of adder 526 is then applied to a comparator 536, which also receives the output of accumulator 508 representing the sum of the 25 cells within the area sum matrix. The output of the comparator 536 indicates that the test cell value is either greater than or less than the value of the area sum matrix. The output of comparator 536 is applied through a multiplexer 537 and a flip-flop 537a to a defect buffer 538. The defect buffer 538 stores the output of comparator 536 for comparisons between each of the three test cell values with the value of the area sum matrix for both positive and negative offset values. The output of the defect buffer 538 is applied to a defect configuration circuit 540. The defect configuration circuit 540 contains logic circuitry to determine whether the defects identified through the comparison made by comparator 536 and stored within the defect buffer 538 conform to one of the four defect configurations illustrated in FIG. 25.

Referring to FIG. 25, the four defect cell configurations are illustrated. Configuration 1 represents defect cells 541 and 542 being contiguous cells from the same scan across the fabric web 77. Configuration 2 represents defect cells 543 and 544 being contiguous defect cells from different scans but of the same row. Defect configuration 3 represents defect cells 545 and 546 being contiguous cells of different scans and different rows. Similarly, defect configuration 4 represents defect cells 547 and 548 being from different scans and different cells. If either of these four defect cells configurations is detected by the defect configuration circuit 540 (FIG. 18), the defect configuration circuit 540 applies an output to a defect latch 550. The defect latch 550 applies an output to the data compaction circuitry to be subsequently described.

Referring to FIG. 19A, a more detailed block diagram of the scan assembly memory circuitry 428 and 430 of FIG. 18 is illustrated. The outputs of the detectors comprising the four cameras of camera group 3 are alternately applied to multiplexer 426a of the scan assembly memory 428 and to multiplexer 426b of the scan assembly memory 430. The output of multiplexer 426a is applied to shift register 428a, which comprises two 4×256 bit shift registers. Similarly, the output of multiplexer 426b is applied to shift register 430a, which comprises two 4×256 bit shift registers. The value of cells 513-768 are stored alternately within shift registers 428a and 430a.

The output of the detectors of the cameras comprising camera group 2 are similarly applied to multiplexers 424a and 424b depending upon whether the scan assembly memory 428 is reading in or shifting out data. Multiplexers 424a and 424b are interconnected to shift registers 428b and 430b, which store the value of cells 257-512. The output of the detectors comprising the four cameras of camera group 1 are similarly applied to multiplexers 422a and 422b. Multiplexers 422a and 422b are interconnected to shift registers 428c and 430c. Shift registers 428c and 430c each comprise two, 4×256 bit shift registers, which store the values of cells 1-256. The outputs of shift registers 428c and 430c are alternately applied through the multiplexer 432 (FIG. 18) to the scan memory.

Referring to FIG. 19B, a more detailed block diagram of the inspection head detectors and circuitry 362 and its interconnection to the memory circuitry 364 (FIG. 16) is illustrated. For purposes of illustration, the camera group 1 has been illustrated in FIG. 19B. The four cameras 160 of camera group 1 are individually interconnected to an associated amplifier 562, which is interconnected to an analog to digital converter 564. Amplifier 562a receives the S4 timing signal, amplifier 562b receives the S3 timing signal, amplifier 562c receives the S2 timing signal and amplifier 562d receives the S1 amplifier signal. The CLK7 timing signal is applied to each of the amplifiers 562a-d and the analog to digital converters 564a-d. The output of the analog to digital converters 564a-d are applied to a multiplexer 566. Multiplexer 566 is a 4 to 1 multiplexer and receives the S10 and S11 timing signals. The amplifiers 562a-d, analog to digital converters 564a-d and multiplexer 566 are all contained on a printed circuit board housed within the rack assemblies 162 (FIG. 5) mounted within the inspection head assembly 50.

The output of multiplexer 566 is applied to multiplexer 422 (FIG. 18) which receives the S9 timing signal. The output of multiplexer 422 is alternately applied to either of the scan assembly memories 428 or 430 (FIG. 19A). The selection of the proper timing signals for the scan assembly memories 428 and 430 are controlled by multiplexers 568 and 570 through inverters 572 and 574. Multiplexer 568 receives the CLK2, CLK4 and S2 timing signals. Multiplexer 570 receives the CLK1, CLK3 and S2 timing signals. Multiplexers 568 and 570 select the proper clock rate for loading and unloading the shift registers comprising the scan assembly memories 428 and 430. The output of the scan assembly memories 428 and 430 is applied through a multiplexer 432 to the scan memory 434.

Area Sum Matrix

Referring to FIG. 20, a more detailed block diagram of the scan memory 434 (FIG. 18) is illustrated. Each of the blocks 580-603 represents a 256×8 bit shift register which receives parallel data, outputs parallel data and stores 256 words by 8 bits per word. Each block 580-603 therefore, corresponds to two of the shift registers 435-482 of the scan memory 434 (FIG. 18). The scan memory 434 stores eight sequential scans of data of the fabric web 77 with access to that data at 1536 element intervals, corresponding to cells 0, 1536, 3072, 4608 and 6144. The cell data from the output of multiplexer 432 (FIG. 18) is applied to the shift register block 580. The timing signals CLK3 and CLK4 are applied through inverters 604 and 605 to each of the shift register blocks 580-603.

Referring simultaneously to FIGS. 20, 22, and 23 the selection of the 25 cells whose values are summed to form the area sum matrix is illustrated. FIG. 23 illustrates an enlarged representation of a matrix 510 (FIG. 22) showing the individual cells of the matrix 510. The matrix 510 includes 13 horizontal rows, which are parallel to the fabric web motion indicated by arrow 512, and nine vertical columns which lie in the scan direction indicated by arrow 514. Row 1 of matrix 510 corresponds to the cell values in nine successive scans of the fabric web 77 and represents the first row of cells located at the fabric web edge 77a (FIG. 22). The cell values contained in columns 1, 3, 5, 7 and 9 of row 1 are tapped off from the scan memory 434 and stored in the stack memory 484 (FIG. 20). As the cell data is clocked through the scan memory 434, certain rows of cell data are skipped, such that the cell values of rows 4, 7, 10 and 13 are subsequently tapped from the scan memory 434 and stored within the stack memory 484 during each of the preceding four scans across the fabric web 77. During each scan, the five cell values from each row are serially output from the stack memory 484 to the adder 496 (FIG. 18).

The three test cell values are also tapped from the scan memory 434 and stored within the stack memory 484. The values of the eight cells within column 5 of the matrix 510 are tapped off and stored in a test cell delay memory 610, which comprises the shift registers 486-493. The eight cell values of rows 1-8 of column 5 are serially input into shift registers 486-493. The three test cell values are then tapped from shift registers 491-493 and stored in the "TC" 1-3 shift register locations within the stack memory 484. Stack memory 484 comprises parallel in/serial out shift registers, such that on each scan of the fabric web 77 the value of the five cells from a row and the three test cell values are output serially from the stack memory 484 to the adder 496.

The pattern of cells utilized in the calculation of the value of the area sum matrix illustrated in FIG. 23 is repeated on alternate odd scans of the fabric web 77. On the even scans of the fabric web 77 the cells tapped off from the scan memory 434 are selected from the even columns of the matrix 510. On each successive scan, the test cells selected are located centrally within the matrix 510. As the cell selection changes, to in effect cause the matrix 510 to move across the fabric web 77 from edge 77a to edge 77b in the direction of scan, the three test cell values also move across the width of the fabric web 77. Due to the combined effect of the fabric motion and the direction of scan, every cell across the fabric web 77 will be selected as a test cell value and compared to the value of the 25 surrounding cells composing the area sum matrix. Not every cell is utilized in the calculation to form the area sum reference value. In the preferred embodiment, the area sum calculation cells illustrated in FIG. 23 in the 9 column by 13 row matrix 510 are utilized. In the alternative, various other patterns in the selection of the 25 area sum calculation cells can be utilized. The skipping of rows within the matrix from which the five column values are selected serves to improve the average value for the area sum matrix. Because the effective motion of the matrix 510 is across the fabric width, and because the fabric motion is normal to the motion of the matrix 510, a dynamic two dimensional matrix is formed from which the area sum value is calculated.

The effective motion of the matrix 510 across the fabric web 77 from edge 77a to edge 77b is created through the operation of the column sum memory 500 (FIG. 18). For example, the first value of the area sum matrix 510 moves across the fabric web 77 is a sum of the five cell values of rows 1, 4, 7, 10 and 13. On the next scan of the fabric web 77, the cells utilized to calculate the value of the area sum matrix 510 are composed of the five cells in rows 4, 7, 10, 13 and 16 (FIG. 23). The motion of the matrix 510 across the width of the fabric 77 is therefore, caused by the subtraction of the value of the oldest sum of five values of a row stored in the column sum memory and the addition of a new sum of five values of a row on each subsequent scan of the fabric web 77.

Referring to FIG. 21, a more detailed block diagram of the column sum memory circuitry 500 of FIG. 18 is illustrated. The output of the stack memory 484 representing the value of five cells within a row are applied to an adder 496 and accumulator 498 which forms a sum to be referred to as the "row sum." Referring to FIG. 23, the value of the first row sum represents the sum of the values of column cells 1, 3, 5, 7 and 9 of row 1. This first row sum value is applied to the Location 1 shift registers 612 of the column sum memory 500 and to the adder 502. Adder 502 performs an addition function to add the value of the first row sum from Location 1 of the column sum memory 500 to the contents of accumulator 508, which during the first scan has a value of zero stored therein. The resultant sum is output from adder 502 to adder 506. Adder 506 performs an addition of the sum from adder 502 with the inverse of the sum from location 6 of the column sum memory 500. Inverter 504 generates the inverse of the value stored within Location 6, which during the first scan is zero, therefore adder 506 contains the value of the row sum value stored in Location 1.

On the next scan, the five cell values comprising columns 1, 3, 5, 7 and 9 of row 4 are output from the stack memory 484 to the adder 496 and accumulator 498. These five cell values are summed and applied to Location 1 of the column sum memory 500. The previous value stored at Location 1, representing the first row sum value, is shifted to Location 2. The new Location 1 value is then applied to adder 502, which sums the new Location 1 value with the Location 2 value previously stored in accumulator 508. The output of adder 502 is then applied to adder 506, which because no value was stored in Location 6 of the column sum memory 500 adds a zero to the sum of adder 502 and stores this value in accumulator 508. The value then stored in accumulator 508 represents the sum of ten cells, being those cells in rows 1 and 4 of the matrix 510 (FIG. 23).

On the next scan the values of columns 1, 3, 5, 7 and 9 of row 7 are tapped off from the scan memory 434 and stored within the stack memory 484. The output of the stack memory 484 is then applied to adder 496 and accumulator 498 to generate a third row sum value which is applied to Location 1 of the column sum memory 500. This third input to the column sum memory 500 causes a shift of the row sum values previously calculated, such that the second row sum value is shifted to Location 2 and the first row sum value is shifted from Location 2 to Location 3. The third row sum value representing the sum of the cell values of columns 1, 3, 5, 7 and 9 of row 7 is also applied to adder 502, which performs an addition with the value stored in accumulator 508. This sum is then applied to adder 506, which because Location 6 contains a zero value, adds a zero to the sum, and the resultant is stored in accumulator 508. After this third scan and input to the column sum memory 500, accumulator 508 stores the value of fifteen cells representing the five row values for each of rows 1, 4 and 7.

On the fourth scan, the five cell values of columns 1, 3, 5, 7 and 9 of row 10 are summed in adder 496 and accumulator 498 and applied to the first Location of column sum memory 500. The previous value stored in Location 1, 2 and 3 are shifted, such that these values are now stored in Locations 2, 3 and 4. The fourth row sum value is also applied to adder 502 which adds the fourth row sum value to the value stored in accumulator 508 and outputs this value to adder 506. Adder 506 adds this sum with the value stored in Location 6, zero, and the resultant sum is stored in accumulator 508. Accumulator 508 now contains the sum of twenty cell values.

On the next or fifth scan, cell values from columns 1, 3, 5, 7 and 9 of row 13 are tapped from the scan memory 434 and applied through the stack memory 484 to the adder 496 and accumulator 498. The resultant sum is applied to Location 1 of the column sum memory 500 causing the previously stored values to shift one location within the column sum memory 500. The fifth row sum value is also applied to adder 502 which performs an addition to the sum stored in accumulator 508. This resultant sum is applied to adder 506, which again because the Location 6 value of column sum memory 500 contains a value of zero, adds a zero to the sum of adder 502 for storage in accumulator 508. The value stored in accumulator 508 now represents the sum of 25 cells comprising those cells within the matrix 510 which are utilized to form the area sum calculation. The output of accumulator 508 representing the area sum is then applied to the comparator 536, which compares the value of the area sum, to the value of a test cell, multiplied by 25 and summed with the offset value to determine whether a defect exists within the test cell as previously described in connection with FIG. 18.

On the sixth scan, the cell values of columns 1, 3, 5, 7 and 9 of row 16 (FIG. 23) are tapped from the scan memory 434 and applied through the stack memory 484 to the adder 496 and accumulator 498. Adder 496 and accumulator 498 create a sum of these five cell values of row 16 and apply this sixth row sum value to Location 1 of the column sum memory 500. The previously stored values in Location 1–5 are shifted to be stored in Locations 2–6. The sixth row sum value is also applied to adder 502 which performs an addition with the value stored in accumulator 508. The output of adder 502 now represents the sum of 30 test cells and is applied to adder 506. Location 6 for the first time during the last five scans, now contains a value, representing the first row sum value of the five cells of row 1. The inverse of this first row sum value is applied through inverter 504 to adder 506. Adder 506 therefore, subtracts the value of the first row sum and applies this value to accumulator 508. Accumulator 508 now represents the sum of 25 cells. These 25 cells represent the values of columns 1, 3, 5, 7 and 9 of rows 4, 7, 10, 13 and 16. The output of accumulator 508 is then applied to the comparator 536 for comparison with the three test cells centered within the matrix 510 extending from row 4 to row 16.

Therefore, it can be seen that the matrix 510 previously extending from row 1 to row 13, has in effect moved to extend between rows 4 and 16 in a direction across the fabric web from edge 77a towards edge 77b. The operation of the column sum memory 500, adders 502 and 506 and the accumulator 508 continue to generate the area sum, which is applied to the comparator 536. The new row sum value inputted to the column sum memory 500 is always added by adder 502 to the accumulated sum stored in accumulator 508. The oldest most column sum value stored in Location 6 of the column sum memory 500 is always subtracted by adder 506 from the sum output from adder 502.

Defect Buffer Function

Referring to FIG. 24, a more detailed block diagram of the defect buffer 538, defect configuration circuit 540, defect latch 550 and width circuitry of FIG. 18 is illustrated. The output from the comparator circuitry 536 (FIG. 18) is applied to the multiplexer 537. The output of the comparator circuitry 536 represents a decision that either the test cell value is greater than the area sum value representing a positive decision, or a negative decision in which case the value of the test cell is less than the area sum matrix value. The outputs of the multiplexer 537 are applied through the flip-flop 537a to the shift registers of the defect buffer 538. Defect buffer 538 includes three, 256 word by 4 bit shift registers 636a-636d, 638a-638d, and 640a-640d. The output of flip-flop 537a is applied to shift register 636a, flip-flop 642, NAND gate 646 and NAND gate 648. The output of flip-flop 642 is applied to a flip-flop 650 whose output is applied to NAND gate 644 and to a NAND gate 651.

The decision data from the output of flip-flop 537a is circulated through the registers 636a, 638a, 640a, 636b, 638b and 640b and is applied to a flip-flop 652. The output of shift register 640b is also applied to NAND gates 646 and 651. The output of flip-flop 652 is applied to a flip-flop 654, whose output is applied to NAND gate 648. The operation of flip-flops 642, 650, 652 and 654 sets the NAND gates 644, 646, 648 and 651. An output of either of NAND gates 644, 646, 648 or 651 represents that a pair of decisions from the comparator 536 (FIG. 18) has been found corresponding to one of the defect cell configurations illustrated in FIG. 25. The outputs of NAND gates 644, 646, 648 and 651 indicate that a pair of bits outputted from NAND gates 634 match or do not match one of the configurations shown in FIG. 25.

The outputs of NAND gates 644, 646, 648 and 651 are applied to a four input NAND gate 656, whose output is applied through inverter 658 to an NAND gate 660. The defect data is allowed to recirculate in shift registers 636c, 638c, 640c, 636d, 638d, and 640d through a NAND gate 662 for the number of scans which represents an inch of fabric travel as determined by the velocity correction logic. When compacting for one inch of fabric motion is completed in the direction of the fabric motion, the recirculation NAND gate 662 is disabled by the timing signal $\overline{S15}$ generated by the counter 418 (FIG. 17). The disabling of NAND gate 662 causes the data from the shift register 640d to be output to a flip-flop 550a. The timing signals CLK11 and CLK12 are applied through inverters 664 and 666 to each of the shift registers 636, 638 and 640. Timing signals CLK11 and CLK12 are also applied through NAND gate 668 to flip-flops 642, 650, 652, 654, 550a and 550b. The output of flip-flop 550a to the computer interface 368 indicates that a positive defect has been detected. Flip-flop 550a is interconnected to flip-flop 550b, whose output is applied to the computer interface 368 representing the detection of a negative defect.

The output of inverter 658 is also applied to a flip-flop 670. The first defect detected by the defect configuration circuit 540 (FIG. 18) at the output of inverter 658 represents the edge 77a of the fabric web 77 (FIG. 22). The first output of inverter 658, therefore sets a flip-flop 670 to enable a counter 672. Counter 672 then counts the number of cells detected in each of ten scans across the fabric web 77. The total number of cells counted for ten scans are then stored in latches 674a, 674b, 676a and 676b. Counter 672 is then reset and counts the number of cells detected in each of the next three groups of ten scans each. The latches 674 and 676 therefore, accumulate the total number of cells detected in forty scans or approximately the number of scans required in four inches of fabric motion. Counters 678, 680 and 682 perform a divide by four function to divide the accumulated number of cells for the forty scans counted by counter 672 to represent the average fabric width for 40 scans or the average fabric width per inch over the last four inches of fabric motion.

The timing signal S16 generated by counter 420 (FIG. 17) is applied to counters 672, 678, 680 and 682. The timing signal CLK11 is applied to counters 678, 680 and 682. The output of inverter 658 is also applied through an inverter 684 to the latches 674 and 676. The output of the fabric width detection circuitry is applied to the computer interface 368 (FIG. 16).

Velocity Correction Function

Figure 26:
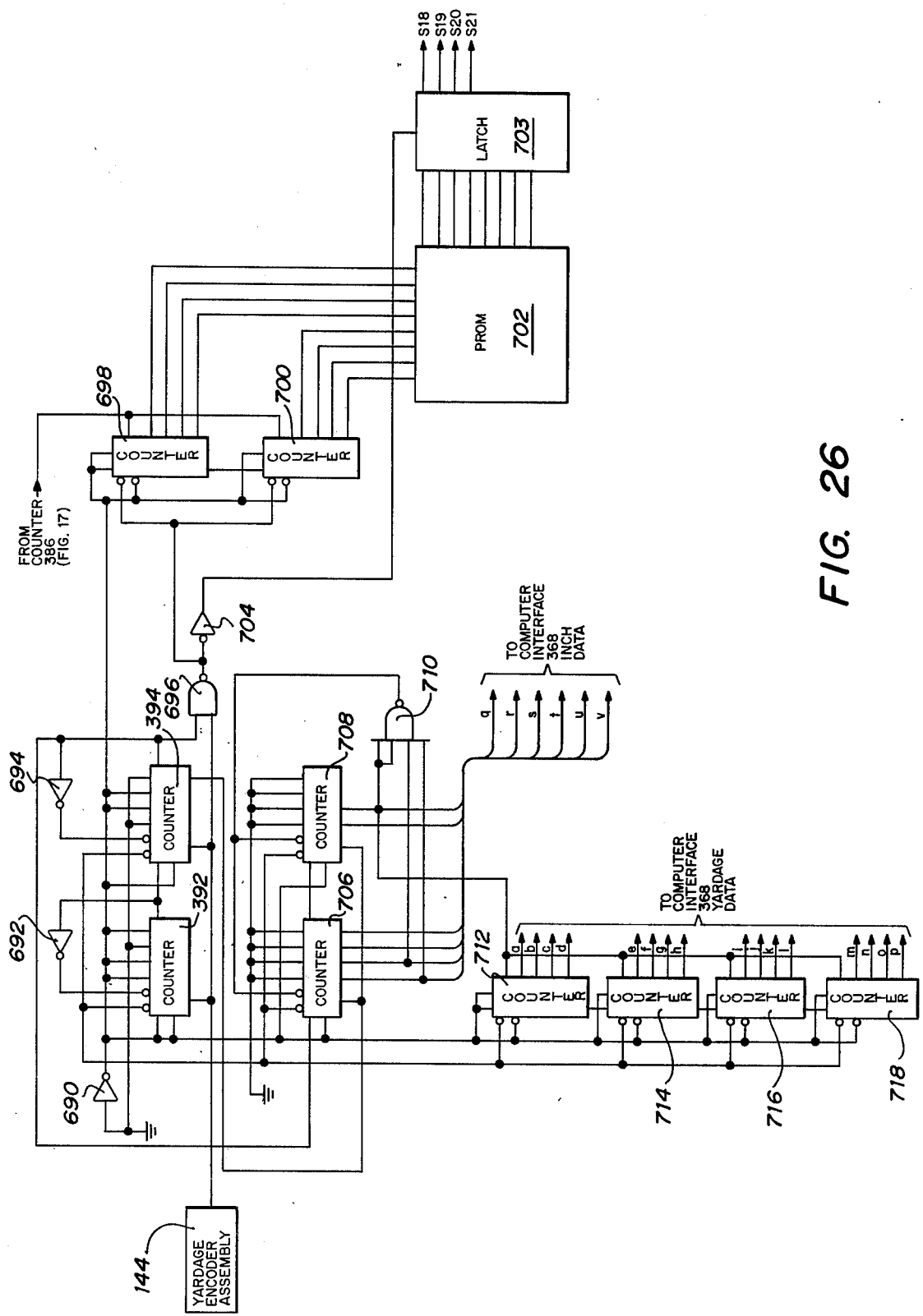
FIG. 26 is a detailed block diagram of the velocity correction circuitry shown in block diagram of FIG. 17.

Referring to FIG. 26, a more detailed block diagram of the velocity correction circuitry, yardage encoder assembly 144, counters 392, 394, 396 and 398 of FIG. 17 is illustrated. The yardage encoder assembly 144 generates 600 pulses per foot of fabric motion moving through the inspection head assembly 50. The output of the yardage encoder assembly 144 is applied to counters 392 and 394. The output of counter 392 is applied to counter 394. Counter 392 performs a divide by five function, while counter 394 provides for a divide by ten function. Through operation of counters 392 and 394 the output of the yardage encoder assembly is divided by 50 to output a one pulse per inch signal to counters 706 and 708. Counters 392 and 394 are also interconnected through inverters 690, 692 and 694. The output of counter 394 represents one pulse per inch of fabric motion and is applied through NAND gate 696 to counters 698 and 700. Counters 698 and 700 correspond to counter 400 (FIG. 17) and count the number of real scans per inch of fabric motion. The output of counter 386 (FIG. 17) representing two pulses per scan is also applied to counters 698 and 700.

The output of counters 698 and 700 are applied to a programmable read only memory 702, which comprises the read only memories 402 and 404 of FIG. 17. The output of the programmable read only memory 702 is applied to a latch 703 which generates the timing signals S18, S19, S20 and S21. The output of NAND gate 696 is also applied to latch 703 through an inverter 704.

The output of counter 394 is also applied to counters 706 and 708, which correspond to the counter 396 (FIG. 17). Counters 706 and 708 together with NAND gate 710 perform a divide by 36 function to provide an input to the computer interface 368 (FIG. 16) along signal lines g-v representing inches of fabric motion. The output of counters 392 and 394 are also applied to counters 712, 714, 716 and 718. Counters 712, 714, 716 and 718 correspond to counter 398 (FIG. 17) and function to provide an input to the computer interface 368 along signal lines a-p representing the number of yards of fabric moving through the inspection head assembly 50.

MEMORY AND ARITHMETIC FUNCTION CIRCUITRY

Scan Assembly Memory

Figure 27:
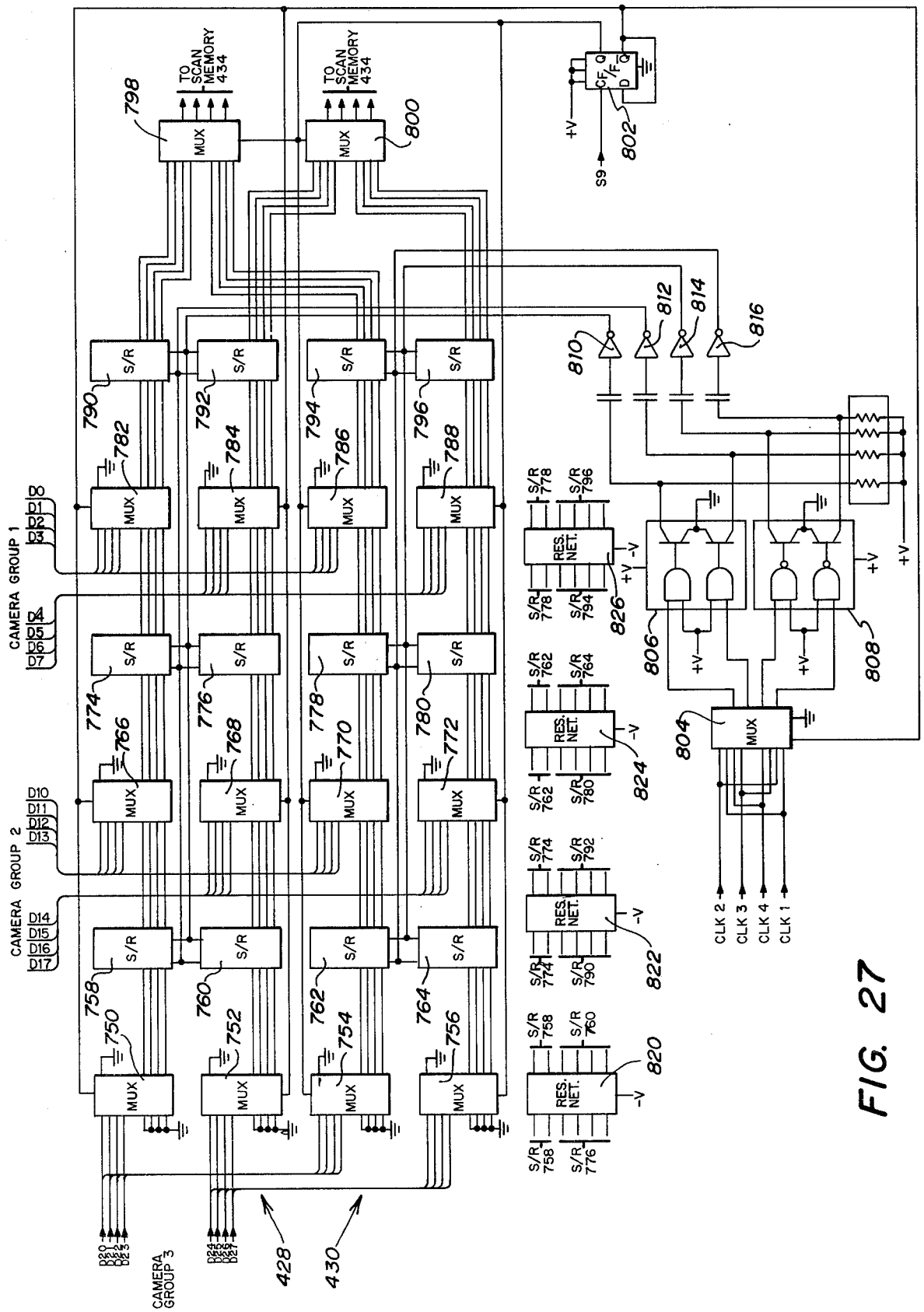
FIG. 27 is a detailed schematic diagram of the scan assembly memory shown in block diagram in FIG. 18.

Referring to FIG. 27, the schematic circuitry 428 and 430 of FIG. 18 is illustrated. The data from camera group 3 is applied along signal lines D20-D27 to multiplexers 750 and 752 associated with the scan assembly memory 428. When the scan assembly memory 428 is unloading, the data from camera group 3 is being loaded into the scan assembly memory 430 through multiplexers 754 and 756. Multiplexers 750, 752, 754 and 756 correspond to the multiplexer block 426 of FIG. 18. The four data bits from multiplexers 750 and 752 are applied to shift registers 758 and 760. Similarly, in the scan assembly memory 430, the four data bits from multiplexers 754 and 756 are applied to shift registers 762 and 764.

The data from camera group 2 is applied along signal lines D10-D17 to multiplexers 766 and 768, associated with the scan assembly memory 428. When the scan assembly memory 428 is being unloaded, the data from camera group 2 is applied to multiplexers 770 and 772, associated with the scan assembly memory 430. Multiplexers 766, 768, 770 and 772 correspond to the multiplexer 424 illustrated in the block diagram of FIG. 18. The four bits of data applied to each of multiplexers 766 and 768 are applied to shift registers 774 and 776 within the scan assembly memory 428. Similarly, the four bits of data applied to multiplexers 770 and 772 are applied to shift registers 778 and 780 associated with the scan assembly memory 430 (FIG. 18).

The data from camera group 1 is applied along signal lines D0-D7 to multiplexers 782 and 784, associated with scan assembly memory 428, and is applied to multiplexers 786 and 788 associated with the scan assembly memory 430. Multiplexers 782, 784, 786 and 788 correspond to the multiplexer block 422 of FIG. 18. The four bits of data from multiplexers 782 and 784 are applied to shift register 790 and 792, associated with the the scan assembly memory 428. The four bits of data from the multiplexers 786 and 788 are applied to shift registers 794 and 796, associated with the scan assembly memory 430. The output of shift registers 790 and 794 is applied to a multiplexer 798, which applies a serial output of the assembled scan 1-768 cells to the scan memory 434 (FIG. 18). Similarly, the output of shift registers 792 and 796 is applied to a multiplexer 800, which applies a serial output of the cell data 1-768 to the scan memory 434 (FIG. 18). Multiplexers 798 and 800 comprise the multiplexer block 432 of FIG. 18.

Flip-flop 802 is interconnected to multiplexers 750, 752, 766, 768, 782 and 784 associated with the scan assembly memory 428, and to the multiplexers 754, 756, 770, 772, 786 and 788 associated with the scan assembly memory 430. Flip-flop 802 may comprise, for example, a 7474 I/C and receives the S9 timing signal. The Q output of flip-flop 802 clocks the multiplexers for receiving data from the three camera groups in either the scan assembly memories 428 or 430. The Q output of flip-flop 802 sets up the condition to unload the scan assembly memory 428 or 430, which is not receiving data from the camera groups 1-3. The functions of the scan assembly memories 428 and 430 alternate. As one memory section is receiving data, the other memory section is shifting data out through multiplexers 798 and 800 to the scan memory 434 (FIG. 18). The output function is performed at a clock rate that is three times the frequency of the clock rate utilized to load the memory sections 428 and 430.

The selection of the clock rate is performed by a multiplexer 804 which receives the timing signals CLK1-CLK4. The output of multiplexer 804 is applied to a dual peripheral driver 806 having positive NAND gates. Driver 806 may comprise, for example, a 75452 I/C. The output of multiplexer 804 is also applied to a dual peripheral driver 808 having positive AND gates. Driver 808 may comprise, for example, a 75451 I/C. The output of driver 806 is applied through clock drivers 810 and 812 to the shift registers 758, 760, 774, 776, 790 and 792 of the scan assembly memory 428. The output of the driver 808 is applied through clock drivers 814 and 816 to the shift registers 762, 764, 778, 780, 794 and 798 of the scan assembly memory 430.

Resistor networks 820, 822, 824, and 826 are pull up and pull down resistors interconnected between stages of the shift registers as indicated in FIG. 27. The multiplexers shown in FIG. 27 are quad 2-line to 1-line multiplexers and may comprise, for example, 74157 I/Cs. The shift registers shown in FIG. 27 are 1024 bit shift registers parallel in/parallel out and may comprise, for example, 2502B I/Cs.

Scan Memory

Figure 28:
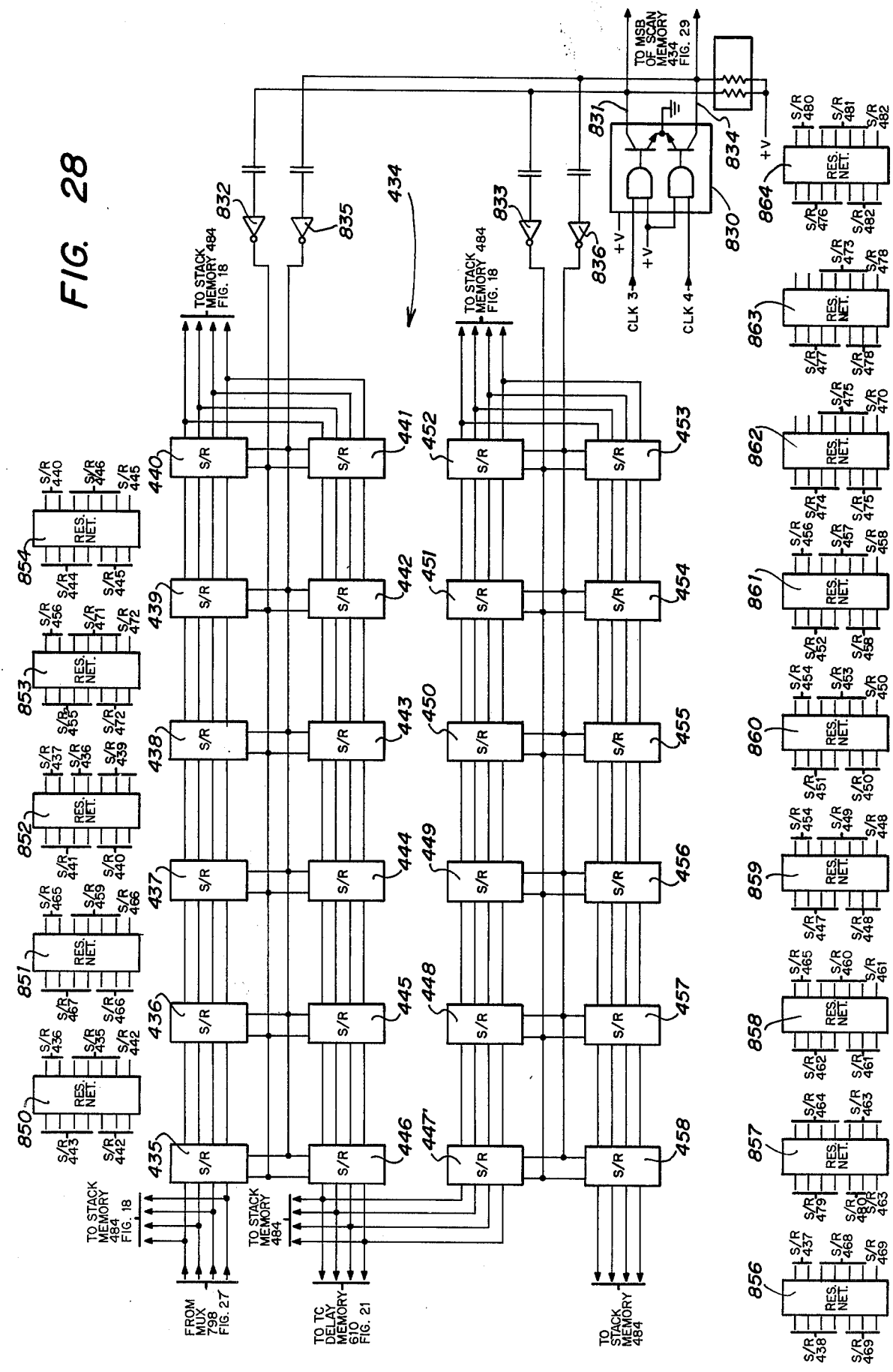
FIG. 28 is a detailed schematic diagram of a portion of the scan memory circuitry shown in block diagram in FIG. 20.

Referring to FIG. 28, the schematic circuitry which corresponds to the least significant bit shift registers of the scan memory 434 shown in block diagram of FIG. 18 is illustrated. The shift registers 435-458 correspond to the shift register blocks 435-458 of the scan memory 434 shown in block diagram of FIG. 18. The shift registers 435-458 are 1024 bit shift registers, arranged 264×4 and may comprise, for example, 2502B I/Cs. The output from multiplexer 798 (FIG. 27) is applied to the shift register 435 and to the stack memory 484 (FIG. 18). The data applied to shift register 435 is shifted through the shift registers 436-440 and is applied to the stack memory 484. This same data is then shifted through shift registers 441-446 and is applied to the stack memory 484, the test cell delay memory 610 (FIG. 20) and to the shift register 447. The data from shift register 446 is then circulated through shift registers 447-452 and is applied to the stack memory 484 and to shift register 453. The data from shift register 453 is then shifted through shift registers 454 through 458 and is applied to the stack memory 484. In this manner the data applied from the scan assembly memory multiplexer 432 (FIG. 18) to the scan memory 434 is tapped off at five taps for application to the stack memory 484. These five taps include shift registers 435, 440, 446, 452, and 458.

The data is clocked through the shift registers 435 through 458 by application of the timing signals CLK3 and CLK4 to a dual peripheral driver 830 having positive NAND gates. The driver 830 may comprise, for example, a 75452 I/C. The output of driver 830 is applied via signal line 831 to a clock driver 832, which is interconnected to shift registers 435-446. The output of driver 830 is also applied via signal line 831 to a clock driver 833, which is interconnected to shift registers 447-458. A second output of driver 830 is applied via signal line 834 to a clock driver 835, which is interconnected to shift registers 435-446. The output of driver 830 is also applied via signal line 834 to a clock driver 836, which is interconnected to shift registers 447-458.

Figure 29:
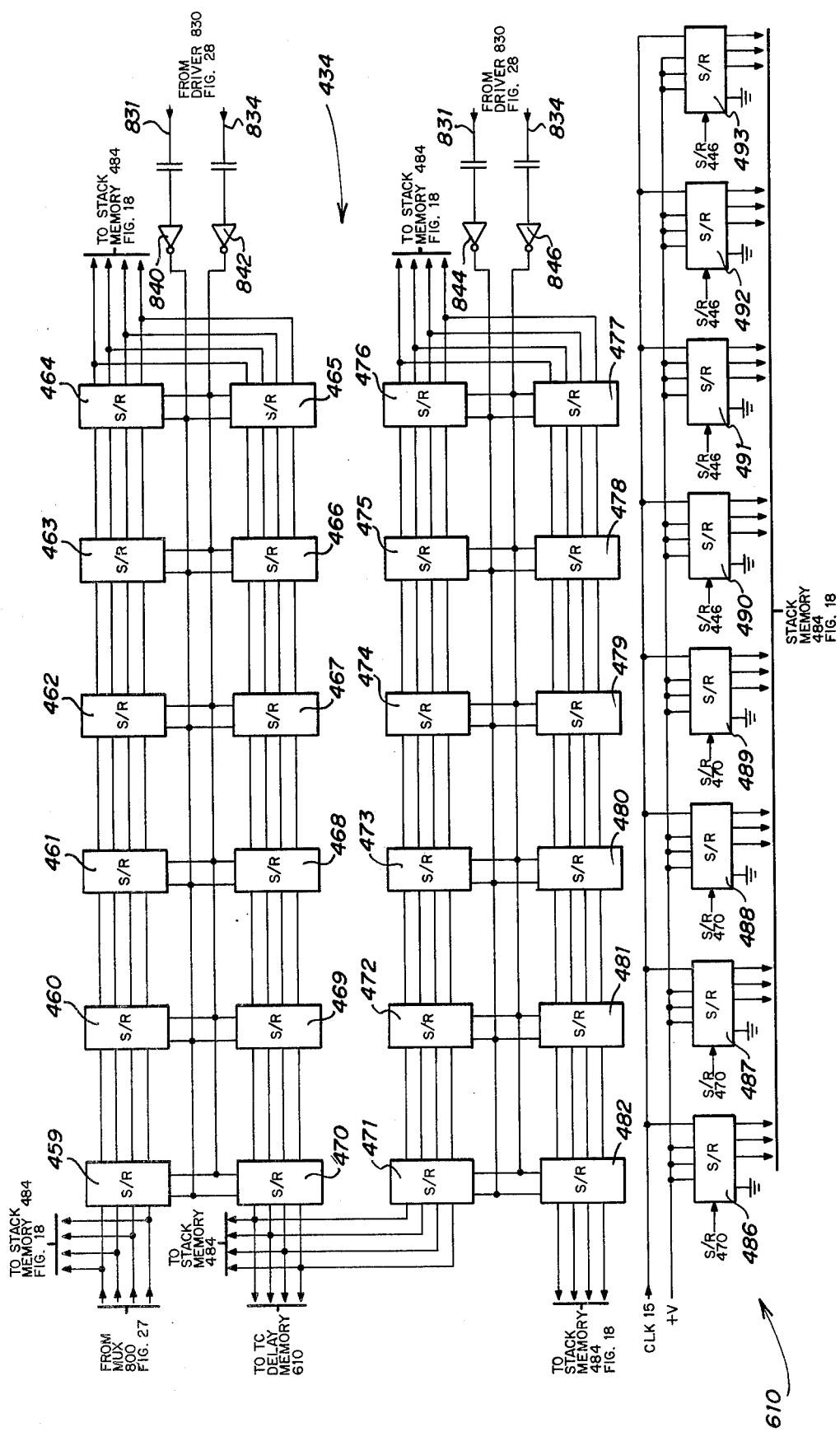
FIG. 29 is a detailed schematic diagram of a portion of the scan memory circuitry and the test cell delay memory circuitry shown in block diagram in FIG. 20.

Referring to FIG. 29, the schematic circuitry which corresponds to the most significant bit shift registers of the scan memory 434 (FIG. 18) and the test cell delay memory of the block diagram of FIG. 20 is illustrated. The output of multiplexer 800 (FIG. 27) is applied to the shift register 495. The output of shift register 459 is applied to shift register 460. The data is subsequently shifted through the shift registers 461-482. The five points at which the data is tapped off from the scan memory 434 are from shift registers 459, 464, 470, 476 and 482. The data applied to the test cell delay memory 610 (FIG. 20) is tapped off from the scan memory 434 from shift register 470.

The timing signals to clock the data through shift registers 459-482 are supplied from the driver 830 (FIG. 28) along signal lines 831 and 834 applied to clock drivers 840, 842, 844 and 846. The shift registers 459-482 are 1024 bit 256×4 shift registers and may comprise, for example, 2502B I/Cs.

Referring simultaneously to FIGS. 28 and 29, the resister networks 850-864 are interconnected between shift registers 435-482 as indicated. For example, the resister network 850 is interconnected between shift registers 443 and 442 on its input and shift registers 436, 435 and 442 on its output.

Referring to FIG. 29, the shift registers comprising the test cell delay memory 610 (FIG. 18) are illustrated. The shift registers 486-493 correspond to the shift register blocks 486-493 of the block diagrams of FIGS. 18 and 20. Shift registers 486-493 are 8 bit serial in/parallel out shift registers and may comprise, for example, 74164 I/Cs. The output of shift register 470 is applied to shift registers 486-489. The output of shift register 446 (FIG. 28) is applied to shift registers 490-493. The outputs of the shift registers 486-493 are applied to the stack memory 484 (FIG. 18). The timing signal CLK15 is applied to each of the shift registers 486-493.

Stack Memory

Figure 30:
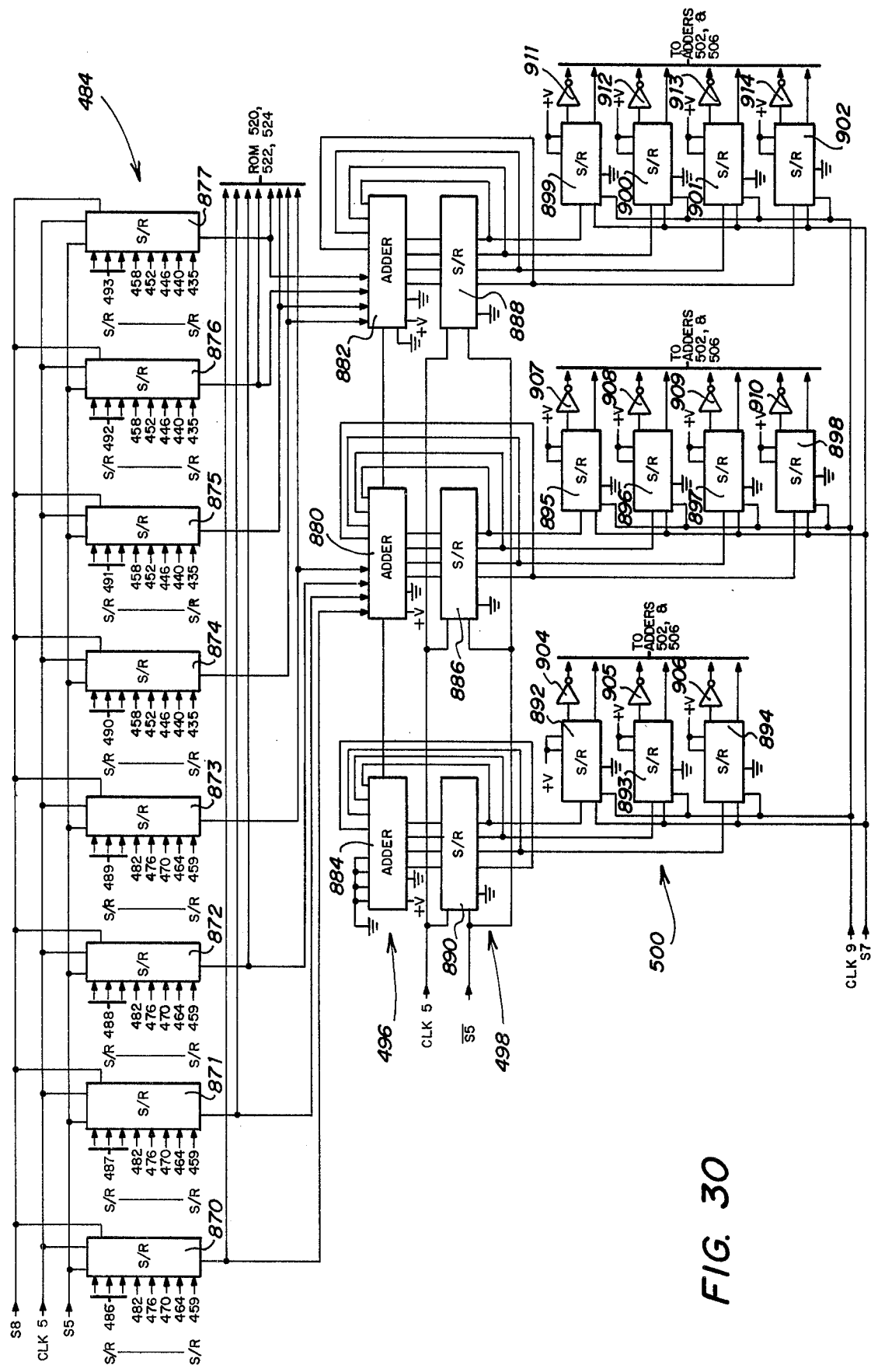
FIG. 30 is a detailed schematic diagram of the stack memory and a portion of the arithmetic function circuitry shown in block diagram in FIG. 18.

Referring to FIG. 30, the schematic circuitry corresponding to the stack memory block 484, adder block 496, accumulator block 498 and column sum memory block 500 of FIG. 18 is illustrated. The stack memory 434 includes shift registers 870-877. Shift registers 870-877 are 8 bit parallel in/serial out shift registers and may comprise, for example, 74165 I/Cs. Shift register 870 receives the output of the shift register 486 of the test cell delay memory 610. Shift register 871 receives the output of shift register 487 of the test cell delay memory 610. Shift register 872 receives the output of shift register 488 of the test cell delay memory 610. Shift register 873 receives the output of shift register 489 of the test cell delay memory 610. Each of the shift registers 870, 871, 872 and 873 further receives the output of the shift registers 482, 476, 470, 464 and 459 of the scan memory 434 (FIG. 29).

Shift register 874 receives the output of shift register 490 of the test cell delay memory 610. Shift register 875 receives the output of shift register 491 of the test cell delay memory 610. Shift register 876 receives the output of shift register 492 of the test cell delay memory 610. Shift register 877 receives the output of shift register 493 of the test cell delay memory 610 (FIG. 29). Each of the shift registers 874, 875, 876 and 877 further receives the outputs of the shift registers 458, 452, 446, 440 and 435 of the scan memory 434 (FIG. 28).

Each of the shift registers 870-877 receives the S8 timing signal, which is a clock inhibit signal, the S5 timing signal, which is a shift load signal and the CLK5 signal, which is the clocking signal. The outputs of shift registers 870, 871, 872 and 873 are each applied to the read only memories 520, 522 and 524 (FIG. 18) and an adder 880. The outputs of shift registers 874, 875, 876 and 877 are each applied to the read only memories 520, 522, and 524 (FIG. 18) and an adder 882. Adder 880 is interconnected to an adder 884. Adders 880, 882 and 884 are 4 bit binary adders and may comprise, for example, 7483 I/Cs. Adders 880, 882 and 884 comprise the adder block 496 of the block diagram of FIG. 18. The data applied from the shift registers 870-877 is serially outputted to the adders 880 and 882. The outputs of adders 880, 882 and 884 are applied to shift registers 886, 888 and 890.

Shift registers 886, 888 and 890 are 4 bit parallel access shift registers and may comprise, for example, 74195 I/Cs. Shift registers 886, 888 and 890 correspond to the accumulator block 498 of block diagram of the FIG. 18. The timing signals CLK5 and $\overline{S5}$ are applied to shift registers 886, 888 and 890. The $\overline{S5}$ timing signal is the timing signal utilized to load the stack memory 434 and at the same time to clear the shift registers 886, 888 and 890. The five cell values tapped off from the scan memory 434 (FIG. 18) are added through the operation of adder 496 and accumulator 498 (FIG. 18) as previously described. The sum of the five cell values on a row are accumulated in the shift registers 886, 888 and 890.

The output of shift register 890 is applied to shift registers 892, 893 and 894. The output of shift register 886 is applied to shift registers 895, 896, 897 and 898. The output of shift register 888 is applied to shift registers 899, 900, 901 and 902. Shift registers 892-902 are 8 bit serial in/parallel out shift registers and may comprise, for example, 74164 I/Cs. Shift registers 892-902 comprise the column sum memory block 500 of the block diagram of FIG. 18. The timing signal CLK9 is applied to shift registers 892-902 to load the data from shift registers 886, 888 and 890 into the shift registers 892-902. The S7 timing signal is also applied to shift registers 892-902. The outputs of shift registers 892-902 are applied to the adder 502 and through an associated inverter 904-914 to the adder 506 (FIG. 18). The inverters 904-914 correspond to the inverter block 504 of the block diagram of FIG. 18.

Arithmetic Functions

Figure 31:
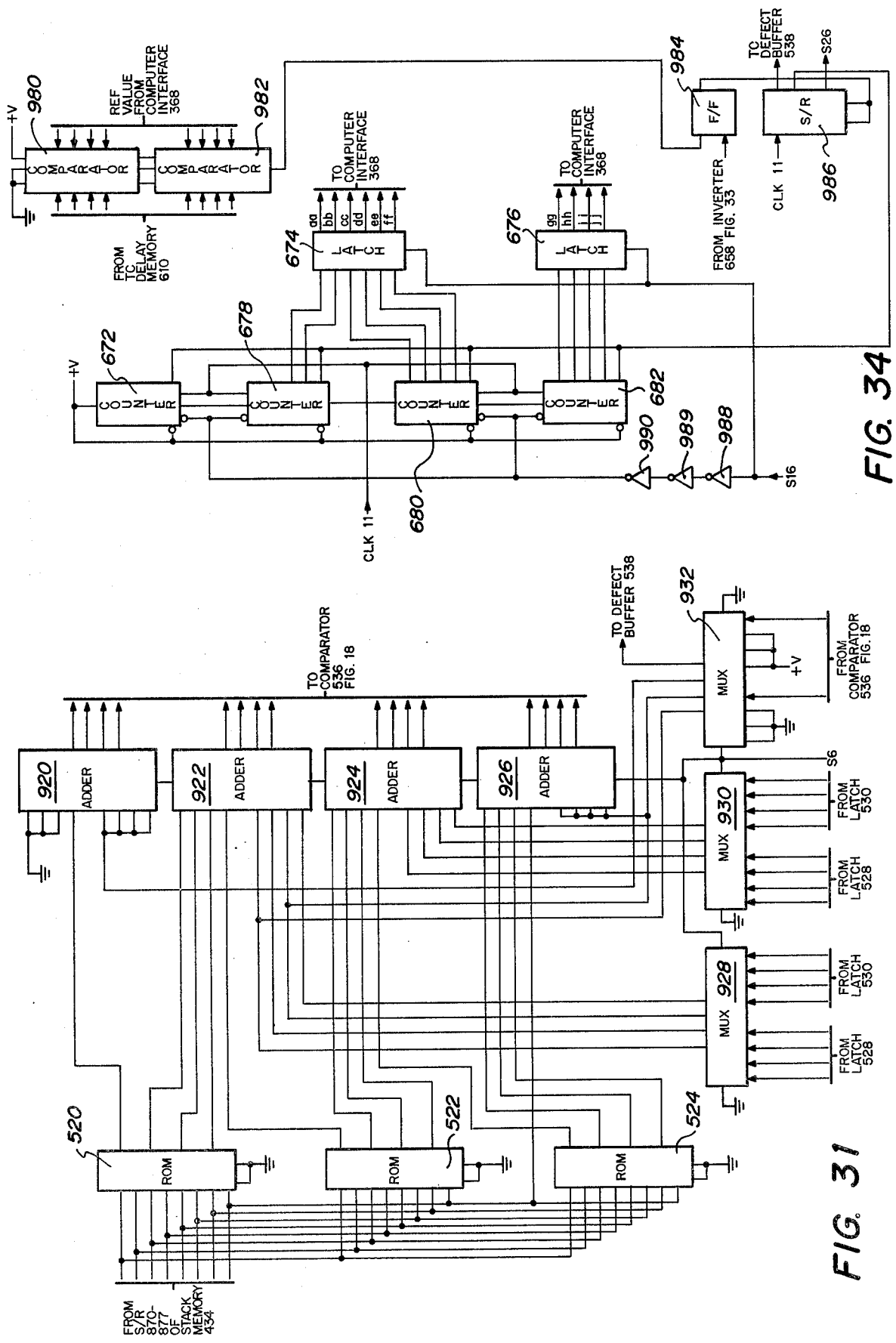
FIG. 31 is a detailed schematic diagram of the offset selector circuitry of the scan memory circuitry shown in block diagram in FIG. 18.

Referring to FIG. 31, the schematic circuitry corresponding to the read only memories 520, 522 and 524, the multiplexer block 532 and adder block 526 of the block diagram of FIG. 18 is illustrated. The test cell values from the shift registers 870-877 of the stack memory 434 are applied to read only memories 520, 522 and 524. The test cell values function as the address for read only memories 520, 522 and 524, which generate an output of 25 times the address. Read only memories 520, 522 and 524 may comprise, for example, 1024 I/Cs.

The output of read only memory 520 is applied to adders 920 and 922. The output of read only memory 522 is applied to the adder 922 and an adder 924. The output of read only memory 524 is applied to the adder 924 and an adder 926. Adders 920, 922, 924 and 926 are 4 bit binary adders and may comprise, for example, 7483 I/Cs. The adders 920, 922, 924 and 926 correspond to the adder block 526 of the block diagram of FIG. 18.

The positive and negative offset values are applied from the latches 528 and 530 (FIG. 18) to multiplexers 928 and 930. Multiplexer 932 is interconnected to multiplexers 928 and 930 and functions to multiplex the data out of multiplexers 928 and 930 and apply this data to the adders 922 and 924. Multiplexers 928, 930 and 932 are quad 2-line to 1-line multiplexers and may comprise, for example, 74157 I/Cs. The multiplexers 928, 930 and 932 comprise the multiplexer block 532 of the block diagram of FIG. 18. The adders 920, 922, 924 and 926 perform an addition or subtraction of the offset value with the test cell value. The output of adders 920, 922, 924 and 926 are then applied to the comparator 536 (FIG. 18).

Figures 32, 33:
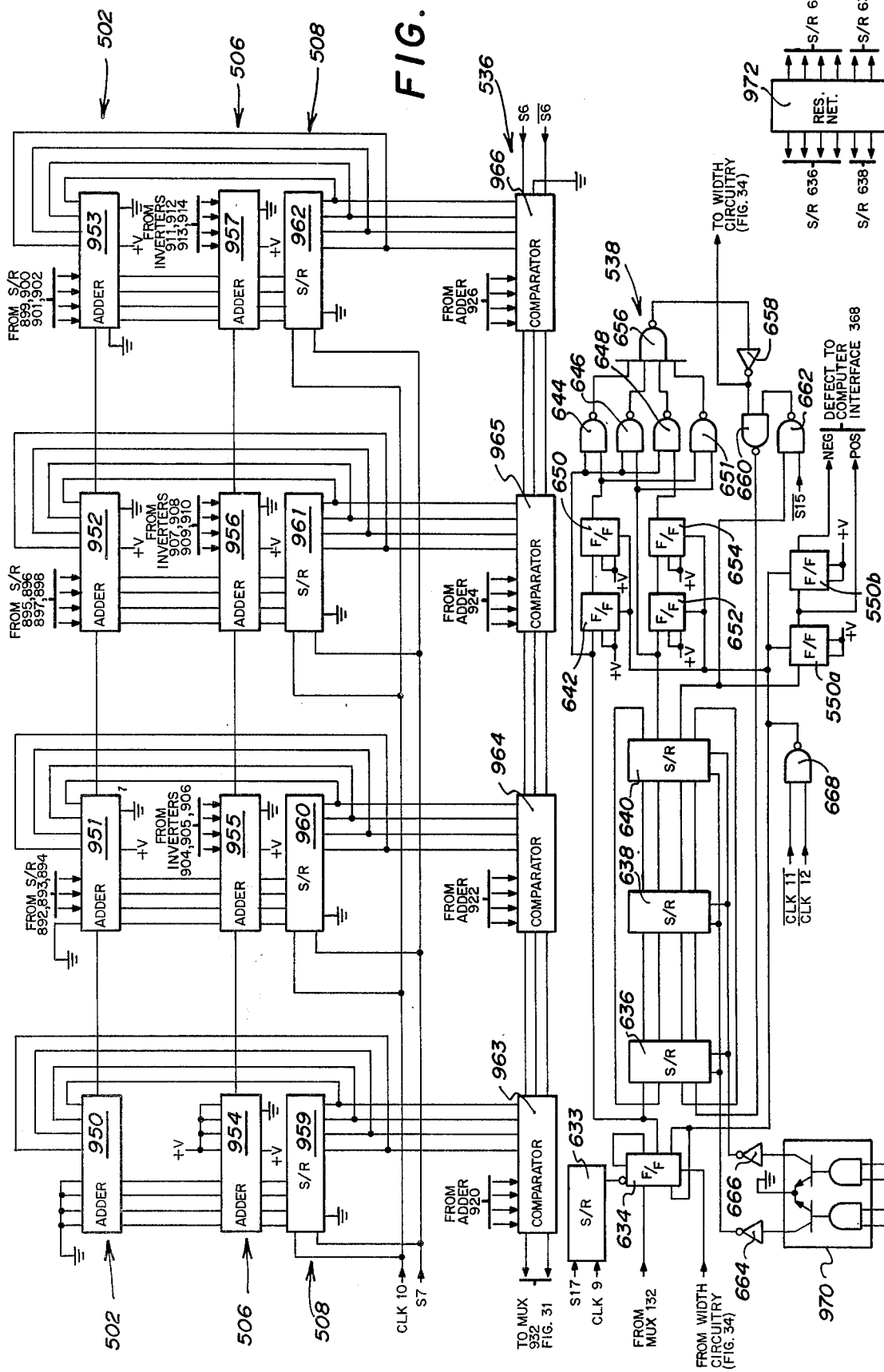
FIG. 32 is a detailed schematic diagram of a portion of the arithmetic function circuitry shown in block diagram in FIG. 18.
FIG. 33 is a detailed schematic diagram of the data compaction circuitry of the scan memory circuitry shown in block diagram in FIG. 24.

FIG. 32 illustrates the schematic circuitry corresponding to the adder blocks 502 and 506, the accumulator block 508 and the comparator block 536 of the block diagram of FIG. 18. The adder block 502 includes adders 950, 951, 952 and 953. Adders 950-953 are 4 bit binary adders and may comprise, for example, 7483 I/Cs. Adder 951 receives as its input the output of shift registers 892, 893 and 894 of the column sum memory 500 (FIG. 30). Adder 952 receives the output of shift registers 895-898 of the column sum memory 500 (FIG. 30). The adder 953 receives as its input the outputs of shift registers 899-902 of the column sum memory 500.

The outputs of adders 950-953 are applied to the adder 506 (FIG. 18). Adder 506 includes adders 954, 955, 956 and 957. Adders 954-957 are 4 bit binary adders and may comprise, for example, 7483 I/Cs. The adder 955 receives as its input the inverted output of shift registers 892, 893 and 894 through the inverters 904, 905 and 906 (FIG. 30). The adder 956 receives as an input the outputs from shift registers 895-898 through inverters 907-910. The adder 957 receives as an input the output of shift registers 899-902 through inverters 911-914. Adder 506 performs the subtraction function of subtracting the oldest value stored in the column sum memory 500, which is that value stored in Location 6 of the column sum memory 500 (FIG. 21), from the sum formed in adder 502 of the values stored in Locations 1-5 of the column sum memory 500.

The output of adders 954-957 is applied to the accumulator 508. Accumulator 508 includes shift registers 959, 960, 961 and 962. Shift registers 959, 960, 961 and 962 are 4 bit parallel access shift registers and may comprise, for example, 74195 I/Cs. The output of shift registers 959-962 is applied to the adders 950-953 of the adder 502 to perform the summing operation of the row sum values stored within the six locations of the column sum memory 500 (FIG. 21).

The outputs of the shift registers 959-962 of the accumulator 508 are applied to comparators 963, 964, 965 and 966. Comparators 963-966 are 4 bit magnitude comparators and may comprise, for example, 7485 I/Cs. Comparator 966 receives the S6 and $\overline{S6}$ timing signals. Comparator 963 receives the output of the adder 920 (FIG. 31) of the adder 526 (FIG. 18). Comparator 964 receives the output of adder 922 (FIG. 31). Comparator 965 receives the output of adder 924 (FIG. 31). Comparator 966 receives the output from adder 926 (FIG. 31) of the adder 526. The inputs to comparators 963-966 from the adder 526 represent the value of the test cell multiplied by 25, plus or minus the value of the offset. This test value is compared in comparators 963-966 with the reference value from the area sum matrix of 25 cell values output from the shift registers 959-962. The output of comparator 963 is applied to the multiplexer 932 (FIG. 31) for application to the defect buffer 538 (FIG. 18). The results of the comparison performed by the comparators 963-966 are stored in the shift registers 636, 638 and 640 (FIG. 24) of the defect buffer 538.

Referring to FIG. 33, the schematic circuitry which corresponds to the block diagram of the defect buffer 538 of FIG. 24 is illustrated wherein like numerals are utilized for like and corresponding components. The timing signals CLK11 and CLK12 are applied to a dual peripheral driver 970 having positive NAND gates. The dual peripheral driver 970 may comprise, for example, a 75452 I/C. The outputs of the driver 970 are applied to clock drivers 664 and 666. The outputs of clock drivers 664 and 666 apply clocking pulses to the shift registers 636, 638 and 640. The S17 and CLK9 timing signals are applied to a shift register 633, whose output is applied to the flip-flop 634. Flip-flop 634 also receives as inputs, the outputs from the multiplexer 932, the width circuitry and the output of NAND gate 668. Flip-flop 634 provides an output to shift register 636, flip-flop 642, NAND gate 646 and NAND gate 648. The output of flip-flop 642 is applied to the flip-flop 650, whose output is applied to NAND gate 644 and to the NAND gate 651.

The output of the shift register 640 is applied to the flip-flop 652 and to the NAND gates 646 and 651. The output of the flip-flop 652 is applied to the flip-flop 654, whose output is applied to NAND gate 648. The operation of flip-flops 642, 650, 652 and 654 sets the NAND gates 644, 646, 648 and 651. As previously discussed in conjunction with FIG. 24, an output of either of the NAND gates 644, 646, 648 or 651 represents that a pair of decisions from the comparator 536 (FIG. 32) has been found, which corresponds to one of the four defect cell configurations illustrated in FIG. 25.

The outputs of NAND gates 644, 646, 648 and 651 are applied to the four input NAND gate 656, whose output is applied through inverter 658 to NAND gate 660. The output of inverter 658 is also applied to the width circuitry (FIG. 34) to indicate that the edge of the fabric web 77 has been detected. The defect data is allowed to recirculate in shift registers 636, 638 and 640 through the recirculation NAND gate 662 for the number of scans which represents an inch of fabric travel as determined by the velocity correction logic circuitry. When compacting for one inch of fabric motion is completed in the direction of the fabric motion, the recirculation NAND gate 662 is disabled by the timing signal $\overline{S15}$ to cause the data to be shifted out of shift register 640 to the flip-flop 550a.

The output of flip-flop 550a indicates that a positive defect has been detected and is applied to the computer interface 368. Flip-flop 550a is interconnected to flip-flop 550b whose output indicates that a negative defect has been detected and is applied to the computer interface 368. The timing signals CLK11 and CLK12 are applied through NAND gate 668 to flip-flops 634, 642, 650, 652, 654, 550a and 550b. A resistor network 972 is interconnected between shift registers 636, 638 and 640 as indicated in FIG. 33.

Referring to FIG. 34, the schematic circuitry corresponding to the width circuitry shown in the block diagram of FIG. 24 is illustrated. An output from each of the shift registers 486–493 of the test cell delay memory 610 (FIG. 20) is applied to comparators 980 and 982. Comparators 980 and 982 are 4 bit magnitude comparators and may comprise, for example, 7485 I/Cs. Comparators 980 and 982 also receive an input of a reference value from the computer interface 368. The output of comparator 982 is applied to a flip-flop 984, which also receives an input signal from the inverter 658 of the width circuitry illustrated in FIG. 33. The operation of the comparators 980 and 982 and flip-flop 984 generates an output signal from flip-flop 984 to indicate that the edge of the fabric web 77 has been detected. The output of flip-flop 984 is applied to a shift register 986, whose output is applied to the flip-flop 634 (FIG. 33). The shift register 986 is an 8 bit serial in/parallel out shift register and may comprise, for example, a 74164 I/C.

The output of shift register 986 is also applied to counters 672, 678, 680 and 682. Counters 680 and 682 also receive the timing signal S16 through inverters 988, 989 and 990. Counters 672, 678, 680 and 682 also receive the CLK11 timing signal.

The outputs of counters 678 and 680 are applied to a latch 674. The output of counter 682 is applied to the latch 676. The operation of counters 672, 678, 680 and 682 together with latches 674 and 676 calculate the average width of the fabric web for 40 scans of the fabric web 77. This fabric width data is output from latches 674 and 676 along signal lines aa–jj to the computer interface 368 (FIG. 16).

COMPUTER INTERFACE CIRCUITRY

Figure 35A:
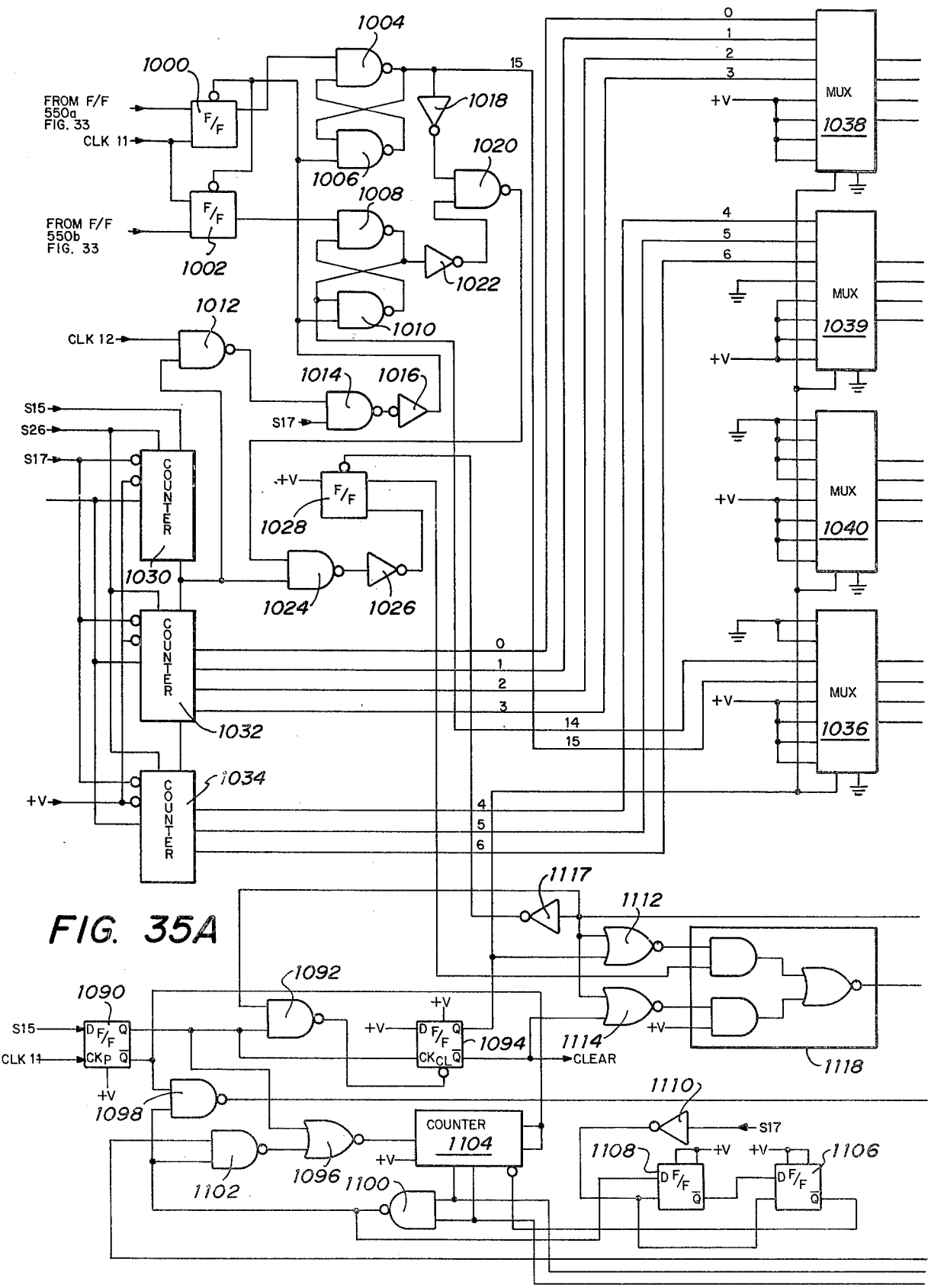
FIGS. 35A and 35B are detailed schematic diagrams of a portion of the computer interface circuitry shown in block diagram of FIG. 16.
Figure 35B:
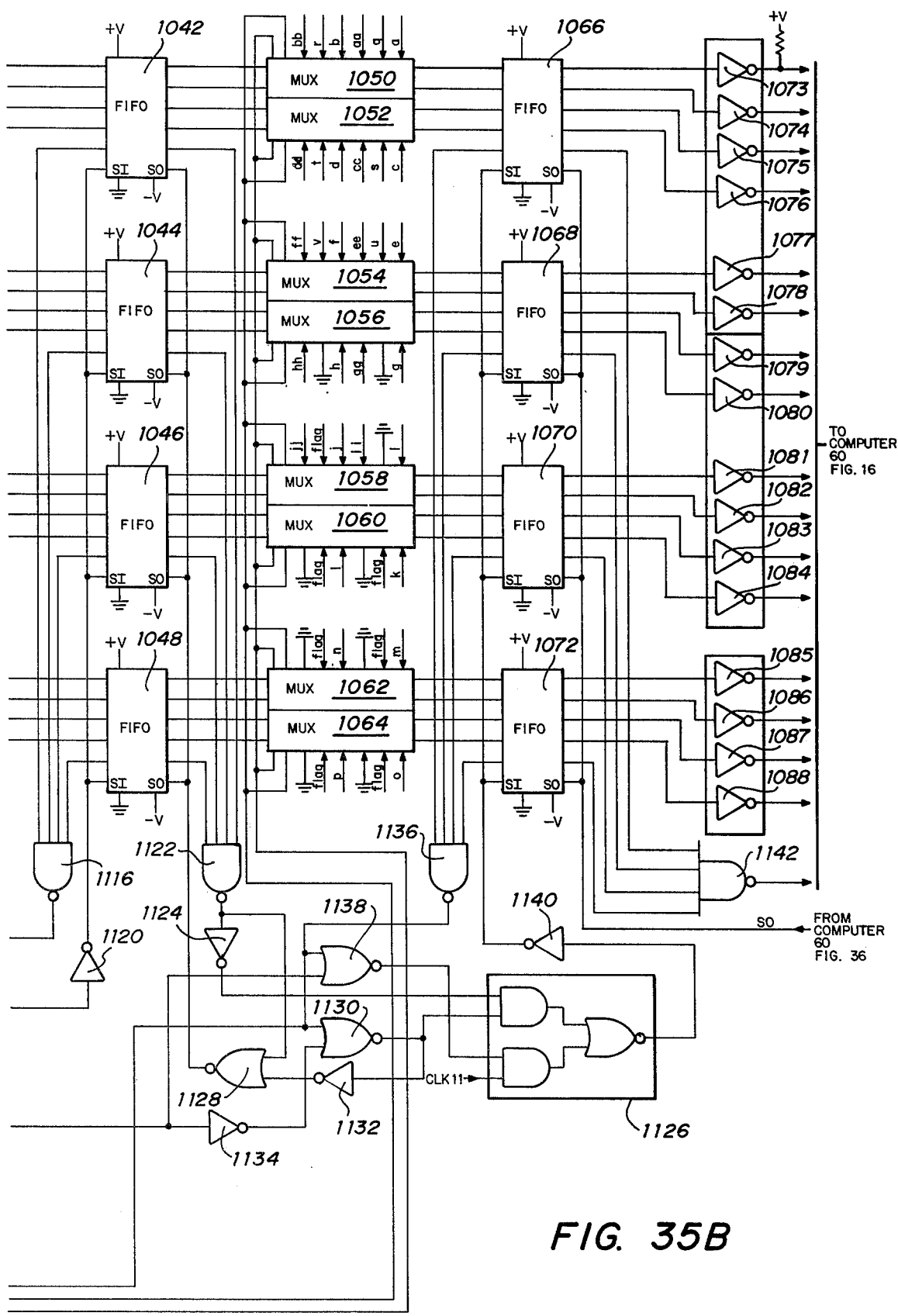

Referring to FIGS. 35A and 35B, the schematic circuitry which corresponds to a portion of the computer interface block 368 of FIG. 16 is illustrated. FIGS. 35A and 35B are drawn to be matched in a side-by-side relationship to illustrate this portion of the computer interface circuitry. The output of the flip-flop 550a (FIG. 33) representing a positive defect is applied to a flip-flop 1000. A positive defect indicates that the test cell value is more positive than the value of the area sum matrix. The output of flip-flop 550b (FIG. 33) is applied to a flip-flop 1002 representing a negative defect. A negative defect indicates that the test cell value is less than the value of the area sum matrix. The timing signal CLK11 is also applied as an input to flip-flops 1000 and 1002. The output of flip-flop 1000 is applied to a NAND gate 1004, whose output is applied to a NAND gate 1006. The output of NAND gate 1006 is also applied as an input to NAND gate 1004. The output of flip-flop 1002 is applied to a NAND gate 1008, whose output is applied to a NAND gate 1010. The output of NAND gate 1010 is also applied as an input to NAND gate 1008.

The timing signal CLK12 is applied to a NAND gate 1012, whose output is applied to a NAND gate 1014. NAND gate 1014 also receives the S17 timing signal. The output of NAND gate 1014 is applied through an inverter 1016 to provide an input to NAND gates 1006 and 1010 and to the flip-flops 1000 and 1002. The output of NAND gate 1004 is applied through an inverter 1018 to NAND gate 1020. The output of NAND gate 1008 is applied through an inverter 1022 to NAND gate 1020. The output of NAND gate 1020 is applied to NAND gate 1024 whose output is applied through inverter 1026 to a flip-flop 1028.

The $\overline{S15}$ timing signal is applied to a counter 1030 which is a 4 bit counter. Counter 1030 may comprise, for example, a 74160 I/C. Counter 1030 is interconnected to a counter 1032, which is interconnected to a counter 1034. Counters 1032 and 1034 are 4 bit counters and may comprise, for example, 74161 I/Cs. The timing signals S26 and S17 are applied to counters 1030, 1032 and 1034.

Counter 1030 counts for a total of ten cell values in the direction of scan across the fabric web 77. During this count of ten cells, if either of the flip-flops 1000 or 1002 is rendered low due to an output from flip-flops 550a and 550b (FIG. 13) then either NAND gate 1004 or NAND gate 1008 is latched. Any one of the ten cells counted by the counter 1030 may possess a defect, such that the NAND gates 1004 and/or 1008 will be set. After counter 1030 has counted for ten values, an output is provided to enable NAND gates 1024 and 1012. Enabling of gate 1012 will enable NAND gates 1004 and 1008 to output data if these NAND gates have been previously set by receipt of defect data.

If NAND gates 1004 and 1008 have been set, their outputs are applied along signal lines 15 and 14 to a multiplexer 1036. The input along signal lines 14 and 15 to multiplexer 1036 represents two data bits, which indicate to the computer 60 that a defect is present in the last inch of fabric inspected. Counters 1030, 1032 and 1034, in effect compact the data by a factor of ten to input data to the computer in inch increments. The outputs of counters 1032 and 1034 along signal lines 0–6 represent the address of the defect across the fabric width. This address represents the horizontal position of the defect from the edge of the fabric web 77. The outputs of counters 1032 and 1034 are applied to multiplexers 1038 and 1039.

Counter 1030 is reset each time the edge of the fabric is detected through the timing signal $\overline{S15}$ to clear counter 1030. Each time an inch of fabric is countered by counter 1030, a determination of whether the NAND gates 1004 and 1008 are set is made to create a word that contains the address bit of a defect, along signal lines 0–6 and the value of the defect. Counters 1032 and 1034 supply the location of the defect measured from the edge of the fabric web 77 for application to the computer 60. Data is sent to the computer for every inch of fabric motion regardless of whether any defects have been detected.

Multiplexers 1036, 1038, 1039 and 1040 are Quad 2-line to 1-line multiplexers and may comprise, for example, 74157 I/Cs. The output of multiplexers 1038, 1039, 1040 and 1036 are applied to first in/first out registers 1042, 1044, 1046 and 1048. The first in/first out registers 1042, 1044, 1046 and 1048 may comprise, for example, AM3341 FIFOs. The output of FIFO 1042 is applied to multiplexers 1050 and 1052. The output of FIFO 1044 is applied to multiplexers 1054 and 1056. The output of FIFO 1046 is applied to multiplexers 1058 and 1060. The output of FIFO 1048 is applied to multiplexers 1062 and 1064. Multiplexers 1050, 1052, 1054, 1056, 1058, 1060, 1062 and 1064 are dual 4-line to 1-line multiplexers and may comprise, for example, 74153 I/Cs. Each of the multiplexers 1050–1064 receives yardage and inch data from the yardage encoder assembly and related circuitry (FIG. 26) along signal lines a–v. In addition, multiplexers 1050–1064 receive width data from the width circuitry (FIG. 34) along signal lines aa–jj.

The output of multiplexers 1050 and 1052 are applied to a first in/first out register 1066. The output of multiplexers 1054 and 1056 are applied to a first in/first out (FIFO) register 1068. The output of multiplexers 1058 and 1060 are applied to a first in/first out register 1070. The output of multiplexers 1062 and 1064 are applied to a first in/first out register 1072. First in/first out register 1066, 1068, 1070 and 1072 may comprise, for example, AM3341 FIFOs. The outputs of FIFOs 1066, 1068, 1070 and 1072 are applied through hex drivers 1073–1088 to the computer 60 (FIG. 16).

There are at least four data words sent to the computer 60. The first word contains the yardage information relating to the yard of the fabric web being inspected. The second word contains the inches within the yard that is being inspected, zero to 35 inches. Also contained within the second data word are bits indicating the type of defect detected. The third data word contains the width calculation. The fourth data word contains the defect information including the address of the defect. The number of defect words depends upon the number of defects. To identify the end of a sequence of four data words, a trailer word is included. The trailer word is in all ones code, which indicates to the computer the end of the four word grouping. Each time a trailer word is input to the computer 60, the computer is alerted that the proceeding four words have pertinent information to be analyzed. In effect, the computer will initially just search for trailer words. The first three words, yardage, inches and width are referred to as header words. The fourth word is referred to as the defect word. The FIFOs 1066, 1068, 1070 and 1072 are completely loaded with the four data words before a signal is sent to the computer 60, identifying to the computer that all data is loaded and that the computer 60 should therefore be prepared to receive data.

The multiplexers 1036, 1038 and 1039 multiplex in either the defect data or strobe the all ones code for the trailer word. At the completion of loading defect words, the multiplexers switch to the trailer word and create the all ones code for loading into the FIFOs 1042, 1044, 1046 and 1048. The multiplexers 1050–1064 strobe the three header words, yardage, inches and width, input along signal lines a–v and aa–jj and strobe in the defect and trailer words to the FIFOs 1066, 1068, 1070 and 1072.

The control circuitry for the FIFOs 1042, 1044, 1046, 1048, 1066, 1068, 1070 and 1072 is also illustrated in FIGS. 35A and 35B. The S15 timing signal and CLK11 timing signal are applied to a flip-flop 1090 at the beginning of each scan pulse. The output of flip-flop 1090 is applied to a NAND gate 1092, flip-flop 1094 and NOR gate 1096. The inverted output of flip-flop 1090 is applied to NAND gate 1098, which also receives an input from NAND gate 1100. NAND gate 1100 also provides an input to NAND gate 1102, whose output is applied to NOR gate 1096. The output of NOR gate 1096 is applied to a counter 1104. Counter 1104 is a four bit counter and may comprise, for example, a 74161 I/C. Counter 1104 also receives an input from a flip-flop 1106, which is interconnected to a flip-flop 1108. Flip-flop 1108 receives the S17 timing signal through inverter 1110. The output of counter 1104 is applied to the multiplexers 1050, 1052, 1054, 1056, 1058, 1060, 1062 and 1064 and generates the shift in signal to load the three header words into FIFOs 1066, 1068, 1070 and 1072.

The output of flip-flop 1094 is applied to a NOR gate 1112. The inverted output of flip-flop 1094 is applied to a NOR gate 1114. NOR gates 1112 and 1114 also receive an input from NAND gate 1116, which is interconnected to FIFOs 1042, 1044, 1046 and 1048. NAND gate 1116 through an inverter 1117 (FIG. 35A) provides an input to flip-flop 1028. NAND gate 1116 functions to test the input ready of the four FIFOs 1042, 1044, 1046 and 1048. If all four FIFOs are ready, NAND gate 1116 will enable NOR gates 1112 and 1114 to output to a dual 2-wide, 2-input AND/OR inverter gate 1118. The gate 1118 may comprise, for example a 7451 I/C. The output of gate 1118 is applied through an inverter 1120 to the shift input terminals of the FIFOs 1042, 1044, 1046 and 1048.

FIFOs 1042, 1044, 1046 and 1048 are interconnected to a NAND gate 1122, which functions to indicate that the data stored in FIFOs 1042, 1044, 1046 and 1048 is ready to be output. NAND gate 1122 is interconnected through an inverter 1124 to a dual 2-wide, 2-input AND/OR inverter gate 1126. Inverter gate 1126 may comprise, for example, a 7451 I/C. The output of NAND gate 1122 is also applied to NOR gate 1128, which receives an input from NOR gate 1130 through inverter 1132. NOR gate 1130 also receives an input from NAND gate 1098 (FIG. 35A) through an inverter 1134. The output of NOR gate 1128 is applied to the shift out terminals of FIFOs 1042, 1044, 1046 and 1048 to shift the data into multiplexers 1050, 1052, 1054, 1056, 1058, 1060, 1062 and 1064.

FIFOs 1066, 1068, 1070 and 1072 are interconnected to NAND gate 1136. NAND gate 1136 functions to test the input ready on the FIFOs 1066, 1068, 1070 and 1072 similar to that of NAND gate 1116. The output of NAND gate 1136 is applied to NOR gate 1138 and NOR gate 1130. The output of NOR gate 1138 is applied to the gate 1126, which together with the application of the output of inverter 1124, NOR gate 1130 and the timing signal CLK11 generates an output signal applied to the shift in terminals of FIFOs 1066, 1068, 1070 and 1072 through an inverter 1140.

FIFOs 1066, 1068, 1070 and 1072 are interconnected to a NAND gate 1142, whose output is applied to the computer 60. The function of NAND gate 1142 is to generate a signal to the computer 60 indicating that the FIFOs 1066, 1068, 1070 and 1072 are loaded and the data is ready to be shifted out. The computer 60 then sends a shift out command, SO, which is applied to the shift out terminals of the FIFOs 1066, 1068, 1070 and 1072. The output of the FIFOs 1066, 1068, 1070 and 1072 is in the form of a 16 bit parallel word to the computer 60 applied through the hex drivers 1073–1088.

Figure 36:
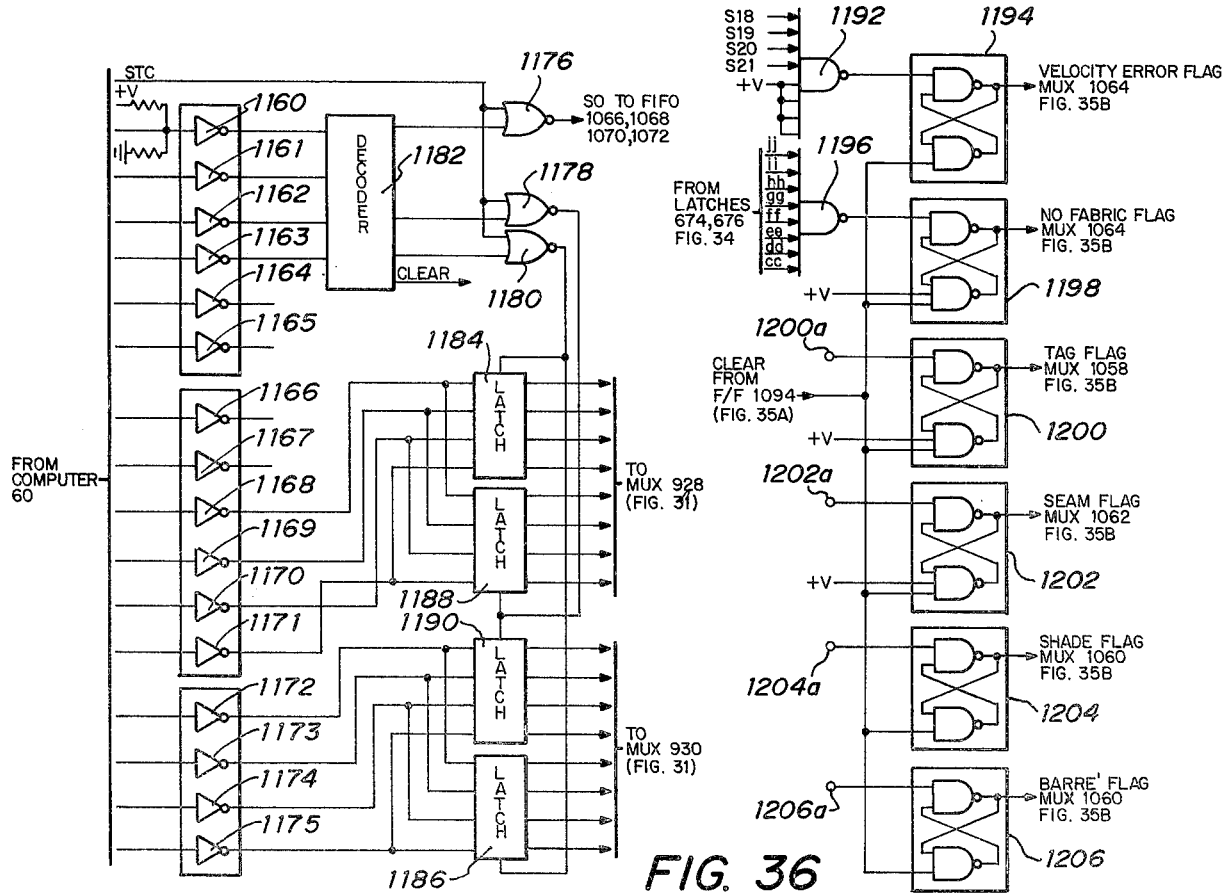
FIG. 36 is a detailed schematic diagram of a portion of the computer interface circuitry shown in block diagram of FIG. 16.

Referring to FIG. 36, the remaining portion of the schematic circuitry comprising the computer interface 368 (FIG. 16) is illustrated. A 16 bit parallel word is inputted from the computer 60 to the computer interface circuitry 368 (FIG. 16) through hex inverters 1160–1175. The STC strobe signal is applied from the computer 60 to NOR gates 1176, 1178 and 1180. The upper 4 bits of the 16 bit word from the computer 60 are applied to a decoder 1182. Decoder 1182 is a BCD decimal decoder and may comprise, for example, a 7442 I/C. The output of decoder 1182 is applied to NOR gates 1176, 1178 and 1180. The output of NOR gate 1176 generates the shift out, SO, signal, which is applied to the FIFOs 1066, 1068, 1070 and 1072 of the computer interface circuitry shown in FIG. 35B.

The lower 8 bits of the 16 bit word from the computer 60 are applied through inverters 1168–1175 to latches 1184, 1186, 1188 and 1190. Latches 1184 and 1186 comprise the latch block 528 identified in the block diagram of FIG. 18 and referred to in FIG. 31. Latches 1188 and 1190 correspond to the latch lock 530 identified in FIG. 18 and referred to in FIG. 31. Latches 1184, 1186, 1188 and 1190 may comprise, for example, 74175 I/Cs. The data input from the computer 60 to the latches 1184, 1186, 1188 and 1190 represent the positive and negative offset values supplied from the computer software depending upon the type of fabric being inspected. The output of NOR gate 1178 is applied to latches 1188 and 1190 to clock the positive offset values to the multiplexers 928 and 930 (FIG. 31). The output of NOR gate 1180 is applied to latches 1184 and 1186 to clock the negative offset values to the multiplexers 928 and 930 (FIG. 31).

FIG. 36 also illustrates the circuitry for setting the various flag bits for input into the multiplexers 1058, 1060, 1062 and 1064 for strobing into the three header words. The timing signals S18–S21 are applied through NAND gate 1192 which applies its output to a latch 1194. The output of latch 1194 indicates a velocity error and is applied to the multiplexer 1064 (FIG. 35B). Once the system has reached the proper velocity, the error flag for velocity will no longer be input into the multiplexer 1064.

The output from latches 674 and 676 (FIG. 34) along signal lines cc–jj are applied to NAND gate 1196, whose output is applied to a latch 1198. The output of latch 1198 applies the flag indicating that no fabric is passing through the inspection head assembly 50 to the multiplexer 1064 (FIG. 35B).

The clear signal generated by flip-flop 1094 (FIG. 35A) is applied to each of the latches 1200, 1202, 1204 and 1206. The output of latch 1200 indicates a tag flag and is applied to the multiplexer 1058. The output of latch 1202 indicates a seam flag and is applied to the multiplexer 1062. The output of latch 1204 is applied to the multiplexer 1060 of FIG. 35B, and indicates that a shade flaw has been detected. The output of latch 1206 is applied to the multiplexer 1060 and indicates that a barre flaw has been detected. The input to latches 1200, 1202, 1204 and 1206 is supplied at terminals 1200a, 1202a, 1204a and 1206a from hardware switch closures. For example, the output of the microswitch 274 of the seam detector assembly 146 (FIG. 9) is applied to terminal 1202a to set the latch 1200. Each time data is sent to the computer 60, the clear signal from the flip-flop 1094 is applied to the latches 1194, 1198, 1200, 1202, 1204 and 1206 to clear the latch.

CONTROL AND TIMING CIRCUITRY

Figure 37:
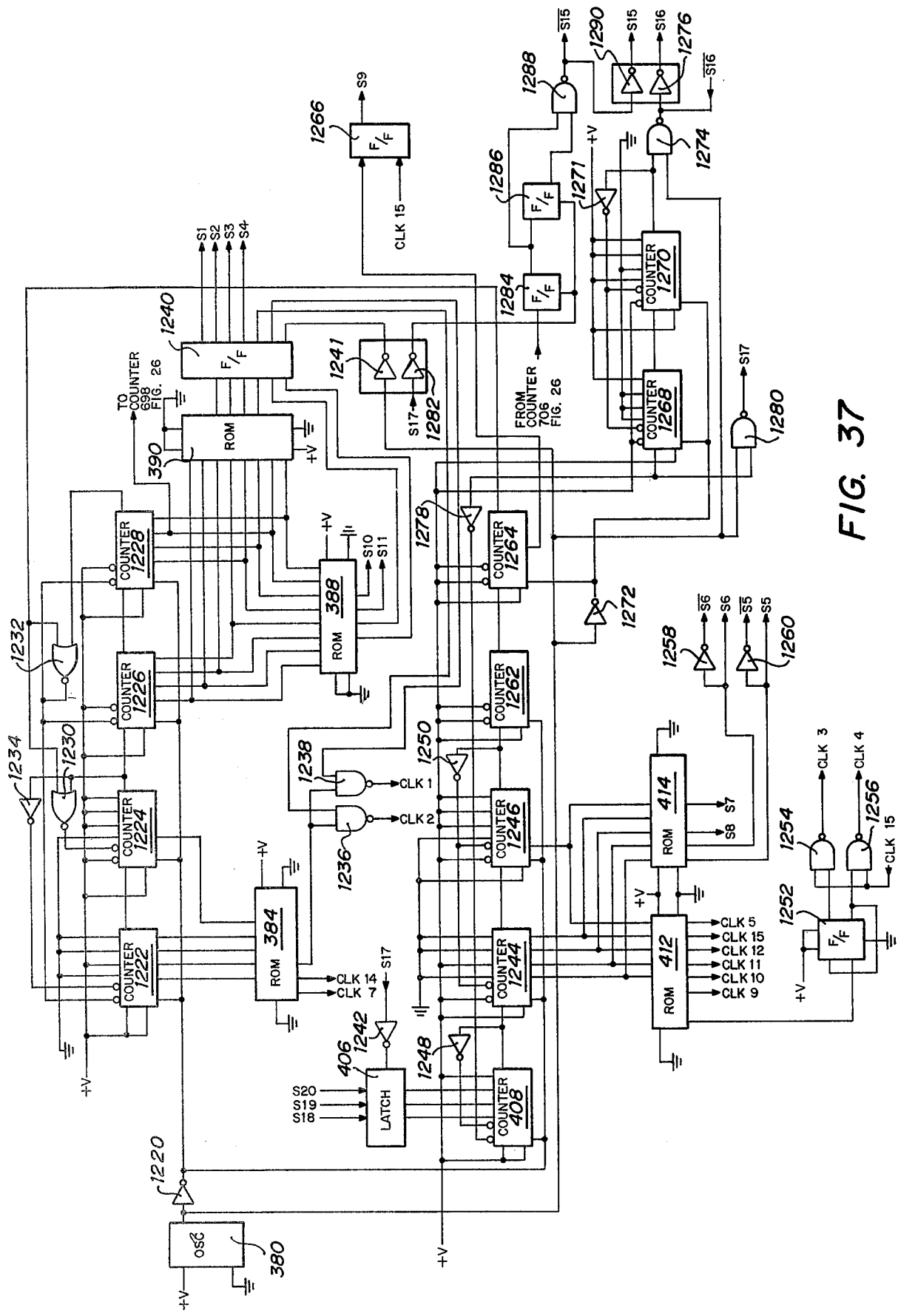
FIG. 37 is a detailed schematic diagram of a portion of the control and timing circuitry shown in block diagram of FIG. 16.

Referring to FIG. 37, a schematic diagram of the control and timing circuitry of the block diagram of FIG. 17 is illustrated. Like numerals are utilized for like and corresponding components identified in the block diagram of FIG. 17. The clock oscillator 380 operates at a frequency of 6.912 MHz and supplies an output through inverter 1220 to counters 1222, 1224, 1226 and 1228. Counters 1222, 1224, 1226 and 1228 are 4 bit counters and may comprise, for example, 74163 I/Cs. The counters 1222 and 1224 correspond to the counter block 382 (FIG. 17) and perform a divide by 30 function of the basic clock oscillator frequency. Counters 1226 and 1228 correspond to the counter block 386 (FIG. 17) and perform the divide by 256 function to provide the timing signals for each of the 256 cells within a three camera group. Associated with the counters 1222, 1224, 1226 and 1228 are NOR gates 1230 and 1232 and an inverter 1234.

The output of counters 1222 and 1224 are applied to a read only memory 384. Read only memory 384 may comprise, for example, an HM 7603 I/C. Th output of read only memory 384 generates the CLK7 and CLK14 timing signals. The output of read only memory 384 is also applied to NAND gates 1236 and 1238, which generate the CLK2 and CLK1 timing signals.

The output of counters 1226 and 1228 are applied to a read only memory 390. Read only memory 390 may comprise, for example, a 1024 I/C. The output of read only memory 390 is applied to a hex type D flip-flop 1240, whose output generates the S1, S2, S3 and S4 timing signals. Flip-flop 1240 may comprise, for example, a 74174 I/C. The output of flip-flop 1240 is also applied to NAND gates 1236 and 1238.

The output of counters 1226 and 1228 are also applied to a read only memory 388. Read only memory 388 may comprise, for example, a 1024 I/C. The output of read only memory 388 generates the S10 and S11 timing signals, and is also applied to the flip-flop 1240. Counter 1228 also generates an output to the counter 698 (FIG. 26).

The latch 406 receives the S18, S19 and S20 timing signals generated by the velocity correction circuitry and also receives the S17 timing signal through an inverter 1242. The output of latch 406 is applied to a counter 408, which performs a divide by "N" function depending upon the velocity correction code supplied to the latch 406. The division may be by a factor from 1 to 7 depending upon the velocity correction code. The output of counter 408 is applied to a counter 1244, which is interconnected to a counter 1246. Counters 1244 and 1246 comprise the counter block 410 (FIG. 17). Counters 1244 and 1246 perform a divide by 30 function, having their outputs applied to read only memories 412 and 414. Associated with counters 408, 1244 and 1246 are inverters 1248 and 1250. Counters 408, 1244 and 1246 are 4 bit counters and may comprise, for example, 74163 I/Cs.

The output of counters 1244 and 1246 represents the corrected cell time and is applied to read only memories 412 and 414. Read only memories 412 and 414 may comprise, for example, HM7603 I/Cs. The output of read only memory 412 generates the clock 5, 9, 10, 11, 12 and 15 timing signals. The output of read only memory 412 is also applied to a flip-flop 1252, whose output is applied to NAND gates 1254 and 1256. NAND gates 1254 and 1256 also receive the CLK15 timing signal and generate the CLK3 and CLK4 timing signals. The output of read only memory 414 generates the S5, S6, S7 and S8 timing signals. The output of read only memory 414 through inverters 1258 and 1260 generates the $\overline{S6}$ and $\overline{S5}$ timing signals.

The output of counter 1246 is also applied to a counter 1262, whose output is applied to a counter 1264. Counters 1262 and 1264 are 4 bit counters and may comprise, for example, 74163 I/Cs. Counters 1262 and 1264 comprise the counter block 416 (FIG. 17) and form a divide by 256 function. The output of counter 1264 is applied to a flip-flop 1266, which also receives the CLK15 timing signal to generate the S9 timing signal.

The output of counter 1264 is also applied to a counter 1268, which is interconnected to a counter 1270. Counters 1268 and 1270 comprise the counter block 420 (FIG. 17). Counters 1268 and 1270 are 4 bit counters and may comprise, for example, 74163 I/Cs. Counters 1268 and 1270 receive the output from the oscillator 380 through an inverter 1272. The output of counter 1270 is applied to a NAND gate 1274 and through an inverter 1271 to counter 1268. NAND gate 1274 generates the $\overline{S16}$ timing signal and through inverter 1276 generates the S16 timing signal. The output of counter 1268 is applied through an inverter 1278 to the counter 408 and to a NAND gate 1280 which generates the S17 timing signal.

The S17 timing signal is applied to an inverter 1282, whose output is applied to a flip-flop 1284. The output of flip-flop 1284 is applied to a flip-flop 1286 and a NAND gate 1288. The output of flip-flop 1286 is also applied to NAND gate 1288 to generate the $\overline{S15}$ timing signal and through inverter 1290 to generate the S15 timing signal.

Figure 38:
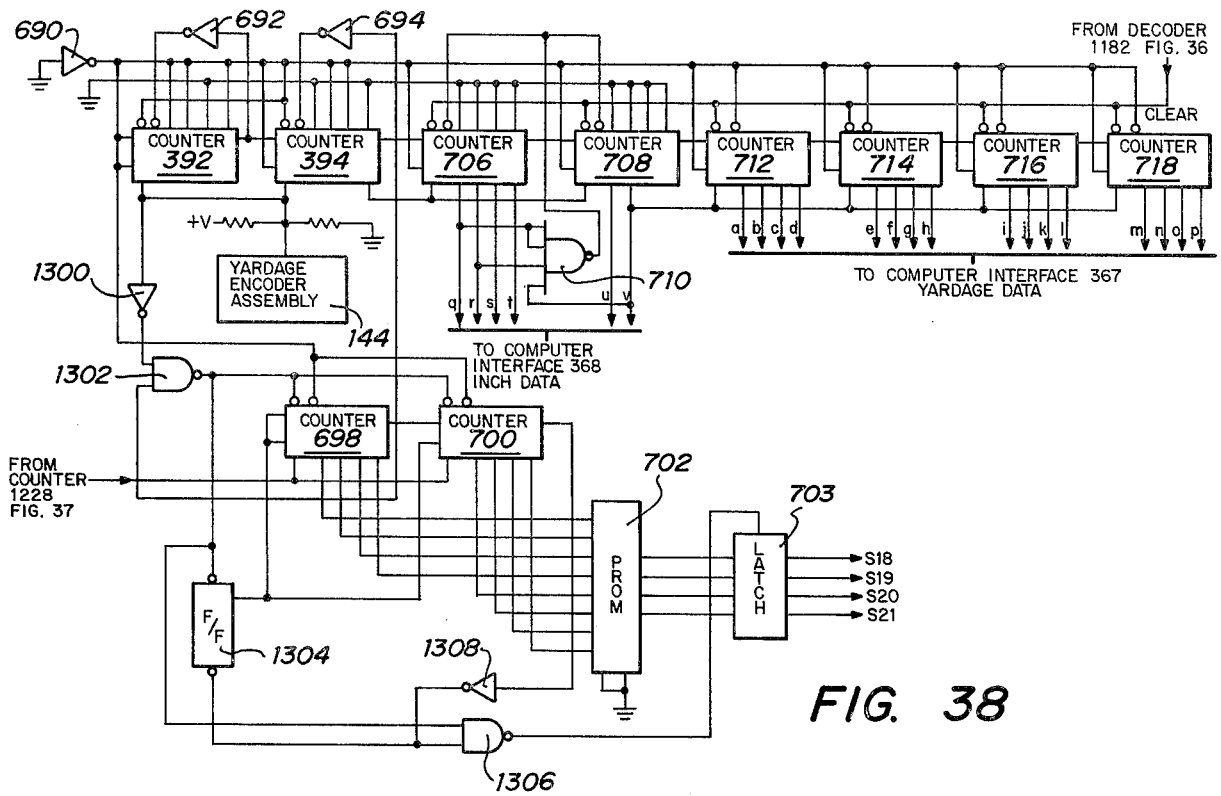
FIG. 38 is a detailed schematic diagram of the velocity correction circuitry shown in block diagram of FIG. 26.

Referring to FIG. 38, the remaining circuitry comprising the control and timing circuitry 360 (FIG. 16) is illustrated. FIG. 38 is a schematic diagram corresponding to the velocity correction circuitry shown in the block diagram of FIG. 26. The velocity correction circuitry corresponds to the yardage encoder assembly 144, counter blocks 392, 394, 396, 398 and 400 and the read only memories 402 and 404 of the block diagram of FIG. 17. The output of the yardage encoder assembly 144 is applied to counters 392 and 394. Counter 392 performs a divide by 5 function and counter 394 provides a divide by 10 function to divide the 600 pulse per foot output of the yardage encoder assembly 144 by a factor of 50. The output of counters 392 and 394 representing a signal of one pulse per inch is applied to counters 706 and 708. Counters 706 and 708 correspond to the counter block 396 (FIG. 17) and perform a divide by 36 function. The output of counters 706 and 708 represent the number of inches of the fabric who passing through the inspection head assembly 50 and is applied to the multiplexers 1050, 1052 and 1054 (FIG. 35B) along signal lines q–v.

The output of counter 708 is also applied to counters 712, 714, 716 and 718. Counters 712, 714, 716 and 718 correspond to the counter block 398 (FIG. 17) and provide an output indicating yardage data to the multiplexers 1050, 1052, 1054, 1056, 1058, 1060, 1062 and 1064 (FIG. 35B) along signal lines a–p.

The output of counter 392 is also applied through an inverter 1300 and NAND gate 1302 to counters 698 and 700. Counters 698 and 700 correspond to the counter block 400 (FIG. 17). Counters 698 and 700 count the actual scans per inch of fabric motion through the inspection head assembly 50 and provide an output to the programmable read only memory 702. Read only memory 702 corresponds to the read only memory blocks 402 and 404 (FIG. 17) and generates the velocity correction code, which is applied to the latch 703. Latch 703 generates the S18, S19, S20 and S21 timing signals. The S18, S19 and S20 timing signals are applied to the latch 406 (FIG. 37).

The output of NAND gate 1302 is also applied to a flip-flop 1304 and a NAND gate 1306. NAND gate 1306 receives an output from flip-flop 1304 and an output from counter 700 through an inverter 1308. The output of NAND gate 1306 is applied to the latch 703. Each of the counters in the velocity correction circuitry of FIG. 38 is a 4 bit counter and may comprise, for example, 74161 I/Cs. The read only memory 702 may comprise, for example, an 1024 I/C. The latch 703 is a 4 bit latch and may comprise, for example, a 74175 I/C.

CONTROL PANEL CIRCUITRY

Figure 39:
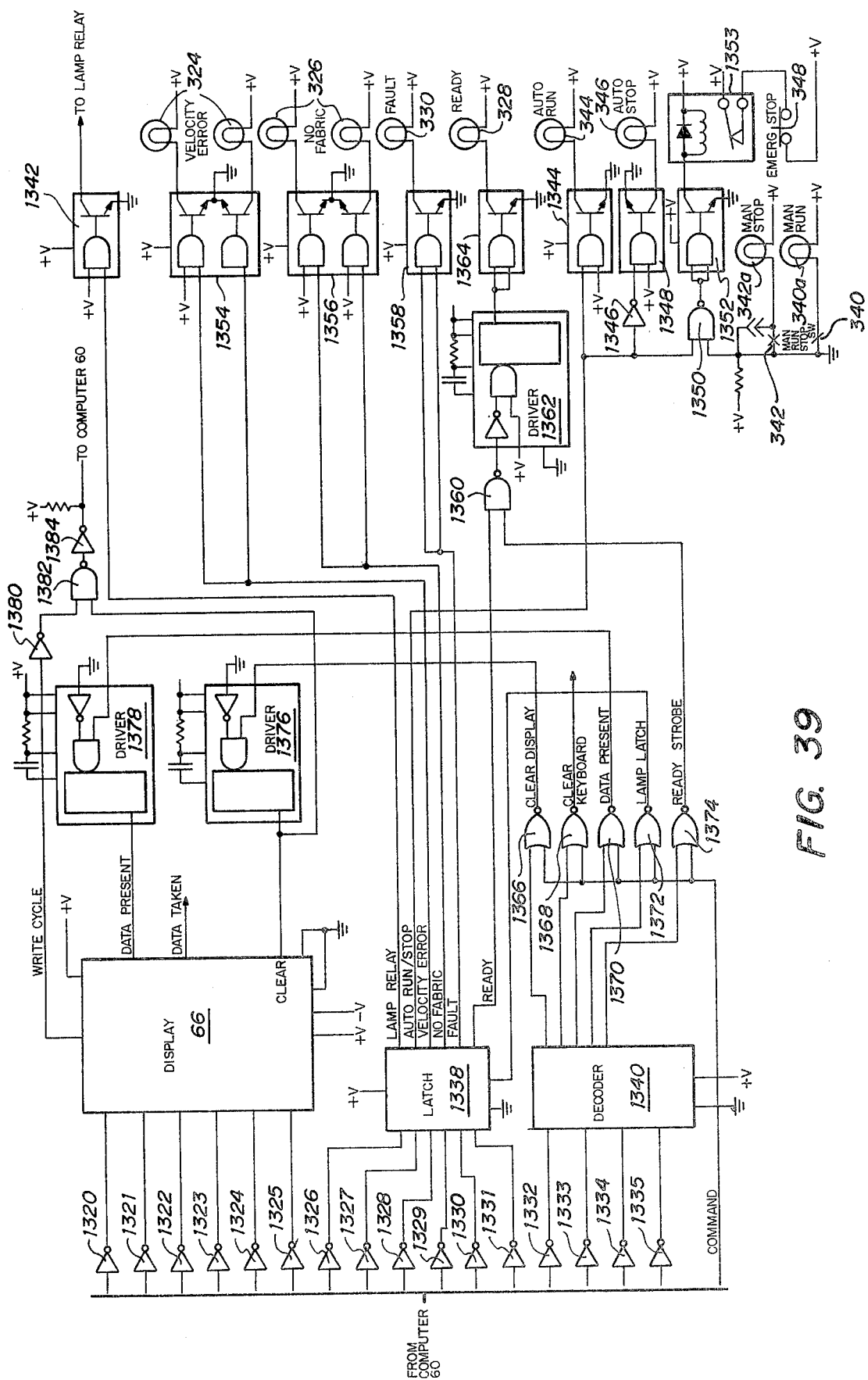
FIG. 39 is a detailed schematic diagram of a portion of the control panel display circuitry.

FIG. 39 illustrates a portion of the schematic diagram corresponding to the circuitry control panel 64 (FIG. 1). The data entered into the control panel through the key sets 68 and 69 is applied from the computer 60 through hex inverters 1320–1325 to the display 66. The computer 60 also applies an input through hex inverters 1326–1331 to a latch 1338. Latch 1338 may comprise, for example, a 74174 I/C. Latch 1338 generates the lamp relay output signal which is applied to a driver 1342 for application to the lamp relay. Latch 1338 also generates the auto run/stop signal. The auto run/stop signal is applied to a driver 1344, which illuminates the "AUTO RUN" indicator 344 (FIG. 15). The auto run/stop signal is also applied through an inverter 1346 to a driver 1348, which illuminates the "AUTO STOP" indicator 346 (FIG. 15). The auto run/stop signal is also applied to a NAND gate 1350, which is interconnected to a driver 1352. Driver 1352 is interconnected to an auto run/stop relay 1353. The emergency stop switch 348 is also interconnected to the relay 1353. Interconnected to NAND gate 1350 are the lamp indicators 342a for the manual stop push button switch 342 and lamp indicator 340a for the manual run push button switch 340.

The output of latch 1338 also generates the velocity error signal, which is applied to a driver 1354 to illuminate the "VELOCITY ERROR" indicator 324 (FIG. 15). Latch 1338 also generates the no fabric signal, which is applied to a driver 1356 to illuminate the "NO FABRIC" indicator 326 (FIG. 15). The fault signal is also generated by latch 1338 and is applied to a driver 1358 to illuminate the "FAULT" indicator lamp 330 (FIG. 15). The ready signal generated by latch 1338 is applied through a NAND gate 1360 to a driver 1362, whose output is applied to a driver 1364 to illuminate the "READY" indicator lamp 328.

Data from the computer 60 is also applied through hex inverters 1332–1335 to a decoder 1340. The decoder 1340 is a BCD decimal decoder and may comprise, for example, a 7422 I/C. The outputs of decoder 1340 are applied to NOR gates 1366, 1368, 1370, 1372 and 1374. Also applied to NOR gates 1366–1374 is a command signal generated by the computer 60. The output of NOR gate 1366 representing the clear display signal is applied to a driver 1376, whose output is applied to the clear terminal of the display 66. Driver 1376 functions to clear the display 66. The output of NOR gate 1368 generates the clear keyboard signal which is applied to the keyboard circuitry of the control panel 64. The output of NOR gate 1370 generates the data present signal, which is applied to a driver 1378. Driver 1378 indicates to the display 66 that new character data is available and that this new data is desired to be displayed. After receipt of the new character data, the display 66 generates a write cycle signal, which through inverter 1380 is applied to NAND gate 1382. NAND gate 1382 also receives the clear signal and is applied to the computer 60 through inverter 1384. This clear signal applied to the computer 60 indicates that the display 66 has written the new character and is ready to accept new character data.

The NOR gate 1372 generates the lamp latch signal, which is used to clock the latch 1338. The ready strobe signal is generated by the NOR gate 1374 and is applied to the NAND gate 1360. The lamp drivers of the control panel display are dual peripheral drivers and may comprise, for example, 75452 BV drivers. The drivers 1362, 1376 and 1378 are dual retriggerable one shots with clear and may comprise, for example, 74123 I/Cs.

Referring to FIG. 40, the keyboard and related circuitry of the control panel 64 (FIG. 1) is illustrated. The keyboard 1390 includes the key sets 68 and 69 (FIG. 15) and the associated diode matrix switches associated with the push button switches comprising the key sets 68 and 69. Each time a push button switch is depressed on the keyboard 1390, an output signal is applied along signal line 1392 through inverter 1394 to a driver 1396. Driver 1396 is a dual retriggerable one shot and may comprise, for example, a 74123 I/C. The output of driver 1396 is applied to a NOR gate 1398 whose output is applied to NOR gates 1400 and 1402. The output of NOR gate 1402 is applied through a NOR gate 1404 and inverter 1406 to latches 1408 and 1410. Driver 1396, NOR gates 1398, 1400, 1402 and 1404 function as a timing generator to generate a pulse to strobe the data in from the keyboard once a key has been depressed into the latches 1408 and 1410. The timing signal is applied to latches 1408 and 1410 to prevent the latches 1408 and 1410 from receiving multiple entries from the keyboard 1390. Latches 1408 and 1410 may comprise, for example, 74175 I/Cs.

The clear keyboard signal generated by the NOR gate 1368 (FIG. 39) is applied to a NOR gate 1412. The data taken signal generated by the display 66 is applied through an inverter 1414 to NOR gate 1412. The output of NOR gate 1412 is applied to latches 1408 and 1410 to clear the data from the latches 1408 and 1410. An output from the latch 1410 is applied through an inverter 1422 to apply a device flag signal to the computer 60.

Referring to FIG. 41, the circuitry corresponding with the lamp power push button switch 334 and lamp start push button switch 336, their associated indicators and the lamp on indicator 338 is illustrated. The lamp power switch 334 is interconnected to a driver 1424, whose output illuminates the "LMP PWR" indicator 334a. A signal from the lamp monitor which monitors the condition of the lamp is applied through an inverter 1426 to a driver 1428, whose output illuminates the "LMP ON" indicator 338. The output of inverter 1426 is also applied to a NAND gate 1430 to the driver 1424. The output of NAND gate 1430 is also applied through inverters 1432 and 1434 to the computer 60 to indicate the lamp status. The start lamp switch 336 is interconnected to driver 1428 and the "LAMP START" indicator lamps 336a. The "SENSOR ON" push button switch 332 is interconnected to an associated indicator lamp 332a, which is illuminated when the "SENSOR ON" push button 332 is depressed.

DEFECT OUTPUT REPORT

The defect output report generated by the fabric inspection system of the present invention is output through the printer 74 under the control of the computer 60. There are typically six types of defects which are identified by the system. A warp defect is a defect running along the length of the fabric web. In the preferred embodiment, a warp defect is catagorized as being narrow if it is less than three inches wide, and is catagorized as being wide if it is greater than three inches wide. A second type of defect is a fill defect, which is a defect running across the width of the fabric web. A narrow fill defect is one that is less than three inches across the fabric web and a wide fill defect is one that is greater than three inches long across the fabric web. Isolated defects are also identified such as knots, oil spots and those defects having no definite warp or fill orientation. The sixth type of defect is a special defect which includes tags, barre and shade defects.

A typical output report is illustrated at Table 1 below. The operator information input through the central panel 64 representing the bale number, loom number, fabric web width and style are printed at the top of the report. The defect map is divided into six columns corresponding to the six types of defects. The six defects are: narrow warp (NAR-WARP), narrow fill (NAR-FILL), wide warp (WID-WARP), wide fill (WID-FILL), isolated defect (ISOLATED) and special defect (SPECIAL). Below each of the six types of defects, the report indicates the yardage at which a defect was detected and the grade points assigned by the computer software to each of the defects detected. For example, under the category of narrow fill defects, at yard 30 a defect was detected and assigned four grade points. Similarly, at yard 45 a narrow fill defect was detected and assigned two grade points. In the isolated defect catagory, at yard 43 a defect was detected and assigned two grade points.

When a seam is detected, a summary quality report of the fabric inspected prior to the detection of the seam is printed. In the table below the report indicates that a seam was detected at yard 96. For each of the six defect catagories the total number of grade points are summed and a quality rating is given to the fabric. For example, the total number of grade points for the narrow fill defects during the first 96 yards of the fabric inspected was 43 which was assigned a quality factor of 13. The total number of grade points for the isolated defects was 20 and the fabric was assigned a quality factor of 8. Also printed in the output report is the minimum and maximum width of the fabric over the 96 yards inspected. The report below indicates that the minimum width was 45 inches and the maximum width was 45.25 inches. An overall quality determination of the fabric is then printed. The table below indicates that the fabric was rated second quality having 21 total defects and a total of 63 grade points. The average number of grade points per yard inspected was 0.66 points.

TABLE 1

| BALE | 1 | | | | | |
|---|---|---|---|---|---|---|
| LOOM | 32767 | | | | | |
| WIDTH | 45.00 | | | | | |
| STYLE | 5436 | | | | | |
| DEFECT | NAR-WARP | NAR-FILL | WID-WARP | WID-FILL | ISOLATED | SPECIAL |
| MAP | YRD-PTS | YRD-PTS | YRD-PTS | YRD-PTS | YRD-PTS | YRD-TYPE |

TABLE 1-continued

| BALE | 1 | | | | | |
|---|---|---|---|---|---|---|
| LOOM | 32767 | | | | | |
| WIDTH | 45.00 | | | | | |
| STYLE | 5436 | | | | | |
| DEFECT MAP | NAR-WARP YRD-PTS | NAR-FILL YRD-PTS | WID-WARP YRD-PTS | WID-FILL YRD-PTS | ISOLATED YRD-PTS | SPECIAL YRD-TYPE |
| | | 2-2 | | | | |
| | | 2-2 | 6-1 | | | |
| | | 20-4 | | | | |
| | | 25-4 | | | | |
| | | 30-4 | | | | |
| | | | 32-4 | | | |
| | | | 37-2 | | | |
| | | 39-4 | | | | |
| | | 40-4 | | | | |
| | | | 43-2 | | | |
| | | 45-2 | | | | |
| | | 48-4 | | | | |
| | | 57-4 | | | | |
| | | 61-4 | | | | |
| | | | 68-2 | | | |
| | | 70-4 | | | | |
| | | | 82-2 | | | |
| | | | 89-3 | | | |
| | | | 93-4 | | | |
| | | 95-1 | | | | |
| SEAM 96 | QTY-PTS 0-0 | QTY-PTS 13-43 | QTY-PTS 0-0 | QTY-PTS 0-0 | QTY-PTS 8-20 | QTY 0 |
| WIDTH | | MINIMUM 45.00 | | MAXIMUM 45.25 | | |
| 2ND QUALITY | | DEFECTS 21 | | POINTS 63 | | AVE PTS .66 |

The source files for accomplishment of operation of the present system 2105 MX Hewlett Packard computer is set forth below in Hewlett-Packard assembly language. Table 2 is a source file to generate the disk for the fabric inspection system. Table 3 is the source file for the fabric inspection control monitor. Table 4 is the source file for the keyboard and control panel of the fabric inspection system. Table 5 is the source file for the fabric inspection preprocessor driver. Table 6 is the source file for defect grading. Table 7 is the source file for the fabric inspection printer driver. Table 8 is the source file for the fabric inspection message formater.

TABLE 2

```
:LI,S,1,SIMAG

0001    ASMB,L,C
0002          HED FABRIC INSPECTION SYSTEM GENERATER
0003    *
0004          NAM IMAGE,3
0005          ENT IMAGE
0006          EXT EXEC
0007    *
0008    *     ROUTINE TO FORMAT SYKES 7250 DISKS
0009    *     FOR BOOTSTRAPING STAND ALONE LOADER
0010    *     GENERATED PROGRAMS USING SYKES IBL
0011    *
0012    *     DAVID GATES
0013    *
0014    *     (4/20/76)
0015    *
0016    IMAGE JSB EXEC       FILE?
0017          DEF *+5
0018          DEF .+2
0019          DEF B401
0020          DEF MES1-
0021          DEF .+3
0022          JSB EXEC       GET NAME
0023          DEF *+5
0024          DEF .+1
0025          DEF B401
0026          DEF NAME
0027          DEF .-5
0028          CLA            DISABLE :SS
0029          LDB SSFLG
0030          JSB EXEC
0031          DEF *+2
0032          DEF N19
0033          JSB EXEC       SUBCHANNEL=0
```

```
0034            DEF *+4
0035            DEF D23
0036            DEF UPPER
0037            DEF .+0
0038            JSB EXEC           FILE SEARCH
0039            DEF *+4
0040            DEF D18
0041            DEF NAME
0042            DEF SIZE
0043            LDA SIZE
0044            CMA,INA,SZA
0045            JMP FOUND
0046            JSB EXEC           NOT FOUND
0047            DEF *+5
0048            DEF .+2
0049            DEF B401
0050            DEF ERR1
0051            DEF .+5
0052            JMP STOP
0053    FOUND   STA SIZE
0054            LDA B
0055            ADA .-1
0056            LDA A,I
0057            AND B177
0058            CPA .+3
0059            JMP LEGAL
0060            JSB EXEC           ILLEGAL TYPE
0061            DEF *+5
0062            DEF .+2
0063            DEF B401
0064            DEF ERR2
0065            DEF .+6
0066            JMP STOP
0067    LEGAL   LDA B,I            GET TRACK/SECTOR
0068            AND B377
0069            STA SCT
0070            LDA B,I
0071            ALF,ALF
0072            AND B377
0073            STA TRK
0074            ADB .+2            GET PROGRAM FWA
0075            LDA B,I
0076            STA FWAP
0077            CMA,INA            GET - # WORDS
0078            INB
0079            ADA B,I
0080            CMA,INA
0081            STA NLOCP
0082            INB                GET BASE PAGE FWA
0083            LDA B,I
0084            STA FWABP
0085            CMA,INA            GET - # WORDS
0086            INB
0087            ADA B,I
0088            CMA,INA
0089            STA NLOCB
0090            INB                GET ENTRY POINT
0091            LDA B,I
0092            STA ENTRY
0093            JSB EXEC           OPTIONS?
0094            DEF *+5
0095            DEF .+2
0096            DEF B401
0097            DEF MESS
0098            DEF .+4
0099            JSB EXEC           GET ANSWER
0100            DEF *+5
0101            DEF .+1
0102            DEF B401
0103            DEF NAME
0104            DEF .+1
0105            LDA NAME
0106            CPA YES
0107            RSS
0108            JMP NONE
0109            CLF 0              GET OPTIONS
```

```
0110            HLT 1
0111            LIA 1
0112            STA AOP
0113            HLT 2
0114            LIA 1
0115            STA BOP
0116            STF 0
0117    NONE    JSB EXEC
0118            DEF *+4
0119            DEF D23
0120            DEF LOWER
0121            DEF .+1
0122            JSB EXEC        STORE DISK LOADER
0123            DEF *+7
0124            DEF .-2
0125            DEF B103
0126            DEF DLOAD
0127            DEF D256
0128            DEF DTRK
0129            DEF DSCT
0130            ISZ DSCT
0131            ISZ DSCT
0132    TRANS   JSB EXEC        SUBCHANNEL=0
0133            DEF *+4
0134            DEF D23
0135            DEF UPPER
0136            DEF .+0
0137            JSB EXEC        GET SOURCE BUFFER
0138            DEF *+7
0139            DEF .-1
0140            DEF B103
0141            DEF BUFF
0142            DEF D1664
0143            DEF TRK
0144            DEF SCT
0145            JSB EXEC        SUBCHANNEL=1
0146            DEF *+4
0147            DEF D23
0148            DEF LOWER
0149            DEF .+1
0150            JSB EXEC        STORE BUFFER FULL
0151            DEF *+7
0152            DEF .-2
0153            DEF B103
0154            DEF BUFF
0155            DEF D1664
0156            DEF DTRK
0157            DEF DSCT
0158            LDA SIZE        FINISHED ?
0159            ADA D13
0160            SSA,RSS
0161            JMP DONE
0162            STA SIZE
0163            ISZ TRK
0164            ISZ DTRK
0165            JMP TRANS
0166    DONE    JSB EXEC        IMAGE STORED
0167            DEF *+5
0168            DEF .+2
0169            DEF B401
0170            DEF MESS
0171            DEF .+6
0172    STOP    JSB EXEC        RETURN TO DOS
0173            DEF *+2
0174            DEF .+6
0175    *
0176    *       DISK RESIDENT LOADER FOR FIS BOOTSTRAP
0177    *
0178    *       ORG 154008
0179    DLOAD   OCT 103100      CLF 0
0180            OCT 106700      CLC 0
0181            OCT 063444      LDA CLEAR
0182            OCT 017440      JSB CMD
0183            OCT 063445      LDA TSEL
0184            OCT 017440      JSB CMD
0185            OCT 063446      LDA SREAD
```

```
0186        OCT 017440       JSB CMD
0187        OCT 063447       LDA RMODE
0188        OCT 102613       OTA FLOP
0189        OCT 102313  LOOP SFS FLOP
0190        OCT 027412       JMP *-1
0191        OCT 102513       LIA FLOP
0192        OCT 103713       STC FLOP,C
0193        OCT 001727       ALF,ALF
0194        OCT 102313       SFS FLOP
0195        OCT 027417       JMP *-1
0196        OCT 102413       MIA FLOP
0197        OCT 103713       STC FLOP,C
0198        OCT 173452       STA KORE,I
0199        OCT 037452       ISZ KORE
0200        OCT 037453       ISZ KNTR
0201        OCT 027413       JMP LOOP
0202        OCT 063450       LDA STCMD
0203        OCT 102613       OTA FLOP
0204        OCT 102513       LIA FLOP
0205        OCT 013451       AND ERROR
0206        OCT 002002       SZA
0207        OCT 102011       HLT 11B
0208        OCT 063444       LDA CLEAR
0209        OCT 017440       JSB CMD
0210        OCT 127454       JMP START,I
0211        OCT 000000  CMD  NOP
0212        OCT 102613       OTA FLOP
0213        OCT 103713       STC FLOP,C
0214        OCT 127440       JMP CMD,I
0215        OCT 100020  CLEAR
0216        OCT 000420  TSEL
0217        OCT 002020  SREAD
0218        OCT 006010  RMODE
0219        OCT 000100  STCMD
0220        OCT 120000  ERROR
0221        OCT 000002  KORE
0222        OCT 177500  KNTR DEC -192
0223        OCT 000002  START
0224        BSS      19
0225    *
0226    *   DISK RESIDENT PROGRAM LOADER FOR FIS BOOTSTRAP
0227    *
0228    *   ORG 2B
0229  PLOAD OCT 060121       LDA FWAP
0230        OCT 070126       STA CORE
0231        OCT 060122       LDA NLOCP
0232        OCT 070127       STA CNTP
0233        OCT 060142       LDA PTRK
0234        OCT 001727       ALF,ALF
0235        OCT 050136       IOR B20
0236        OCT 070130       STA TSEEK
0237        OCT 060143       LDA PSCT
0238        OCT 001727       ALF,ALF
0239        OCT 030136       IOP B20
0240        OCT 070131       STA SREAD
0241        OCT 014060       JSB DISK
0242        OCT 060124       LDA NLOCB
0243        OCT 003007       CMA,INA,SZA,RSS
0244        OCT 024056       JMP RUN
0245        OCT 060122       LDA NLOCP
0246        OCT 003004       CMA,INA
0247        OCT 006400       CLB
0248        OCT 100400       DIV D64
0249        OCT 000140
0250        OCT 006002       SZB
0251        OCT 002004       INA
0252        OCT 040143       ADA PSCT
0253        OCT 040141       ADA N1
0254        OCT 006400       CLB
0255        OCT 100400       DIV D26
0256        OCT 000137
0257        OCT 002004       INA
0258        OCT 001727       ALF,ALF
0259        OCT 030136       IOP B20
0260        OCT 070130       STA TSEEK
0261        OCT 006004       INB
0262        OCT 060001       LDA 1
```

```
0263        OCT 002011       SLA,RSS
0264        OCT 002004       INA
0265        OCT 001727       ALF,ALF
0266        OCT 030136       IOR B20
0267        OCT 070131       STA SREAD
0268        OCT 060123       LDA FWABP
0269        OCT 070126       STA CORE
0270        OCT 060124       LDA NLOCB
0271        OCT 070127       STA CNTR
0272        OCT 014060       JSB DISK
0273        OCT 024146       JMP RUN
0274        OCT 000000
0275        OCT 000000  DISK NOP
0276        OCT 060130       LDA TSEEK
0277        OCT 014115       JSB CMD
0278        OCT 060131       LDA SREAD
0279        OCT 014115       JSB CMD
0280        OCT 060134       LDA READ
0281        OCT 102613       OTA FLOP
0282        OCT 102315  LOOP SFS FLOP
0283        OCT 024067       JMP *-1
0284        OCT 102513       LIA FLOP
0285        OCT 103713       STC FLOP,C
0286        OCT 001727       ALF,ALF
0287        OCT 102313       SFS FLOP
0288        OCT 024074       JMP *-1
0289        OCT 102413       MIA FLOP
0290        OCT 103713       STC FLOP,C
0291        OCT 170126       STA CORE,I
0292        OCT 024126       ISZ CORE
0293        OCT 034127       ISZ CNTR
0294        OCT 024067       JMP LOOP
0295        OCT 060133       LDA STAT
0296        OCT 102613       OTA FLOP
0297        OCT 102513       LIA FLOP
0298        OCT 010135       AND ERR
0299        OCT 002002       SZA
0300        OCT 102011       HLT 11B
0301        OCT 060132       LDA RESET
0302        OCT 014115       JSB CMD
0303        OCT 124060       JMP DISK,I
0304        OCT 000000  CMD  NOP
0305        OCT 102613       OTA FLOP
0306        OCT 103713       STC FLOP,C
0307        OCT 124115       JMP CMD,I
0308  FWAP  OCT 000000  FWAP
0309  NLOCP OCT 000000  NLOCP
0310  FWABP OCT 000000  FWABP
0311  NLOCB OCT 000000  NLOCB
0312  ENTRY OCT 000000  ENTRY
0313        OCT 000000  CORE
0314        OCT 000000  CNTR
0315        OCT 000000  TSEEK
0316        OCT 000000  SREAD
0317        OCT 100020  RESET
0318        OCT 000100  STAT
0319        OCT 000019  READ
0320        OCT 120000  ERR
0321        OCT 000020  B20
0322        OCT 000032  D26
0323        OCT 000100  D64
0324        OCT 177777  M1
0325        OCT 000001  PTRK
0326        OCT 000007  PSCT
0327  AOP   OCT 000000  AOP
0328  BOP   OCT 000000  BOP
0329        OCT 060144  RUN  LDA AOP
0330        OCT 064145       LDB BOP
0331        OCT 102100       STF 0
0332        OCT 124125       JMP ENTRY,I
0333        BSS 88
0334  *
0335  MES1  ASC 3,FILE?
0336  MES3  ASC 6,IMAGE STORED
0337  MES5  ASC 4,OPTIONS?
0338  ERR1  ASC 5,NOT FOUND
```

```
0339  ERR2  ASC  6,ILLEGAL TYPE
0340  LOWER ASC  3,IMAGE
0341  UPPER ASC  3,PN0000
0342  NAME  ASC  3,
0343  YES   ASC  1,YE
0344  TRK   NOP
0345  SCT   NOP
0346  SIZE  NOP
0347  DTRK  DEC  0
0348  DSCT  DEC  1
0349  SSFL6 OCT  231
0350  B103  OCT  103
0351  B177  OCT  177
0352  B377  OCT  377
0353  B401  OCT  401
0354  D13   DEC  13
0355  D18   DEC  18
0356  D23   DEC  23
0357  D256  DEC  256
0358  D1664 DEC  1664
0359  N19   DEC  -19
0360  BUFF  BSS  1664
0361  .     EQU  53B
0362  P     EQU  0B
0363  F     EQU  1B
0364        END  IMAGE
**** LIST END ****
```

TABLE 3

```
:LI,S,1,SMONT

0001  ASMB,L,C
0002        HED  FABRIC INSPECTION CONTROL MONITOR
0003        NAM  MONTR
0004        ENT  MONTR
0005        EXT  SCANR,BUSY1
0006        EXT  WRITE,.LIST
0007        ENT  SYSOP,WDOPR
0008        EXT  .SCAN,.GRAD
0009        EXT  .KEYS,BUSY3
0010        ENT  HSTAK,HSTNX
0011        ENT  HSTAV,HSTEN,#SEAM
0012        ENT  MAIN,KEYS,INIT
0013        EXT  LED,KEY,LITE,HIT
0014        EXT  CHIT,CIN,PSTAT
0015        EXT  PRTER,FISER
0016        ENT  IDLE,DPUG
0017        EXT  SOERR,HOEFP
0018  *
0019  *
0020  *
0021  *     FABRIC INSPECTION SYSTEM CONTROL MONITOR
0022  *     INITIATES BASE PAGE CONSTANTS AND TAKES
0023  *     OPERATOR INPUTS FROM KEYBOARD AND FROM
0024  *     SWITCH REGISTER FOR DEBUG
0025  *
0026  *
0027  *
0028  *     DAVID GATES
0029  *
0030  *     (11/5/76)
0031  *
0032  MONTR CLF  0          INTERRUPTS OFF
0033        STA  SYSOP      SYSTEM OPTIONS
0034        LDA  SCANR      SET UP TRAP CELLS
0035        STA  DVR10
0036        LDA  WRITE
0037        STA  DVR11
0038        LDA  HIT
0039        STA  DVR12
```

```
0040            LDA BPAGE
0041            LDB BPADP
0042            MVW #WORD       STORE BASE PAGE
0043    *
0044    *       RESTART SECTION
0045    *
0046    START   CLC 0           INITIATION PHASE
0047            STF 0           INTERRUPTS ON
0048            CLA
0049            STA SQERR
0050            STA HOERR
0051            STA HSERR
0052            OTA 1           CLEAR SWITCHES
0053            STA DBUG        PROGRAM DEBUG OFF
0054            STA INIT        PREPROCESSOR OFF
0055            JSB .SCAN
0056            JSB .GRAD
0057            JSB .LIST
0058            JSB .KEYS
0059    DEAD    LDA MES1        "FABRIC INSPECTION SYSTEM"
0060            LDB =D12
0061            JSB LED
0062            CLA
0063            STA CHIT
0064            CLA,INA
0065            STA DFLAG
0066    *
0067    *       MAIN POLING LOOP
0068    *
0069    MAIN    LDA KEYS        MAIN PROCESSING LOOP
0070            SZA,RSS         KEYBOARD INPUT READY?
0071            JMP SREG        NOP, CHECK SWITCHES
0072            LDA INIT
0073            SZA             PREPROCESSOR RUNNING
0074            JMP SREG        YES, CHECK SWITCH REGISTER
0075    *
0076            LDA PSTAT       PREPROCESSOR START UP
0077            ALF,SLA         LAMP POWER UP?
0078            JMP MAN         YEP
0079            LDA ERR3        "TURN ON LAMP"
0080            LDB .+6
0081            JSB LED
0082            CLA
0083            STA CHIT
0084    LON     LDA .+6         WAIT FOR LAMP POWER
0085            LDB .+1
0086            JSB LITE
0087            LDA PSTAT       GET LAMP STATUS
0088            ALF,SLA
0089            JMP MAN         POWER UP NOW
0090            LDA CHIT        REVERSE POLARITY?
0091            CPA .+5
0092            RSS
0093            JMP LON         NOP
0094            LDA .+1
0095            CLB
0096            STB CHIT
0097            JSB LITE        CHANGE LIGHT POLARITY
0098            JMP LON
0099    MAN     LDA PSTAT       MANUAL RUN ON?
0100            AND =B40000
0101            SZA
0102            JMP RUN         YEP, START PREPROCESSOR
0103            LDA ERR5        "TURN ON MANUAL RUN"
0104            LDB .+9
0105            JSB LED
0106    MON     LDA .+6         WAIT FOR MANUAL RUN
0107            LDB .+1
0108            JSB LITE        STROBE READY LIGHT
0109            LDA PSTAT
0110            AND =B40000
0111            SZA,RSS         ON YET?
0112            JMP MON         NOP
0113    RUN     JSB IDLE        SET UP INPUT
0114            CLA
0115            STA DFLAG
```

```
0116           JSB SCAN        START INSPECTOR
0117    *
0118    SREG   LIA 1           READ SWITCHES
0119           SSA             DEBUG REQUEST?
0120           STA DBUG        YEP, SAVE IT
0121           LDB DBUG
0122           SZB,RSS          DEBUG ACTIVE?
0123           JMP NOBUG       NOP
0124           SLA,RSS         DEBUG STOP REQUEST?
0125           JMP NOBUG       NOP
0126           LDA ERR7        "DEBUG TERMANITATED"
0127           LDB .+8
0128           JSB LED
0129           JMP STALL       YEP, STOP EVERTHING
0130    *
0131    NOBUG  LDA BUSY1       PREPROCESSOR BUSY?
0132           SZA
0133           HLT 0B          YEP, SHOULDN'T HAPPEN
0134           LDB INIT        SET AUTO RUN/STOP LIGHT
0135           SZB,RSS
0136           CCB
0137           LDA .+2
0138           JSB LITE
0139           LDA CHIT        GET KEYBOARD CHAR.
0140           CPA .+1         ENTER KEY HIT?
0141           JMP INPUT       YEP
0142           SZA,RSS         CHARACTER PRESENT?
0143           JMP CHECK       NOP, CHECK OTHER STUFF
0144           CPA .+5         REVERSE POLARITY?
0145           CLA,INA,RSS
0146           JMP CONTN
0147           CLB
0148           JSB LITE        YEP
0149    *
0150    CONTN  LDA BUSY3
0151           SZA             KEY PROCESSOR BUSY?
0152           JMP CIN         YEP, GIVE HIM CONTORL
0153           STA CHIT        CLEAR CHAR. BUFFER
0154    CHECK  LDA SQERR       PREPROCESSOR QUEUE OK?
0155           SZA,RSS
0156           JMP SQOK        YEP
0157           LDA ERR8        "PREPROCESSOR QUEUE OVERFLOW"
0158           LDB =D14
0159           JSB LED
0160           JMP STALL       SYSTEM GOING DOWN
0161    SQOK   LDA HQERR       PRINTER QUEUE OK?
0162           SZA,RSS
0163           JMP HQOK        YEP
0164           LDA ERR9        "PRINTER QUEUE OVERFLOW"
0165           LDB =D11
0166           JSB LED
0167           JMP STALL       SYSTEM GOING DOWN
0168    HQOK   LDA HSERR       PRINTER OVERLOADED?
0169           SZA,RSS
0170           JMP HSOK        NOP
0171           LDA ERR10       "PRINTER OVERLOADED"
0172           LDB .+9
0173           JSB LED
0174           JMP STALL       SYSTEM GOING DOWN
0175    HSOK   LDA PRTER       PRINTER MISS DEVICE FLAG?
0176           SZA,RSS
0177           JMP PROK        NOP
0178           LDA ERR1        "PRINTER HARDWARE FAULT"
0179           LDB =D11
0180           JSB LED
0181           JMP STALL       SYSTEM GOING DOWN
0182    PROK   LDA INIT        PREPROCESSOR RUNNING?
0183           SZA,RSS
0184           JMP PPOK        NOP
0185           LDA PSTAT       YEP, IS LAMP STILL ON?
0186           ALF,SLA
0187           JMP MRUN
0188           LDA ERR4        "INSPECTOR LAMP FAULT"
0189           LDB .+10
0190           JSB LED
0191           JMP STALL
```

```
0192  MRUN  LDA =STAT      MANUAL STOP REQUEST?
0193        AND =B40000
0194        SZA
0195        JMP MISS       NOP
0196        LDA ERR6       "MANUAL STOP REQUEST"
0197        LDB .+9
0198        JSB LED
0199        JMP STALL      SYSTEM GOING DOWN
0200  MISS  LDA FISEP      MISS ANY DEVICE FLAGS?
0201        SZA,RSS
0202        JMP PPOK       NOP
0203        LDA ERR2       "INSPECTOR HARDWARE FAULT"
0204        LDB =D12
0205        JSB LED
0206        JMP STALL
0207  PPOK  LDA INIT       SYSTEM ACTIVE?
0208        SZA
0209        JMP MAIN       YES, PREPROCESSOR BUSY
0210        LDA BUSY2
0211        SZA
0212        JMP MAIN       YES, KEYBOARD BUSY
0213        LDA DFLAG
0214        SZA            HAS IT BEEN DONE BEFORE?
0215        JMP MAIN       YEP
0216        JMP DEAD       SYSTEM INACTIVE
0217  *
0218  *     OPERATOR INPUT PHASE
0219  *
0220  INPUT CLA            SET INPUT NOT READY
0221        STA KEYS
0222        LDA MES2       "BALE NUMBER ?"
0223        LDB .+7
0224        JSB LED
0225        LDA RBUF       GET RESPONCE
0226        LDB .+6
0227        JSB KEY
0228        JSB BINRY
0229        LDA BIN#
0230        STA %BALE
0231        LDA RBUF       SAVE ASCII NAME
0232        LDB %NAME
0233        MVW .+3
0234        LDA MES3       "LOOM NUMBER ?"
0235        LDB .+7
0236        JSB LED
0237        LDA RBUF       GET RESPONCE
0238        LDB .+6
0239        JSB KEY
0240        JSB BINRY
0241        LDA BIN#
0242        STA %LOOM
0243        LDA MES4       "FABRIC WIDTH ?"
0244        LDB .+8
0245        JSB LED
0246        LDA RBUF       GET RESPONCE
0247        LDB .+6
0248        JSB KEY
0249        JSB BINRY
0250        LDA BIN#
0251        LDB A          VALID?
0252        ADB =D-99
0253        SSB,RSS
0254        JMP WOK
0255        CLB
0256        MPY .+10
0257  WOK   LDB A          VALID?
0258        ADB =D-999
0259        SSB
0260        JMP WCK        YEP
0261        CLB
0262        DIV .+10
0263        JMP WOK
0264  WCK   STA %WIDT
0265        LDA MES5       "FABRIC STYLE ?"
0266        LDB .+8
0267        JSB LED
```

```
0268        LDA RBUF
0269        LDB .+6
0270        JSB KEY         GET RESPONCE
0271        LDA RBUF
0272        LDB %PROD
0273        MVW .+5
0274        LDA MES6        "# INTERNAL SEAMS ?"
0275        LDB .+10
0276        JSB LED
0277        LDA RBUF
0278        LDB .+6
0279        JSB KEY
0280        JSB BINRY
0281        LDA BIN#
0282        STA %SEAM
0283        CLA,INA         SET INPUT READY
0284        STA KEYS
0285        LDA INIT        CURRENTLY INSPECTING?
0286        SZA,RSS
0287        JMP MAIN        NOP
0288        LDA MES7
0289        LDB =D11        "INSPECTING BALE XXXXX"
0290        JSB LED
0291        JMP MAIN        RETURN TO MAIN LOOP
0292 *
0293 IDLE   NOP             SET ACTIVE INPUT STREAM
0294        LDB HSTAV       AVAILABLE STACK POINTER
0295        LDA %BALE
0296        STA B,I
0297        INB
0298        LDA %LOOM
0299        STA B,I
0300        INB
0301        LDA %WIDT
0302        STA B,I
0303        STA B,I
0304        INB
0305        LDA %PROD
0306        MVW .+5
0307        CPB HSTEN       WRAP AROUND?
0308        LDB HSTAK       YEP
0309        STB HSTAV
0310        CPB HSTNX       OVERFLOW?
0311        ISZ HOEWR       YEP
0312        LDA %SEAM
0313        STA #SEAM
0314        LDA %NAME
0315        LDB NAME
0316        MVW .+2
0317        CLA
0318        STA KEYS        SET INPUT TAKEN
0319        LDA BUSY3       KEYBOARD BUSY?
0320        SZA
0321        JMP IDLE,I      YEP
0322        LDA MES7        "INSPECTING BALE XXXXX"
0323        LDB =D11
0324        JSB LED
0325        JMP IDLE,I
0326 *
0327 STALL  CLA             SYSTEM SHUT DOWN
0328        STA CHIT
0329        CLC FIS,C
0330        LDA .+5         SET FAULT LIGHT
0331        LDB .+1
0332        JSB LITE
0333        LDA .+2         SET AUTO STOP LIGHT
0334        LDB .-1
0335        JSB LITE
0336 WAIT   LDA CHIT        KEYBOARD HIT?
0337        SZA
0338        JMP START       GOT IT
0339        LDA .+6         STROBE READY LIGHT
0340        LDB .+1
0341        JSB LITE
0342        JMP WAIT
```

```
0343   *
0344   BINRY  NOP              CONVERT ASCII TO BINARY
0345          CLA,INA
0346          STA MULT
0347          LDA RBUF
0348          ADA .+5          SET LAST ADDRESS
0349          STA TEMP
0350          LDA .-6          SET # WORDS TO SEARCH
0351          STA COUNT
0352          CLA
0353          STA LFRT
0354          STA BIN#
0355   SERCH  LDA TEMP,I       GET A CHAR.
0356          LDB LFRT         LEFT OR RIGHT?
0357          SZB
0358          ALF,ALF          LEFT
0359          AND =B177
0360          ADA =B-60
0361          SSA              VALID?
0362          JMP NEXT         NOP
0363          LDB A
0364          ADB .-10         VALID?
0365          SSB,RSS
0366          JMP NEXT         NOP
0367          CLO
0368          CLE
0369          MPY MULT
0370          SOC              OVERFLOW?
0371          JMP OFLOW        YEP
0372          CLE
0373          ADA BIN#         ACCUMULATE #
0374          SEZ              OVERFLOW?
0375          JMP OFLOW        YEP
0376          STA BIN#         SAVE VALUE
0377          CLE
0378          LDA MULT
0379          CLO
0380          MPY .+10
0381          SOC              OVERFLOW?
0382          LDA =B77777      YEP, SET TO MAX
0383          STA MULT
0384   NEXT   ISZ LFRT         BUMP LEFT RIGHT FLAG
0385          LDA LFRT
0386          CPA .+1          LEFT?
0387          JMP SERCH        YEP, CONTINUE
0388          LDA TEMP
0389          ADA .-1          DECREMENT ADDRESS
0390          STA TEMP
0391          CLA
0392          STA LFRT
0393          ISZ COUNT        FINISHED?
0394          JMP SERCH
0395          JMP BINRY,I      YEP
0396   OFLOW  LDA =B77777      OVERFLOW RETURN MAX
0397          STA BIN#
0398          JMP BINRY,I
0399   *
0400   SCAN   NOP              PREPROCESSOR START UP
0401          CLF 0            INTERRUPTS OFF
0402          CLA,INA
0403          STA INIT         INITIATION FLAG
0404          LDA POFF,I       POSITIVE OFFSET
0405          IOR =B20000
0406          OTA FIS
0407          STC FIS,C
0408          LDA NOFF,I       NEGATIVE OFFSET
0409          IOR =B30000
0410          OTA FIS
0411          STC FIS,C
0412          LDA =B40000      CLEAR YARDAGE
0413          OTA FIS
0414          STC FIS,C
0415          CLA
0416          OTA FIS          SCAN FABRIC MODE
0417          STF 0            INTERRUPTS ON
0418          JMP SCAN,I
```

```
0419   *
0420   KEYS  NOP                0 - NO INPUT, 1 - INPUT OK
0421   DFLAG NOP                0 - SYSTEM CHECK, 1 - SYSTEM DEAD
0422   WIDPR DEC 450            ACTIVE FABRIC WIDTH
0423   #SEAM NOP                ACTIVE # INTERNAL SEAMS
0424   INIT  NOP                PREPROCESSOR FLAG
0425   DBUG  NOP                DEBUG FLAG
0426   BIN#  NOP                BINARY CONVERSION #
0427   RBUF  DEF *+1            KEYBOARD BUFFER ADDRESS
0428         ASC 16,
0429   HSTNX DEF *+3            HEADER STACK NEXT POINTER
0430   HSTAV DEF *+2            HEADER STACK AVAILABLE
0431   HSTAK DEF *+1            HEADER STACK ADDRESS
0432         BSS 80             ROOM FOR TEN REPORT HEADERS
0433   HSTEN DEF *              HEADER STACK LAST ADDRESS
0434   HSERR NOP
0435   %BALE NOP                BALE # ENTERED
0436   %LOOM NOP                LOOM # ENTERED
0437   %WIDT NOP                WIDTH ENTERED
0438   %PROD DEF *+1            STYLE ENTERED
0439         BSS 5
0440   %SEAM NOP                # SEAMS ENTERED
0441   %NAME DEF *+1            ASCII BALE NAME
0442         BSS 3
0443   TEMP  NOP
0444   COUNT NOP
0445   MULT  NOP
0446   LFRT  NOP
0447   *
0448   MES1  DEF *+1
0449         ASC 12,FABRIC INSPECTION SYSTEM
0450   MES2  DEF *+1
0451         ASC 7,BALE NUMBER ?
0452   MES3  DEF *+1
0453         ASC 7,LOOM NUMBER ?
0454   MES4  DEF *+1
0455         ASC 8,FABRIC WIDTH ?
0456   MES5  DEF *+1
0457         ASC 8,FABRIC STYLE ?
0458   MES6  DEF *+1
0459         ASC 10,# INTERNAL SEAMS ?
0460   NAME  DEF *+10
0461   MES7  DEF *+1
0462         ASC 8,INSPECTING BALE
0463         ASC 3,
0464   ERR1  DEF *+1
0465         ASC 11,PRINTER HARDWARE FAULT
0466   ERR2  DEF *+1
0467         ASC 12,INSPECTOR HARDWARE FAULT
0468   ERR3  DEF *+1
0469         ASC 6,TURN ON LAMP
0470   ERR4  DEF *+1
0471         ASC 10,INSPECTOR LAMP FAULT
0472   ERR5  DEF *+1
0473         ASC 9,TURN ON MANUAL RUN
0474   ERR6  DEF *+1
0475         ASC 9,MANUAL STOP REQUEST
0476   ERR7  DEF *+1
0477         ASC 8,DEBUG TERMINATED
0478   ERR8  DEF *+1
0479         ASC 14,PREPROCESSOR QUEUE OVERFLOW
0480   ERR9  DEF *+1
0481         ASC 11,PRINTER QUEUE OVERFLOW
0482   ERR10 DEF *+1
0483         ASC 9,PRINTER OVERLOADED
0484   *
0485   .     EQU 32B
0486   A     EQU 0
0487   B     EQU 1
0488   FIS   EQU 10B            PREPROCESSER I/O SLOT
0489   POFF  OCT 56             POSITIVE OFFSET ADDRESS
0490   NOFF  OCT 70             NEGATIVE OFFSET ADDRESS
0491   *
0492   BPADR OCT 2              1ST BASE PAGE ADDRESS
0493   BPAGE DEF *+1            BASE PAGE BUFFER ADDRESS
0494         OCT 102002         PROTECT HALT
```

```
0495            OCT 102003      PROTECT HALT
0496            OCT 102004      POWER FAIL HALT
0497            OCT 102005      MEMORY PROTECT HALT
0498            OCT 102006      DMA INTERRUPT HALT
0499            OCT 102007      DMA INTERRUPT HALT
0500            JSB 14B,I       PREPROCESSOR TRAP CELL
0501            JSB 15B,I       PRINTER TRAP CELL
0502            JSB 16B,I       KEYBOARD TRAP CELL
0503            JSB 17B,I       FLOPPY DISK TRAP CELL
0504   DVR10    NOP             DRIVER ADDRESS
0505   DVR11    NOP             DRIVER ADDRESS
0506   DVR12    NOP             DRIVER ADDRESS
0507            DEF 2B          NO DRIVER
0508            DEC -10
0509            DEC -9
0510            DEC -8
0511            DEC -7
0512            DEC -6
0513            DEC -5
0514            DEC -4
0515            DEC -3
0516            DEC -2
0517            DEC -1
0518            DEC 0
0519            DEC 1
0520            DEC 2
0521            DEC 3
0522            DEC 4
0523            DEC 5
0524            DEC 6
0525            DEC 7
0526            DEC 8
0527            DEC 9
0528            DEC 10
0529            DEC -3          GRADING CONSTANTS
0530            DEC -4
0531            DEC -4
0532            DEC -7
0533            DEC -10
0534            DEC -10
0535            DEC -2
0536            DEC -6
0537            DEC -11
0538            OCT 20          POSITIVE OFFSET TABLE
0539            DEC 0
0540            DEC 0
0541            DEC 0
0542            DEC 0
0543            DEC 0
0544            DEC 0
0545            DEC 0
0546            DEC 0
0547            DEC 0
0548            OCT 20          NEGATIVE OFFSET TABLE
0549            DEC 0
0550            DEC 0
0551            DEC 0
0552            DEC 0
0553            DEC 0
0554            DEC 0
0555            DEC 0
0556            DEC 0
0557            DEC 0
0558            DEC -5          0.4 PTS/YRD 1ST QUALITY
0559            DEC -4          0.8 PTS/YRD 2ND QUALITY
0560   #WORD    ABS *-BPAGE     # WORDS IN BASE PAGE
0561   SYSOP    NOP             SYSTEM OPTIONS
0562            END MONTR
**** LIST END ****
```

TABLE 4

```
:LI,S,1,SKYBU

0001        ASMB,L,C
0002        HED FABRIC INSPECTION KEYBOARD UTILITIES
0003        NAM KYBU,7
0004        ENT LED,KEY,HIT,LITE,,KEYS
0005        ENT CHIT,CIN,STATE,PSTAT
0006        EXT MAIN,KEYS
0007        ENT BUSYS
0008   *
0009   *
0010   *
0011   *    UTILITY ROUTINES FOR FRONT PANEL
0012   *    DISPLAY, KEYBOARD, AND LIGHTS.
0013   *    KEYBOARD IS INTERRUPT DRIVEN
0014   *
0015   *
0016   *    DAVID GATES
0017   *
0018   *    (10/10/76)
0019   *
0020   *
0021   *
0022   *    DISPLAY WRITE ROUTINE
0023   *
0024   *    A <BUFFER ADDRESS>
0025   *    B <WORD COUNT POS>
0026   *
0027   LED  NOP
0028        STA BUFAD    SAVE ADDRESS
0029        CMB,INB
0030        STB NWORD    SAVE COUNT
0031        CLA
0032        OTA KYB      BLANK LED
0033        STC KYB
0034        LDA PSET     RESET DISPLAY POINTER
0035        STA CBUF
0036        LDA NWORD    LEGAL COUNT?
0037        SSA,RSS
0038        JMP LED,I    NOP, FINISHED
0039   WRITE LDA BUFAD,I
0040        ALF,ALF      POSITION LEFT CHAR.
0041        JSB OUT
0042        LDA BUFAD,I
0043        JSB OUT      OUTPUT RIGHT CHAR.
0044        ISZ BUFAD
0045        ISZ NWORD    FINISHED?
0046        JMP WRITE
0047        JMP LED,I    YEP
0048   *
0049   OUT  NOP          DISPLAY A CHARACTER
0050        AND =B77     ONLY LOWER SIX BITS
0051        IOR =B20000  WRITE BIT FOR I/F
0052        STA CBUF,I   SAVE DISPLAY CONTENT
0053        ISZ CBUF     BUMP ADDRESS
0054   WAIT LIB KYB      GET I/F STATUS
0055        SSB          WRITE CYCLE BUSY?
0056        JMP WAIT     YEP
0057        OTA KYB
0058        STC KYB      CHAR. INITIATED
0059        JMP OUT,I
0060        SKP
0061   *
0062   *    KEYBOARD READ ROUTINE
0063   *
0064   *    A <BUFFER ADDRESS>
0065   *    B <WORD COUNT POS>
0066   *
0067   KEY  NOP
0068        STA BUFAD    SAVE ADDRESS
0069        CMB,INB
0070        STB IWORD    SAVE COUNT
0071        STB NWORD
```

```
0072           JSB,RSS         LEGAL COUNT?
0073           JMP KEY,I       NOP,FINISHED
0074           CLA,INA
0075           STA BUSY3       PROCESSOR BUSY FLAG
0076           LDA =B20040
0077           LDB BUFAD
0078   BLANK   STA B,I         BLANK FILL BUFFER
0079           INB
0080           ISZ NWORD       DONE?
0081           JMP BLANK
0082           LDA IWORD       YES,RESET COUNT
0083           STA NWORD
0084   READ    JSB IN          TOP OF READ LOOP
0085           CPA .+3         BACK SPACE?
0086           RSS
0087           JMP NORML       NOP
0088           LDA IWORD       TOO FAR?
0089           CPA NWORD
0090           JMP READ        YEP, STILL ON LEFT CHAR.
0091           JSB BACK        BACK SPACE DISPLAY
0092           LDA BUFAD
0093           ADA .-1         RESTORE ADDRESS
0094           STA BUFAD
0095           LDA BUFAD,I
0096           AND =B177400    RESTORE BLANK
0097           IOR =B40
0098           STA BUFAD,I
0099           LDA NWORD       RESTORE COUNT
0100           ADA .-1
0101           STA NWORD
0102           JMP RIGHT       REREAD RIGHT CHAR.
0103   NORML   ALF,ALF
0104           IOR =B40        JUST READ LEFT CHAR.
0105           STA BUFAD,I
0106           ALF,ALF
0107           JSB OUT         ECHO ON DISPLAY
0108   RIGHT   JSB IN
0109           CPA .+3         BACK SPACE?
0110           RSS
0111           JMP NORMR       NOP
0112           JSB BACK        BACK SPACE DISPLAY
0113           LDA =B20040
0114           STA BUFAD,I     BLANK LAST CHAR.
0115           JMP READ        REREAD LEFT CHAR.
0116   NORMR   LLB A
0117           LDA BUFAD,I     JUST READ RIGHT CHAR.
0118           AND =B177400
0119           IOR B           MERGE IT IN
0120           STA BUFAD,I
0121           JSB OUT         ECHO IN DISPLAY
0122           ISZ BUFAD       BUMP ADDRESS
0123           ISZ NWORD       FINISHED?
0124           JMP READ
0125   QUIT    CLA             YEP, CLEAR BUSY FLAG
0126           STA BUSY3
0127           JMP KEY,I
0128   *
0129   BACK    NOP             BACK SPACE DISPLAY
0130           LDA CBUF
0131           ADA .-1         RESET BUFFER POINTER
0132           STA CBUF
0133           CLA             BLANK FILL DISPLAY
0134           OTA KYB
0135           STC KYB
0136           LDA CBUF        RESET POINTER
0137           STA TEMP
0138           LDA PSET        RESTORE CONTENTS
0139           STA CBUF
0140   COUT    LDA CBUF        LAST ADDRESS?
0141           CPA TEMP
0142           JMP BACK,I      YEP, FINISHED
0143           LDA CBUF,I
0144           JSB OUT         SEND OUT A CHAR.
0145           JMP COUT
0146   *
0147   IN      NOP             READ A CHARACTER
```

```
0148  IGNOR CLA
0149        STA CHIT        ZERO CHAR. BUFFER
0150        JMP MAIN        RETURN TO MONITOR
0151  CIN   LDA CHIT        MONITOR RETURNED
0152        LDB A
0153        ADB =0-11       VALID CHAR. ?
0154        SSB,RSS
0155        JMP IN,I        YEP, GIVE IT TO EM
0156        CPA .+2         NEXT KEY?
0157        JMP QUIT        YEP, STOP
0158        CPA .+3         BACK SPACE KEY?
0159        JMP IN,I        YEP, LET EM HAVE IT
0160        JMP IGNOR       IGNORE ALL OTHERS
0161        SKP
0162  *
0163  *     KEYBOARD COMPLETION INTERRUPT PROCESSOR
0164  *
0165  HIT   DEF *           INTERRUPT TRAP ADDRESS
0166        CLF 0           INT. OFF
0167        STA SAVA
0168        STB SAVB        SAVE REGISTERS
0169        ERA,ALS
0170        SOC
0171        INA
0172        STA SAVED
0173        LIA KYB         GET CHAR. ON I/F
0174        AND =B177
0175        STA CHIT        SAVE CHARACTER HIT
0176        LDA =B10000
0177        OTA KYB         REENABLE KEYBOARD
0178        STC KYB,C       CLEAR DEVICE FLAG
0179        LDA SAVED
0180        ELA,RAR         RESTORE REGISTERS
0181        CLO
0182        SLA
0183        STF 1
0184        LDA SAVA
0185        LDB SAVB
0186        STF 0           INT. ON
0187        JMP HIT,I
0188        SKP
0189  *
0190  *     LIGHT ROUTINE
0191  *
0192  *     A <LIGHT NUMBER>
0193  *     B <FUNCTION     >
0194  *
0195  LITE  NOP             MUST BE SAVED TO REENTRANT
0196        ADA MASK
0197        LDA A,I         FORM BIT PATTERN
0198        SZB,RSS
0199        JMP ALT
0200        SSB
0201        JMP OFF
0202        IOR STATE       ON REQUEST   B>0
0203        JMP SEND
0204  ALT   XOR STATE       ALTERNATE    B=0
0205        JMP SEND
0206  OFF   CMA             OFF REQUEST  B<0
0207        AND STATE
0208  SEND  STA STATE       SAVE LIGHT STATE
0209        IOR =B30000
0210        OTA KYB         CHANGE EM UP
0211        STC KYB
0212        LDA =B40000
0213        OTA KYB         STROBE READY
0214        STC KYB         IF ENABLED
0215        LDA =B100000
0216        OTA KYB         RESTORE READ/WRITE STATE
0217        STC KYB
0218        LIA KYB         GET I/F STATUS
0219        STA PSTAT
0220        JMP LITE,I
0221  *
0222  MASK  DEF *+1         BIT PATTERN TABLE
0223        OCT 007700      ALL LIGHTS          A=0
```

```
0224        OCT 000100      POLITARY REVERSE    A=1
0225        OCT 000200      RUN/STOP            A=2
0226        OCT 000400      VELOCITY            A=3
0227        OCT 001000      NO FABRIC           A=4
0228        OCT 002000      FAULT               A=5
0229        OCT 004000      READY ENABLE        A=6
0230        SKP
0231 *
0232 *      INITIALIZE UTILITY ROUTINES
0233 *
0234 .KEYS  NOP
0235        CLF 0           INT. OFF
0236        LDA =B100000
0237        OTA KYB         SET READ / WRITE ON I/F
0238        STC KYB
0239        LIA KYB         GET STATUS
0240        AND =B20000
0241        SZA,RSS         SENSOR POWER UP?
0242        HLT KYB         NOP,WHAT TO DO?
0243        CLA
0244        OTA KYB         BLANK DISPLAY
0245        STC KYB
0246        LDA =B10000
0247        OTA KYB         ENABLE KEYBOARD
0248        STC KYB,C
0249        CLA
0250        STA KEYS        SET INPUT NOT READY
0251        STA CHIT        CLEAR CHAR. BUFFER
0252        STA BUSYS       SET PROCESSOR NOT BUSY
0253        LDB .-1
0254        JSB LITE        TURN LIGHTS OFF
0255        LDA .+6
0256        LDB .+1
0257        JSB LITE        ENABLE AND STROBE READY
0258        LDA .+1         REVERSE POLARITY (START UP BUG)
0259        LDB .
0260        JSB LITE
0261        STF 0           INT. ON
0262        JMP .KEYS,I
0263        SKP
0264 *
0265 *      CONSTANTS AND STORAGE
0266 *
0267 STATE  NOP             CURRENT LIGHT STATE
0268 CHIT   NOP             LAST CHARACTER HIT
0269 PSTAT  NOP             KEYBOARD STATUS
0270 BUFAD  NOP             BUFFER POINTER
0271 NWORD  NOP             BUFFER COUNT
0272 IWORD  NOP             BUFFER COUNT
0273 PSET   DEF *+2         DISPLAY RESET ADDRESS
0274 CBUF   DEF *+1         DISPLAY CURRENT ADDRESS
0275        BSS 32          32 CHAR.DISPLAY BUFFER
0276 TEMP   NOP
0277 SAVA   NOP             REGISTER SAVE AREA
0278 SAVB   NOP
0279 SAVED  NOP
0280 BUSYS  NOP             PROCESSOR BUSY FLAG
0281 KYB    EQU 12B         KEYBOARD I/O SLOT
0282 A      EQU 0
0283 B      EQU 1
0284 .      EQU 32B
0285        END
**** LIST END ****
```

TABLE 5

```
:LI,S,1,SSCAN

0001 ASMB,L,C
0002      HED FABRIC INSPECTION PREPROCESSOR DRIVER
0003      NAM SCANR,7
0004      ENT SCANR,BUSY1
0005      EXT GRADO,GOAVL
0006      EXT GOCNT,WDOPR
0007      EXT GRADR,LISTR
```

```
0008            ENT .SCAN,FISEP
0009            EXT INIT,LITE
0010            EXT #SEAM,IDLE
0011            EXT KEYS,DBUG
0012            ENT SQERR
0013   *
0014   *
0015   *
0016   *        PREPROCESSOR DRIVER FOR FABRIC INSPECTION SYSTEM
0017   *        MAPS ONE INCH SQUARES FROM COMPACTER LOGIC ONTO
0018   *        CONTIGUOUS DEFECT SPOTS WITHIN A YARD FOR LATER
0019   *        GRADING ACCORDING TO USER SELECTED GRADING SCHEME
0020   *
0021   *
0022   *
0023   *        SCAN QUEUE FORMAT      ** YARDAGE    **
0024   *                               ** FLAG WORD  **
0025   *        VARIABLE               ** WIDTH      **
0026   *        LENGTH                 ** DEFECTS    **
0027   *        RECORDS                **     .      **
0028   *                               **     .      **
0029   *        TERMINATOR             **    -1      **
0030   *
0031   *
0032   *
0033   *        GRADE QUEUE FORMAT     ** FLAG WORD  **
0034   *                               ** YARDAGE    **
0035   *        (MINIMUM WIDTH)        ** WARP DX1   **
0036   *        (MAXIMUM WIDTH)        ** WARP DX2   **
0037   *                               ** FILL DY1   **
0038   *        WIDTH USED FOR         ** FILL DY2   **
0039   *        SPECIAL DEFECTS        ** # SQUARES  **
0040   *                               ** POS/NEG SUM**
0041   *
0042   *
0043   *        FLAG WORD DESCRIPTION
0044   *
0045   *        BIT 15 - VELOCITY LOW    (PREPROCESSOR)
0046   *            14 - NO FABRIC       (SOFTWARE)
0047   *            13 - SEAM DETECTED   (PREPROCESSOR)
0048   *            12 - NARROW FABRIC   (SOFTWARE)
0049   *            11 - SHADE DATA      (PREPROCESSOR)
0050   *            10 - BARRE DETECTED  (PREPROCESSOR)
0051   *             9 - TAG DETECTED    (PREPROCESSOR)
0052   *             8 - 100 YARDS       (SOFTWARE)
0053   *             7 - FABRIC DEFECTS  (SOFTWARE)
0054   *             6 - UNUSED POSITION
0055   *           5-0 - INCH LOCATION   (PREPROCESSOR)
0056   *
0057   *
0058   *
0059   *        NOTE: SHADE ALGROTHIM NOT IMPLEMENTED
0060   *
0061   *
0062   *        DAVID GATES
0063   *
0064   *        (11/5/76)
0065   *
0066   SCANR DEF *            INTERRUPT TRAP ADDRESS
0067         CLF 0
0068         STA INTA         SAVE REGISTERS
0069         STB INTB
0070         ERA,ALS
0071         SOC
0072         INA
0073         STA INTEO
0074         LDA LITE         ALLOW REENTRANCE
0075         STA %LITE
0076         LDA SQHVL
0077         STA SQSAV        ADDRESS OF THIS ENTRY
0078         LDA =D-76
0079         STA COUNT        MAXIMUM # DEFECTS
0080   LOOPR SFS FIS
0081         JMP MISS         MISSING DEVICE FLAG
0082         LIA FIS          DATA WORD IN
0083         STC FIS,C
```

```
0084            JSB SOPUT       SAVE A WORD
0085            CPA .-1
0086            JMP LOADD       LAST WORD IN
0087            ISZ COUNT
0088            JMP LOADM       GET SOME MORE
0089            LDA .+5         SET FAULT LIGHT
0090            LDB .+1
0091            JSB LITE
0092    BAD     SFS FIS
0093    MISQ    ISZ FISER
0094            LIA FIS         BAD INFO
0095            STC FIS,C
0096            CPA .-1
0097            JMP XBAD
0098            LDA FISER       RETRY LIMITS EXCEEDED?
0099            CPA =D200
0100            JMP STOP        YEP, SHUT DOWN DRIVER
0101            JMP BAD
0102    XBAD    LDA SQSAV       IGNORE LAST ENTRY
0103            STA SQAVL
0104            LDA BUSY1
0105            SZA,RSS
0106            JSB LISTP       INITIATE PRINTER
0107            LDA .+6         STROBE READY LIGHT
0108            LDB .+1
0109            JSB LITE
0110            JMP RETRN
0111    LOADD   LDA COUNT       CHECK STATUS
0112            ADA =D71
0113            SSA,RSS         ATLEAST TWO DEFECTS?
0114            JMP STAT0       YEP
0115            LDA .+4
0116            LDB .+1         NO FABRIC LIGHT
0117            JSB LITE
0118            LDA .+5
0119            LDB .+1         SET FAULT LIGHT
0120            JSB LITE
0121            JMP XBAD
0122    STAT0   LDB SQSAV
0123            INB
0124            CPB SQEND
0125            LDB SCANQ
0126            LDA DBUG        DEBUG MODE?
0127            ELA
0128            LDA B,I         GET FLAG WORD
0129            STB FLGAD       SAVE ADDRESS OF FLAGS
0130            SEZ
0131            JSB DEBUG       DEBUG ROUTINE
0132            STA FWORD
0133            SSA,RSS
0134            JMP STAT1
0135            LDA .+3         SET VELOCITY LOW LIGHT
0136            LDB .+1
0137            JSB LITE
0138            JMP XBAD        VELOCITY LOW
0139    STAT1   ALF
0140            SSA,RSS
0141            JMP STAT2
0142            JMP XBAD        SHADE INFO
0143    STAT2   INB
0144            CPB SQEND
0145            LDB SCANQ
0146            LDA B,I
0147            CMA,INA
0148            SSA
0149            JMP STAT3
0150            LDA .+4         SET NO FABRIC LIGHT
0151            LDB .+1
0152            JSB LITE
0153            JMP XBAD        NO FABRIC
0154    STAT3   LDA FWORD
0155            RAL,RAL
0156            SSA,RSS
0157            JMP STAT4
0158            LDB SQSAV,I
0159            SZB,RSS
```

```
0160            JMP XBAD        EXTRA SEAM
0161            LDA .+1         REVERSE LIGHT POLARITY
0162            LDB .
0163            JSB LITE
0164            LDA #SEAM       INTERNAL SEAM?
0165            SZA,RSS
0166            JMP EOB         NO, END OF BALE
0167            ADA .-1
0168            STA #SEAM       YEP, DECREMENT COUNT
0169            LDA FLGAD,I     CLEAR SEAM BIT
0170            AND =B157777
0171            STA FLGAD,I
0172            JMP STAT4
0173  EOB       LDA KEYS
0174            SZA             START NEXT BALE?
0175            JMP RESET       YEP
0176  STOP      CLC FIS,C       STOP PREPROCESSOR
0177            CLA
0178            STA INIT        SET FLAG FOR MONITOR
0179            JMP STAT4
0180  RESET     LDA =B40000     CLEAR YARDAGE
0181            OTA FIS
0182            STC FIS,C
0183            CLA
0184            OTA FIS
0185            STC FIS,C
0186            JSB IDLE        GET OPERATOR INPUT
0187  STAT4     LDA .+4         TURN OFF NO FABRIC LIGHT
0188            LDB .-1
0189            JSB LITE
0190            LDA .+3         TURN OFF VELOCITY LIGHT
0191            LDB .-1
0192            JSB LITE
0193            LDA BUSY1       MAP PROCESSOR BUSY?
0194            SZA,RSS
0195            JMP MAP         INITIATE MAPPING
0196  RETRN     LDA INTEO
0197            ELA,RAR         RESTORE REGISTERS
0198            CLO
0199            SLA
0200            STF 1
0201            LDA %LITE
0202            STA LITE
0203            LDA INTA
0204            LDB INTB
0205            STF 0
0206            JMP SCHNR,I
0207  *
0208  *
0209  *         MAPPING LOGIC FOR DEFECT DATA IN SCAN QUEUE
0210  *
0211  *
0212  MAP       LDA SCANR       SAVE REGISTERS
0213            STA SAVR
0214            LDA INTA
0215            STA SAVA
0216            LDA INTB
0217            STA SAVB
0218            LDA INTEO
0219            STA SAVEO
0220            LDA %LITE
0221            STA .LITE
0222            CLA,INA
0223            STA BUSY1       SET BUSY STATUS
0224            STF 0
0225  RETRY     LDA SQAVL       FINISHED PROCESSING ?
0226            CPA SQNXT
0227            JMP EXIT
0228            JSB SQGET       UNLOAD SCAN INFO
0229            CPA .-1
0230            JMP FAULT
0231            STA SQYRD
0232            JSB SQGET
0233            CPA .-1
0234            JMP FAULT
0235            STA FLAG2
```

```
0236            JSB SOGET
0237            CPA .-1
0238            JMP FAULT
0239            STA WIDTH
0240            LDB WDMIN
0241            CMB,INB
0242            ADR A
0243            SSB
0244            STA WDMIN       MIN WIDTH
0245            LDB WDMAX
0246            CMB,INB
0247            ADB A
0248            SSB,RSS
0249            STA WDMAX       MAX WIDTH
0250            LDA FLAGS
0251            AND =B77
0252            SZA
0253            JMP WDCHK
0254            CLB
0255            LDA SQYRD
0256            SZA,RSS
0257            JMP WDCHK
0258            DIV =B100
0259            SZB
0260            JMP WDCHK
0261            LDA FLAGS       100 YARDS PASSED
0262            IOR =B400
0263            STA FLAGS
0264    WDCHK   LDA WFLAG
0265            SZA
0266            JMP SEAM        IGNORE WIDTH VIOLATION
0267            LDA WDOPR
0268            CMA,INA
0269            ADA WIDTH       WIDTH VIOLATION ?
0270            SSA,RSS
0271            JMP SEAM        NOP
0272            LDA FLAGS
0273            IOR =B10000
0274            STA FLAGS       NARROW FABRIC
0275            CLA,INA
0276            STA WFLAG
0277    SEAM    LDA FLAGS       CHECK FOR SEAM
0278            RAL,RAL
0279            SSA,RSS
0280            JMP TYPE
0281            LDA =B20000
0282            JSB STUFF       CREATE SEAM ENTRY
0283            JSB GRADE       ITS PAST HISTORY NOW
0284            CLA
0285            STA SQYRD
0286            STA WDMAX
0287            LDA =B1777
0288            STA WDMIN
0289    TRASH   JSB SOGET       CLEAR OUT SCAN
0290            CPA .-1
0291            JMP RETRY
0292            JMP TRASH
0293    FAULT   LDA .+5         GARBAGE DATA SET FAULT
0294            LDB .+1
0295            JSB LITE
0296            JMP TRASH
0297    TYPE    LDA FLAGS       CHECK DEFECT TYPE
0298            AND =B17400
0299            SZA,RSS
0300            JMP DEFCT       NORMAL DEFECT SQUARE
0301            LDA FLAGS
0302            AND =B400
0303            SZA
0304            JSB STUFF       CREATE 100 YARD ENTRY
0305            LDA FLAGS
0306            AND =B1000
0307            SZA,RSS
0308            JMP BARRE
0309            LDB TFLAG
0310            SZB
0311            JMP BARRE       ONE VIOLATION/YARD
```

```
0312            CLB,INB
0313            STB TFLAG
0314            JSB STUFF       CREATE TAG ENTRY
0315   BARRE    LDA FLAGS
0316            AND =B2000
0317            SZA
0318            JSB STUFF       CREATE BARRE ENTRY
0319            LDA FLAGS
0320            AND =B4000
0321            SZA,RSS
0322            JMP SHADE
0323            LDB SFLAG
0324            SZB
0325            JMP SHADE       ONE VIOLATION/YARD
0326            CLB,INB
0327            STB SFLAG
0328            JSB STUFF       CREATE SHADE ENTRY
0329   SHADE    LDA FLAGS
0330            AND =B10000
0331            SZA
0332            JSB STUFF       CREATE WIDTH VIOLATION
0333   DEFCT    LDA SQYRD       MAPS DEFECT SQUARES TO SPOTS
0334            CPA YARDS
0335            RSS
0336            JMP GRADE       ITS PAST HISTORY NOW
0337            LDA WIDTH
0338            CLB
0339            DIV .+10
0340            ADA .-2
0341            STA LAST        FILL COORDINATE OF LAST SQUARE
0342            LDA =D-72
0343            STA #DFCT
0344   BOX      LDA GRADO
0345            STA GAD         DEFECT SEARCH ADDRESS
0346            JSB SQGET
0347            STA SQVAL
0348            CPA .-1         FINISHED?
0349            JMP RETRY
0350            ISZ #DFCT
0351            RSS
0352            HLT 55B
0353            AND =B177
0354            STA BY1         GET SQUARE INFO
0355            SZA,RSS
0356            JMP BOX         IGNORE SELVEGE
0357            CPA .+1
0358            JMP BOX
0359            CMA,INA
0360            ADA LAST
0361            SSA
0362            JMP BOX         IGNORE SELVEGE
0363            LDA FLAGS
0364            AND =B77
0365            STA BX1
0366            LDA SQVAL
0367            RAL,RAL
0368            AND .+3
0369            STA PNSUM
0370            LDA BX1
0371            CMA,INA
0372            ADA WARP
0373            SSA
0374            JMP GOADD       GAP IN WARP FOR ALL
0375   SPOTS    LDB GAD         SEARCH ALL DEFECT SPOTS
0376            CPB GOAVL
0377            JMP GOADD       CREATE DEFECT TO GRADE
0378            JMP EXPAN       FIRST TRY TO EXPAND DEFECT
0379   GOADD    LDA GOCNT
0380            CPA MAXDF
0381            JMP BOX         MAXIMUM DEFECTS/YARD
0382            LDA =B200
0383            LDB GOAVL
0384            STA B,I         ADD NEW DEFECT ENTRY
0385            INB
0386            LDA SQYRD
0387            STA B,I
0388            INB
```

```
0389        LDA BX1
0390        STA B,I
0391        INB
0392        INA
0393        STA B,I
0394        STA WARP
0395        INB
0396        LDA BY1
0397        STA B,I
0398        INB
0399        INA
0400        STA B,I
0401        INB
0402        CLA,INA
0403        STA B,I
0404        INB
0405        LDA PNSUM
0406        STA B,I
0407        INB
0408        STB GOAVL
0409        ISZ GOCNT
0410        JMP BOX
0411 EXPAN  LDB GAD          TRY TO EXPAND DEFECTS
0412        LDA B,I
0413        ALF,ALF
0414        SSA,RSS
0415        JMP GONXT        NOT A DEFECT SPOT
0416        ADB .+3
0417        LDA B,I          GET DEFECT BOUNDS
0418        STA DX2
0419        INB
0420        LDA B,I
0421        STA DY1
0422        INB
0423        LDA B,I
0424        STA DY2
0425        LDA DX2          CHECK COMMON LINE
0426        ADA .-1
0427        CPA BX1
0428        JMP FILL
0429        INA
0430        CPA BX1
0431        JMP FILL
0432        JMP GONXT        GAP IN WARP
0433 FILL   LDA DY1
0434        CMA,INA          CHECK COMMON LINE
0435        ADA BY1
0436        SSA
0437        JMP OUT
0438        LDA DY2
0439        CMA,INA
0440        ADA BY1
0441        SSA,RSS
0442        JMP OUT
0443        JMP LONGR
0444 OUT    LDA BY1
0445        INA
0446        CPA DY1
0447        JMP LEFT
0448        LDA BY1
0449        CPA DY2
0450        JMP RIGHT
0451        JMP GONXT        GAP IN FILL
0452 LEFT   LDB GAD
0453        ADB .+4          EXPAND LEFT
0454        LDA BY1
0455        STA B,I
0456        JMP LONGR
0457 RIGHT  LDB GAD          EXPAND RIGHT
0458        ADB .+5
0459        LDA BY1
0460        INA
0461        STA B,I
0462 LONGR  LDB GAD          EXPAND LENGTH
0463        ADB .+3
0464        LDA BX1
```

```
0465          INA
0466          STA B,I
0467          STA WARP
0468          ADB .+3
0469          ISZ B,I        # SQUARES
0470          INB
0471          LDA B,I
0472          ADA PNSUM      POS/NEG SUM
0473          STA B,I
0474          LDB GRADQ      COMBINE DEFECTS
0475          JMP FIRST
0476  SKIP    LDB GADNX
0477          ADB .+2
0478  FIRST   STB GADNX
0479          CPB GAD
0480          JMP SKIP
0481          CPB GQAVL
0482          JMP BOX        END OF GRADE QUEUE
0483          LDA B,I
0484          ALF,ALF
0485          SSA,RSS        FOUND NEXT SPOT
0486          JMP SKIP
0487          ADB .+3
0488          LDA BX1
0489          CPA B,I
0490          RSS
0491          JMP SKIP
0492          INB
0493          LDA BY1
0494          INA
0495          CPA B,I
0496          RSS            COMBINE TWO SPOTS
0497          JMP SKIP
0498          INB
0499          LDA B,I
0500          LDB GAD
0501          ADB .+5
0502          STA B,I        EXPAND 1ST SPOT RIGHT
0503          INB
0504          LDA GADNX
0505          ADA .+6
0506          LDA A,I
0507          ADA B,I
0508          STA B,I        # SQUARES
0509          INB
0510          LDA GADNX
0511          ADA .+7
0512          LDA A,I
0513          ADA B,I
0514          STA B,I        POS/NEG SUM
0515          LDB GADNX
0516          CLA
0517          STA B,I        PURGE GRADE ENTRY
0518          LDA SQCNT
0519          ADA .-1
0520          STA SQCNT
0521          JMP BOX
0522  GQNXT   LDA GAD        LOCATE NEXT ENTRY
0523          ADA .+8
0524          STA GAD
0525          JMP SPOTS
0526  EXIT    CLF 0
0527          CLA
0528          STA BUSY1
0529          JSB LISTR      INITIATE PRINTER
0530          LDA .LITE
0531          STA LITE
0532          LDA SAVEQ      RESTORE REGISTERS
0533          ELA,RAR
0534          CLO
0535          SLA
0536          STF 1
0537          LDA SAVA
0538          LDB SAVB
0539          STF 0
0540          JMP SAVP,I
```

```
0541   *
0542   SQPUT  NOP                STORE IN SCAN QUEUE
0543          LDB  SQAVL
0544          STA  B,I
0545          INB
0546          CPB  SQNXT
0547          JMP  OFLOW         QUEUE OVERFLOW
0548          CPB  SQEND
0549          LDB  SQANO
0550          STB  SQAVL
0551          JMP  SQPUT,I
0552   OFLOW  ISZ  SQERR         SCANQ OVERFLOW
0553          JMP  XBAD
0554          JMP  XBAD
0555   *
0556   SQGET  NOP                LOAD FROM SCAN QUEUE
0557          LDB  SQNXT
0558          LDA  B,I
0559          CPB  SQAVL         GONE TOO FAR?
0560          CCA,RSS            YEP, RETURN TERMINATER
0561          INB
0562          CPB  SQEND
0563          LDB  SQANO
0564          STB  SQNXT
0565          JMP  SQGET,I
0566   *
0567   STUFF  NOP
0568          CPA  =B400
0569          JMP  FORCE         FORCE 100 YARD ENTRY
0570          CPA  =B20000
0571          JMP  FORCE         FORCE SEAM ENTRY
0572          LDB  GQCNT
0573          CPB  MAXDF
0574          JMP  STUFF,I       MAXIMUM DEFECTS/YARD
0575   FORCE  LDB  GQAVL         CREATE GRADE ENTRY
0576          STA  B,I
0577          INB
0578          LDA  SQYRD
0579          STA  B,I
0580          INB
0581          CLA
0582          STA  B,I
0583          INB
0584          STA  B,I
0585          INB
0586          STA  B,I
0587          INB
0588          STA  B,I
0589          INB
0590          LDA  WDMIN
0591          STA  B,I
0592          INB
0593          LDA  WDMAX
0594          STA  B,I
0595          INB
0596          STB  GQAVL
0597          ISZ  GQCNT
0598          JMP  STUFF,I
0599   *
0600   GRADE  NOP                GRADE AND MOVE TO HISTORY QUEUE
0601          JSB  GRADR
0602          LDA  GRADO
0603          STA  GQAVL
0604          CLA
0605          STA  GQCNT
0606          STA  WFLAG
0607          STA  SFLAG
0608          STA  TFLAG
0609          CCA
0610          STA  WARP
0611          LDA  SQYRD
0612          STA  YARDS
0613          JMP  GRADE,I
0614   *
0615   DEBUG  NOP                DEBUG ROUTINE
0616          AND  =B77
```

```
0617        STA  B,I
0618        LIA  1              FAKE FLAG WORD
0619        CPA  SRVAL
0620        AND  =B100000
0621        AND  =B177700
0622        IOR  B,I
0623        STA  B,I
0624        LIA  1
0625        STA  SRVAL
0626        AND  =B100077
0627        OTA  1              CLEAR SWITCHES
0628        LDA  B,I
0629        JMP  DEBUG,I
0630  *
0631 .SCAN  NOP                 VARIABLE INITIALIZATION
0632        LDA  SCANO
0633        STA  SQNXT
0634        STA  SQAVL
0635        CLA
0636        STA  BUSY1
0637        STA  YARDS
0638        STA  WDMAX
0639        STA  WFLAG
0640        STA  SFLAG
0641        STA  TFLAG
0642        STA  FISER
0643        LDA  =B1777
0644        STA  WDMIN
0645        CCA
0646        STA  WARP
0647        JMP  .SCAN,I
0648  *
0649 BUSY1  NOP                 MAPPING BUSY FLAG
0650 SCANO  DEF  *+1            SCAN QUEUE ADDRESS
0651        BSS  5000           ROOM FOR A LOT
0652 SQEND  DEF  *              SCAN QUEUE END
0653 SQNXT  DEF  SCANO+1        GET POINTER
0654 SQAVL  DEF  SCANO+1        PUT POINTER
0655 SQSAV  NOP                 ENTRY START
0656 SQVAL  NOP                 CURRENT VALUE
0657 SQYRD  NOP                 SCAN QUEUE YARDAGE
0658 SQERR  NOP                 QUEUE OVERFLOW FLAG
0659 FLAGS  NOP                 PREPROCESSOR FLAGS
0660 YARDS  NOP                 CURRENT YARDAGE ON EXIT
0661 WIDTH  NOP                 CURRENT FABRIC WIDTH
0662 WDMIN  OCT  1777           MINIMUM FABRIC WIDTH
0663 WDMAX  NOP                 MAXIMUM FABRIC WIDTH
0664 MAXDF  DEC  15             MAXIMUM DEFECTS/YARD
0665 WFLAG  NOP                 CURRENT WIDTH VIOLATION
0666 SFLAG  NOP                 CURRENT SHADE VIOLATION
0667 TFLAG  NOP                 CURRENT TAG VIOLATION
0668 FWORD  NOP                 TEMPORARY FLAG WORD
0669 FLGAD  NOP                 FLAG WORD ADDRESS
0670 GAD    NOP                 DEFECT ADDRESS
0671 GADNX  NOP                 NEXT DEFECT ADDRESS
0672 LAST   NOP                 FILL COORDINATE FOR LAST SQUARE
0673 WARP   DEC  -1             GREATEST WARP VALUE
0674 BX1    NOP                 WARP FOR SQUARE
0675 BY1    NOP                 FILL FOR SQUARE
0676 DX2    NOP                 DEFECT WARP
0677 DY1    NOP                 DEFECT FILL
0678 DY2    NOP                 DEFECT FILL
0679 PNSUM  NOP                 SQUARE POS/NEG SUM
0680 COUNT  NOP                 TEMPORARY COUNT
0681 #DFCT  NOP                 MAXIMUM # TO MAP
0682 SRVAL  OCT  100000
0683 INTA   NOP                 REGISTER SAVE AREA
0684 INTB   NOP
0685 INTEO  NOP
0686 SAVP   NOP
0687 SAVA   NOP
0688 SAVB   NOP
0689 SAVEO  NOP
0690 %LITE  NOP                 REENTRANT RETURN ADDRESS
0691 .LITE  NOP                 REENTRANT RETURN ADDRESS
0692 FISER  NOP                 MISSED DEVICE FLAG COUNT
```

```
0693  FIS    EQU 10B     PREPROCESSOR I/O SLOT
0694  A      EQU 0
0695  B      EQU 1
0696  .      EQU 32B     BASE PAGE CONSTANTS
0697         END
**** LIST END ****
```

TABLE 6

```
:LI,S,1,SGRAD

0001  ASMB,L,C
0002         HED FABRIC INSPECTION DEFECT GRADING
0003         NAM GRADR,7
0004         ENT GRADR,,GRAD
0005         ENT GRADQ,GQNXT
0006         ENT GQAVL,GQYRD
0007         ENT GQCNT,GQEND
0008         ENT HISTQ,HQNXT
0009         ENT HQAVL,HQYRD
0010         ENT HQCNT,HQEND
0011         EXT SYSOP,WHOFP
0012         ENT HQERR
0013  *
0014  *
0015  *
0016  *     CLASSIFIES AND GRADES DEFECTS ACCORDING TO
0017  *     USER SELECTED SCHEME. ALL EVENTS IN GRADE QUEUE
0018  *     WITHIN CURRENT YARD ARE MOVED TO HISTORY QUEUE.
0019  *     GRADE QUEUE IS CLEARED FOR EACH YARD GRADED.
0020  *     HISTORY QUEUE IS A CIRCULAR TYPE QUEUE.
0021  *
0022  *
0023  *
0024  *     HISTORY QUEUE FORMAT    ** FLAG WORD     **
0025  *                             ** YARDAGE       **
0026  *                             ** WARP DX1      **
0027  *                             ** WARP DX2      **
0028  *                             ** FILL DY1      **
0029  *                             ** FILL DY2      **
0030  *     (MINIMUM WIDTH)         ** CLASSIFICATION**
0031  *     (MAXIMUM WIDTH)         ** GRADE POINTS  **
0032  *
0033  *
0034  *
0035  *     DAVID GATES
0036  *
0037  *     (11/5/76)
0038  *
0039  GRADR NOP
0040         LDB GRADQ
0041         STB GQNXT
0042         CPB GQAVL
0043         JMP GRADR,I   NOTHING TO PROCESS
0044         CLA
0045         STA YPTS      POINTS/YARD
0046  GRADE  LDB GQNXT
0047         LDA B,I
0048         CPA .+0
0049         JMP IGNOR     SKIP PURGED ENTRY
0050         AND =B200
0051         SZA,RSS
0052         JMP PACK      SAVE EVENT
0053         ADB .+2
0054         LDA B,I
0055         STA DX1       WARP START
0056         INB
0057         LDA B,I
0058         STA DX2       WARP END
0059         INB
0060         LDA B,I
0061         STA DY1       FILL START
0062         INB
0063         LDA B,I
```

```
0064        STA DY2         FILL END
0065        INB
0066        LDA B,I
0067        STA *BOX        # SQUARE INCHES
0068        INB
0069        LDA B,I
0070        STA PNSUM       POS/NEG SUM
0071        LDA DX1
0072        CMA,INA
0073        ADA DX2
0074        STA WSIZE       WARP DIMENSION
0075        LDA DY1
0076        CMA,INA
0077        ADA DY2
0078        STA FSIZE       FILL DIMENSION
0079        CPA WSIZE
0080        JMP ISOLD       ISOLATED DEFECT
0081        CMA,INA
0082        ADA WSIZE
0083        SSA
0084        JMP FILL        FILL LARGER
0085        LDA FSIZE
0086        ADA NAROW
0087        SSA,RSS
0088        JMP WBRD
0089        LDA .+1         NARROW WARP
0090        JMP CLASS
0091 WBRD   LDA .+3         BROAD WARP
0092        JMP CLASS
0093 FILL   LDA WSIZE
0094        ADA NAROW
0095        SSA,RSS
0096        JMP FBRD
0097        LDA .+2         NARROW FILL
0098        JMP CLASS
0099 FBRD   LDA .+4         BROAD FILL
0100        JMP CLASS
0101 ISOLD  LDA .+5         ISOLATED
0102 CLASS  LDB GQNXT
0103        ADB .+6
0104        STA B,I         DEFECT CLASSIFICATION
0105        LDA SYSOP
0106        AND .+7
0107        CPA .+1
0108        RSS
0109        JMP G10
0110 G4     JSB G4PT        FOUR POINT GRADING SCHEME
0111        JMP IGNOR       MAXIMUM POINTS/YARD
0112        JMP PACK
0113 G10    CPA .+2
0114        RSS
0115        JMP G4          DEFAULT TO FOUR POINT
0116        JSB G10PT       TEN POINT GRADING SCHEME
0117        JMP IGNOR       MAXIMUM POINTS/YARD
0118        JMP PACK
0119 PACK   LDA GQNXT       MOVE TO HISTORY QUEUE
0120        LDB HQAVL
0121        MVW .+8
0122        STA GQNXT
0123        CPB HQEND
0124        LDB HISTQ
0125        CPB HQNXT
0126        RSS
0127        JMP HOOK
0128        ISZ HQERR       HISTORY QUEUE OVERFLOW
0129        JMP OFLOW
0130 HOOK   STB HQAVL
0131        ISZ HQCNT
0132 OFLOW  CPA GQAVL
0133        JMP GRADR,I
0134        JMP GRADE
0135 IGNOR  LDA GQNXT       IGNORE CURRENT ENTRY
0136        ADA .+8
0137        STA GQNXT
0138        CPA GQAVL
0139        JMP GRADR,I
```

```
0140          JMP GRADE
0141    ♦
0142  G4PT    NOP
0143          LDA G4MX      MAXIMUM OF FOUR POINTS/YARD
0144          ADA YDPTS     USING FOUR POINT GRADING
0145          SSA,RSS
0146          JMP G4PT,I    IGNORE DEFECT
0147          LDA WSIZE
0148          ADA G4P1
0149          SSA,RSS
0150          JMP TWO
0151          LDA FSIZE
0152          ADA G4P1
0153          SSA,RSS
0154          JMP TWO
0155          LDA .+1       ONE POINT
0156          JMP POINT     WARP AND FILL LE 3 INCHES
0157  TWO     LDA WSIZE
0158          ADA G4P2
0159          SSA,RSS
0160          JMP THREE
0161          LDA FSIZE
0162          ADA G4P2
0163          SSA,RSS
0164          JMP THREE
0165          LDA .+2       TWO POINTS
0166          JMP POINT     WARP AND FILL LE 6 INCHES
0167  THREE   LDA WSIZE
0168          ADA G4P3
0169          SSA,RSS
0170          JMP FOUR
0171          LDA FSIZE
0172          ADA G4P3
0173          SSA,RSS
0174          JMP FOUR
0175          LDA .+3       THREE POINTS
0176          JMP POINT     WARP AND FILL LE 9 INCHES
0177  FOUR    LDA .+4       FOUR POINTS
0178  POINT   LDB GONXT
0179          ADB .+7
0180          STA B,I       GRADE POINTS
0181          ADA YDPTS
0182          STA YDPTS     POINTS/YARD
0183          ISZ G4PT
0184          JMP G4PT,I
0185    ♦
0186  G10PT   NOP
0187          LDA G10MX     MAXIMUM OF TEN POINTS/YARD
0188          ADA YDPTS     USING TEN POINT GRADING
0189          SSA,RSS
0190          JMP G10PT,I   IGNOR DEFECT
0191          LDA WSIZE
0192          ADA G10P1
0193          SSA,RSS
0194          JMP P3
0195          LDA FSIZE
0196          ADA G10P1
0197          SSA,RSS
0198          JMP P3
0199          LDA .+1       ONE POINT
0200          JMP PNTS      WARP AND FILL LE 1 INCH
0201  P3      LDA WSIZE
0202          ADA G10P3
0203          SSA,RSS
0204          JMP P5
0205          LDA FSIZE
0206          ADA G10P3
0207          SSA,RSS
0208          JMP P5
0209          LDA .+3       THREE POINTS
0210          JMP PNTS      WARP AND FILL LE 5 INCHES
0211  P5      LDA WSIZE
0212          ADA G10P5
0213          SSA,RSS
0214          JMP P10
0215          CLB
```

```
0216            LDA WDOPS
0217            DIV =D10
0218            ARS
0219            CMA,INA
0220            ADA FSIZE
0221            SIA,RSS
0222            JMP P10
0223            LDA .+5          FIVE POINTS
0224            JMP PNTS         WARP LE 10 INCHES AND FILL LE 1/2 WIDTH
0225   P10      LDA .+10         TEN POINTS
0226   PNTS     LDB GCNT
0227            ADB .+2
0228            STA B,I          GRADE POINTS
0229            ADA YDPTS
0230            STA YDPTS        POINTS/YARD
0231            ISZ G10PT
0232            JMP G10PT,I
0233   *
0234   .GRAD    NOP              VARIABLE INITIALIZATION
0235            LDA GRADQ
0236            STA GQAVL
0237            CLA
0238            STA GQYRD
0239            STA GQCNT
0240            LDA HISTQ
0241            STA HQAVL
0242            STA HQNXT
0243            CLA
0244            STA HQYRD
0245            STA HQCNT
0246            JMP .GRAD,I
0247   *
0248   GRADQ    DEF *+1          GRADE QUEUE ADDRESS
0249            BSS 136          ROOM FOR 15 DEFECTS
0250   GQEND    DEF *            GRADE QUEUE END
0251   GQAVL    DEF GRADQ+1      PUT POINTER
0252   GQYRD    NOP              GRADE QUEUE YARDAGE
0253   GQCNT    NOP              GRADE QUEUE COUNT
0254   GQNXT    DEF GRADQ+1      GET POINTER
0255   HQERR    NOP              OVERFLOW FLAG
0256   HISTQ    DEF *+1          HISTORY QUEUE ADDRESS
0257            BSS 4000         ROOM FOR 500 ENTRIES
0258   HQEND    DEF *            HISTORY QUEUE END
0259   HQAVL    DEF HISTQ+1      HISTORY PUT POINTER
0260   HQNXT    DEF HISTQ+1      HISTORY GET POINTER
0261   HQYRD    NOP              CURRENT YARDAGE
0262   HQCNT    NOP              CURRENT COUNT
0263   YDPTS    NOP              # POINTS IN CURRENT YARD
0264   DX1      NOP              DEFECT WARP START
0265   DX2      NOP              DEFECT WARP END
0266   DY1      NOP              DEFECT FILL LEFT
0267   DY2      NOP              DEFECT FILL RIGHT
0268   #BOX     NOP              # SQUARE INCHES
0269   PNSUM    NOP              POS/NEG SUM
0270   WSIZE    NOP              WARP DIMENSION
0271   FSIZE    NOP              FILL DIMENSION
0272   *
0273   .        EQU 32B          BASE PAGE CONSTANTS
0274   #        EQU 44B          GRADING CONSTANTS
0275   NARROW   EQU #+1          NARROW DEFINITION
0276   G4MX     EQU #+2          4 POINT MAXIMUM
0277   G4P1     EQU #+3          ONE POINT BREAK
0278   G4P2     EQU #+4          TWO POINT BREAK
0279   G4P3     EQU #+5          THREE POINT BREAK
0280   G10MX    EQU #+6          10 POINT MAXIMUM
0281   G10P1    EQU #+7          ONE POINT BREAK
0282   G10P3    EQU #+8          THREE POINT BREAK
0283   G10P5    EQU #+9          FIVE POINT BREAK
0284   A        EQU 0
0285   B        EQU 1
0286            END
**** LIST END ****
```

TABLE 7

```
:LI,S,1,SLIST

0001   ASMB,L,C
0002          HED FABRIC INSPECTION PRINTER DRIVER
0003          NAM LISTR,7
0004          ENT LISTR,WRITE,BUSY2
0005          EXT HISTQ,HQAVL,HQNXT
0006          EXT HQEND,HQCNT,HQYRD
0007          ENT HEADR,WFLAG,OFLAG
0008          ENT DNWT,DNWP,DNFT
0009          ENT DNFP,DBWT,DBWP
0010          ENT DBFT,DBFP,DIT
0011          ENT DIP,DOT,DOP
0012          ENT Y100,YNWD,YNWP
0013          ENT YNFD,YNFP,YBWD
0014          ENT YBWP,YBFD,YBFP
0015          ENT YID,YIP,YOD
0016          ENT YSEAM,SNWD,SNWP
0017          ENT SNFD,SNFP,SBWD
0018          ENT SBWP,SBFD,SBFP
0019          ENT SID,SIP,SOD
0020          ENT QULTY,QDFT,QPTS
0021          ENT QAVE
0022          ENT WDMIN,WDMAX
0023          EXT BUSY1,FMTR
0024          ENT .LIST,BUG0
0025          EXT HSTAK,HSTNX
0026          EXT HSTAV
0027          ENT PRTER
0028   *
0029   *
0030   *
0031   *      ACCUMULATES AND PRINTS STATISTICS FROM
0032   *      HISTORY QUEUE. INITIATED BY MONITOR AND
0033   *      CONTINUOUS PRINTING IS DONE UNTIL QUEUE
0034   *      IS EMPTIED BY COMPLETION INTERRUPTS.
0035   *      CENTRONICS MODEL 588 VERSION
0036   *
0037   *
0038   *
0039   *      DAVID GATES
0040   *
0041   *      (11/5/76)
0042   *
0043   LISTR NOP            MONITOR INITIATION SECTION
0044         LDA BUSY2
0045         SZA
0046         JMP LISTR,I    ALREADY PROCESSING QUEUE
0047         LDA HQNXT
0048         CPA HQAVL
0049         JMP LISTR,I    HISTORY QUEUE EMPTY
0050         LDA =B177      CLEAR PRINT BUFFER WITH RUBOUT
0051         OTA PRT
0052         STC PRT,C      PRINT MODE REQUESTED
0053         JMP LISTR,I
0054   *
0055   *
0056   *      PROCESS PRINTER COMPLETION INTERRUPTS
0057   *
0058   *
0059   WRITE DEF *          INTERRUPT TRAP ADDRESS
0060         CLF 0
0061         STA SAVA
0062         STB SAVB       SAVE REGISTERS
0063         ERA,ALS
0064         SOC
0065         INA
0066         STA SAVEQ
0067         LDA WRITE
0068         STA SAVP
0069         LDA BUSY1
0070         SZA
0071         JMP KILL
0072         CLA,INA        START PRINTING
```

```
0073         STA BUSY2      SET BUSY STATUS
0074         LDA POSTN      POSITION PAPER FLAG SET?
0075         SZA,RSS        LINE OR FORM FEED?
0076         JMP NEWLN      YEP
0077         CPA .+1        RUBOUT NEEDED?
0078         RSS
0079         JMP CONTN      NO, PRINT LINE NEEDED
0080         LDA =B177
0081         OTA PRT        CLEAR I/F BUFFER
0082         STC PRT,C
0083         JMP RUB        RUBOUT DONE
0084 NEWLN   LDA LOUT       FORM FEED NEEDED?
0085         CPA =D63
0086         JMP FORM       YEP
0087         LDA HEADR      1ST REPORT LINE?
0088         CPA .+9
0089         JMP START      MUST BE 1ST LINE
0090         LDA .+10       MUST NEED LINE FEED
0091         JMP PAPER
0092 START   ADA .-1        SET TO NEXT LINE
0093         STA HEADR
0094 FORM    LDA =B14       FORM FEED CODE
0095         CLB
0096         STB LOUT       SET LINE COUNT
0097 PAPER   CLF 0
0098         OTA PRT
0099         STC PRT,C
0100         ISZ LOUT       BUMP LINE COUNT
0101 RUB     ISZ POSTN      SET POSITION FLAG
0102         JMP EXIT
0103 CONTN   STF 0          RESTORE INTERRUPTS
0104         LDA OFLAG
0105         SZA,RSS
0106         JMP WMESG
0107         STA HEADR      SET FOR NEW HEADER
0108         CLA
0109         STA OFLAG      QUALITY MESSAGE
0110         LDA Y100       GET YARDAGE MOVED
0111         CMA,INA
0112         ADA YARDS
0113         SZA,RSS        100 YARDS?
0114         LDA =D100      YEP
0115         STA COUNT
0116         LDA OPTS       CALCULATE POINTS/YARD
0117         CLE
0118         MPY =D10
0119         CLE
0120         DIV COUNT
0121         SSA            OVERFLOW?
0122         CLA            YEP
0123         STA OAVE
0124         ADA O1ST
0125         SSA,RSS        1ST
0126         INB
0127         ADA O2ND
0128         SSA,RSS        2ND
0129         INB            RAS
0130         STB QULTY
0131         LDA .+5
0132         LDB PRBUF
0133         JSB FMTR
0134         CLA
0135         STA ODFT
0136         STA OPTS
0137         STA OAVE
0138         JMP LIST
0139 WMESG   LDA WFLAG
0140         SZA,RSS
0141         JMP HMESG
0142         STA OFLAG      QUALITY NEXT PASS
0143         CLA
0144         STA WFLAG      WIDTH MESSAGE
0145         LDA .+6
0146         LDB PRBUF
0147         JSB FMTR
0148         JMP LIST
```

```
0149  HMESS  LDA HEADR
0150         SZA,RSS
0151         JMP NORML
0152         ADA .-1
0153         CPA .+6          PRODUCT REPORT LINES?
0154         RSS              YEP
0155         JMP GO
0156         LDB HSTNX        GET HEADER STACK POINTER
0157         CPB HSTAV        HEADER STACK EMPTY
0158         JMP KILL         YEP, CAN'T DO MORE
0159  GO     STA HEADR        HEADER MESSAGE #
0160         CPA .+6          BALE LINE?
0161         LDA =D11
0162         CPA .+5          LOOM LINE?
0163         LDA =D12
0164         CPA .+4          WIDTH LINE?
0165         LDA =D13
0166         CPA .+3          STYLE LINE?
0167         LDA =D14
0168         CPA .+2          BLANK LINE?
0169         JMP NEWLN
0170         CPA .+1          DEFECT LINE?
0171         LDA .+1
0172         CPA .            MAP LINE?
0173         LDA .+7
0174         LDB PRBUF
0175         JSB FMTR
0176         JMP LIST
0177  NORML  LDA YDFLG        100 YARD LINE?
0178         SZA
0179         JMP YD100        YEP
0180         LDA SMFLG        SEAM LINE?
0181         SZA
0182         JMP SEAM         YEP
0183         LDA HQNXT        SCAN HISTORY QUEUE
0184         CPA HQAVL
0185         RSS
0186         JMP EVENT
0187  KILL   CLF 0            HISTORY QUEUE EMPTY
0188         CLA
0189         STA BUSY2
0190         CLC PRT
0191         JMP EXIT
0192  EVENT  LDB HQNXT        GET EVENT INFO
0193         STB BUGO         SAVE ENTRY ADDRESS
0194         LDA B,I
0195         STA FLAGS
0196         INB
0197         LDA B,I
0198         STA YARDS
0199         STA HOYRD
0200         ADB .+5
0201         LDA B,I
0202         STA CLASS
0203         INB
0204         LDA B,I
0205         STA GPTS
0206         INB
0207         CPB HQEND
0208         LDB HISTQ
0209         STB HQNXT
0210         LDA HQCNT
0211         ADA .-1
0212         STA HQCNT
0213         LDA FLAGS
0214         RAL,RAL
0215         RAL,SLA
0216         JMP SMMES        OUTPUT SEAM LINES
0217         HLF
0218         SSA
0219         JMP YDMES        OUTPUT 100 YARD LINES
0220         JSB CLRDF        CLEAR DEFECT COUNTERS
0221         LDA FLAGS
0222         AND =B17000
0223         SZA,RSS
0224         JMP NORMD
```

```
0225        ALF,SLA      WIDTH,SHADE,BARRE,OP TAG
0226        LDB WMES
0227        RAL,SLA
0228        LDB SMES
0229        RAL,SLA
0230        LDB BMES
0231        RAL,SLA
0232        LDB TMES
0233        STB DOP
0234        LDA YARDS
0235        STA DOT
0236        ISZ YOD
0237        ISZ SOD
0238        JMP DMESG
0239  NORMD LDA FLAGS    CHECK FOR LEGALITY
0240        AND =B200
0241        SZA,RSS
0242        JMP NORML
0243        LDA CLASS    NORMAL FABRIC DEFECT
0244        ADA .-6
0245        SSA,RSS
0246        JMP NORML    BAD CLASSIFICATION
0247        LDA CLASS
0248        ADA DTYPE
0249        LDA A,I
0250        JMP A,I      PROCESS DEFECT CLASS
0251  DTYPE DEF *
0252        DEF NWARP
0253        DEF NFILL
0254        DEF BWARP
0255        DEF BFILL
0256        DEF ISOL
0257  NWARP LDA GPTS     NARROW WARP
0258        STA DNWP
0259        LDA YARDS
0260        STA DNWT
0261        ISZ YNWD
0262        LDA GPTS
0263        ADA YNWP
0264        STA YNWP
0265        ISZ SNWD
0266        LDA GPTS
0267        ADA SNWP
0268        STA SNWP
0269        JMP DLIST
0270  NFILL LDA GPTS     NARROW FILL
0271        STA DNFP
0272        LDA YARDS
0273        STA DNFT
0274        ISZ YNFD
0275        LDA GPTS
0276        ADA YNFP
0277        STA YNFP
0278        ISZ SNFD
0279        LDA GPTS
0280        ADA SNFP
0281        STA SNFP
0282        JMP DLIST
0283  BWARP LDA GPTS     BROAD WARP
0284        STA DBWP
0285        LDA YARDS
0286        STA DBWT
0287        ISZ YBWD
0288        LDA GPTS
0289        ADA YBWP
0290        STA YBWP
0291        ISZ SBWD
0292        LDA GPTS
0293        ADA SBWP
0294        STA SBWP
0295        JMP DLIST
0296  BFILL LDA GPTS     BROAD FILL
0297        STA DBFP
0298        LDA YARDS
0299        STA DBFT
0300        ISZ YBFD
```

```
0301           LDA GPTS
0302           ADA YBFP
0303           STA YBFP
0304           ISZ SBFD
0305           LDA GPTS
0306           ADA SBFP
0307           STA SBFP
0308           JMP DLIST
0309    ISOL   LDA GPTS         ISOLATED
0310           STA DIP
0311           LDA YARDS
0312           STA DIT
0313           ISZ YID
0314           LDA GPTS
0315           ADA YIP
0316           STA YIP
0317           ISZ SID
0318           LDA GPTS
0319           ADA SIP
0320           STA SIP
0321    DLIST  ISZ QDFT         QUALITY COUNTERS
0322           LDA GPTS
0323           ADA OPTS
0324           STA OPTS
0325    DMESG  LDA .+2          DEFECT MESSAGE
0326           LDB PRBUF
0327           JSB FMTR
0328           JMP LIST
0329    YDMES  CLA,INA          100 YARD LINE
0330           STA YDFLG        SET FOR NEXT LINE
0331           LDA .+8
0332           LDB PRBUF
0333           JSB FMTR
0334           JMP LIST
0335    YD100  LDA YARDS        100 YARD INCREMENT
0336           STA Y100
0337           LDA CLASS
0338           STA WDMIN
0339           LDA GPTS
0340           STA WDMAX
0341           LDA .+3
0342           LDB PRBUF
0343           JSB FMTR         100 YARD MESSAGE
0344           LDA .+3
0345           STA WFLAG        SET FOR WIDTH LINE
0346           JSB CLRYD        CLEAR COUNTERS
0347           JMP LIST
0348    SMMES  CLA,INA          SEAM LINE
0349           STA SMFLG        SET FOR NEXT LINE
0350           LDA .+9
0351           LDB PRBUF
0352           JSB FMTR
0353           JMP LIST
0354    SEAM   LDA YARDS        FABRIC SEAM FOUND
0355           STA YSEAM
0356           LDA CLASS
0357           STA WDMIN
0358           LDA GPTS
0359           STA WDMAX
0360           LDA .+8
0361           STA WFLAG        SET FOR WIDTH LINE
0362           LDA .+4
0363           LDB PRBUF
0364           JSB FMTR
0365           JSB CLRSM        CLEAR SEAM COUNTERS
0366           JSB CLRYD        CLEAR YARD COUNTERS
0367    LIST   LDA =D-40        SUPPRESS BLANK CHAR. PRINTING
0368           STA COUNT
0369           LDB PRBUF        FORM BUFFER END ADDRESS
0370           ADB =D40
0371    SERCH  ADB .-1          DECREMENT ADDRESS
0372           LDA B,1          SET WORD TO PRINT
0373           CPA =B20040      BLANKS?
0374           RSS
0375           JMP DONE         NO, FOUND LAST WORD
0376           ISZ COUNT
```

```
0377            JMP SERCH
0378            LDA .-1             DEFAULT TO ONE WORD
0379            STB COUNT
0380   DONE     JSB PRINT           OUTPUT ONE LINE AND CR
0381   EXIT     LDA SAVEO           RESTORE REGISTERS
0382            ELA,ERA
0383            CLO
0384            SLA
0385            STF 1
0386            LDA SAVA
0387            LDB SAVB
0388            STF 0
0389            JMP SAVP,I
0390   *
0391   PRINT    NOP                 PRINTS AN ASCII LINE
0392            LDA PRBUF
0393            STA BUFAD
0394            LIA PRT             GET PRINTER STATUS
0395            SSA                 READY?
0396            JMP PDOWN           NOP
0397            CLF 0               INT. OFF
0398   CHARS    LDA BUFAD,I         GET CHARACTER PAIR
0399            ALF,ALF             LEFT CHARACTER
0400            AND =B377
0401            LDB A               VALID CHARACTER?
0402            ADA =B40
0403            AND =B100
0404            SZA,RSS
0405            LDB =B100           NO, DEFAULT TO ?
0406            SFS PRT
0407            JMP PDOWN           PRINTER NOT READY
0408            OTB PRT
0409            STC PRT,C
0410            LDA BUFAD,I         RIGHT CHARACTER
0411            AND =B277
0412            LDB A               VALID CHARACTER?
0413            ADA =B40
0414            AND =B100
0415            SZA,RSS
0416            LDB =B100           NO, DEFAULT TO ?
0417            SFS PRT
0418            JMP PDOWN           PRINTER NOT READY
0419            OTB PRT
0420            STC PRT,C
0421            ISZ BUFAD
0422            ISZ COUNT
0423            JMP CHARS
0424            LDA =B15            CARRIAGE RETURN
0425            OTA PRT
0426            STC PRT,C
0427            CLA                 SET POSITION PAPER FLAG
0428            STA POSTN
0429            JMP PRINT,I
0430   *
0431   PDOWN    ISZ PRTER           BUMP PRINTER ERROR FLAG
0432            JMP KILL
0433            JMP KILL
0434   *
0435   CLRDF    NOP                 CLEAR DEFECT COUNTERS
0436            CLA
0437            STA DNWT
0438            STA DNWP
0439            STA DNFT
0440            STA DNFP
0441            STA DBWT
0442            STA DBWP
0443            STA DBFT
0444            STA DBFP
0445            STA DIT
0446            STA DIP
0447            STA DOT
0448            LDA =B20040
0449            STA DOP
0450            JMP CLRDF,I
```

```
0451    *
0452    CLRYD   NOP             CLEAR 100 YARD COUNTERS
0453            CLA
0454            STA  YNWD
0455            STA  YNWP
0456            STA  YNFD
0457            STA  YNFP
0458            STA  YBWD
0459            STA  YBWP
0460            STA  YBFD
0461            STA  YBFP
0462            STA  YID
0463            STA  YIP
0464            STA  YDP
0465            STA  YDFLG
0466            JMP  CLRYD,I
0467    *
0468    CLRSM   NOP             CLEAR SEAM COUNTERS
0469            CLA
0470            STA  Y100
0471            STA  YSEAM
0472            STA  SNWD
0473            STA  SNWP
0474            STA  SNFD
0475            STA  SNFP
0476            STA  SBWD
0477            STA  SBWP
0478            STA  SBFD
0479            STA  SBFP
0480            STA  SID
0481            STA  SIP
0482            STA  SDP
0483            STA  SMFLG
0484            JMP  CLRSM,I
0485    *
0486    .LIST   NOP             VARIABLE INITIALIZATION
0487            CLA
0488            STA  BUSY2
0489            STA  QFLAG
0490            STA  WFLAG
0491            STA  POSTN
0492            STA  COUT
0493            STA  PRTER
0494            LDA  .+3
0495            STA  HEADR
0496            LDA  HSTAP       RESET REPORT HEADER STACK
0497            STA  HSTNC
0498            STA  HSTAV
0499            JSB  CLRDF
0500            JSB  CLRYD
0501            JSB  CLRSM
0502            JMP  .LIST,I
0503    *
0504    SAVA    NOP             REGISTER SAVE AREA
0505    SAVB    NOP
0506    SAVP    NOP
0507    SAVED   NOP
0508    PRBUF   DEF  *+1         BUFFER ADDRESS
0509            BSS  40          ROOM FOR 80 CHARACTERS
0510    BUFAD   NOP             BUFFER POINTER
0511    COUNT   NOP             BUFFER COUNTER
0512    BUSY2   NOP             DRIVER BUSY FLAG
0513    YDFLG   NOP             100 YARD FLAG
0514    SMFLG   NOP             SEAM LINE FLAG
0515    QFLAG   NOP             QUALITY MESSAGE FLAG
0516    WFLAG   NOP             WIDTH MESSAGE FLAG
0517    HEADR   NOP             HEADER MESSAGE FLAG
0518    FLAGS   NOP             DEFECT FLAG WORD
0519    YARDG   NOP             DEFECT YARDAGE
0520    CLASS   NOP             DEFECT CLASS
0521    GPTS    NOP             DEFECT GRADE POINTS
0522    WMES    ASC  1, W
0523    SMES    ASC  1, S
0524    BMES    ASC  1, B
0525    TMES    ASC  1, T
0526    DNWT    NOP             DEFECT COUNTERS
```

```
0527  DNWP   NOP
0528  DNFT   NOP
0529  DNFP   NOP
0530  DBWT   NOP
0531  DBWP   NOP
0532  DBFT   NOP
0533  DBFP   NOP
0534  DIT    NOP
0535  DIP    NOP
0536  DOT    NOP
0537  DOP    NOP
0538  Y100   NOP          100 YARD COUNTERS
0539  YNWD   NOP
0540  YNWP   NOP
0541  YNFD   NOP
0542  YNFP   NOP
0543  YBWD   NOP
0544  YBWP   NOP
0545  YBFD   NOP
0546  YBFP   NOP
0547  YID    NOP
0548  YIP    NOP
0549  YOD    NOP
0550  YSEAM  NOP          SEAM COUNTERS
0551  SNWD   NOP
0552  SNWP   NOP
0553  SNFD   NOP
0554  SNFP   NOP
0555  SBWD   NOP
0556  SBWP   NOP
0557  SBFD   NOP
0558  SBFP   NOP
0559  SID    NOP
0560  SIP    NOP
0561  SOD    NOP
0562  QULTY  NOP          QUALITY COUNTERS
0563  QDFT   NOP
0564  QPTS   NOP
0565  QAVE   NOP
0566  WDMIN  NOP          WIDTH COUNTERS
0567  WDMAX  NOP
0568  BUGQ   NOP          DEBUG HISTORY QUEUE ADDRESS
0569  POSTN  NOP          PAPER POSITION FLAG
0570  LOUT   NOP          CURRENT LINE COUNT
0571  PRTER  NOP          MISSED DEVICE FLAG COUNT
0572  PRT    EQU  11B     PRINTER I/O SLOT
0573  .      EQU  32B     BASE PAGE CONSTANTS
0574  A      EQU  0
0575  B      EQU  1
0576  Q1ST   EQU  102B
0577  Q2ND   EQU  103B
0578         END
**** LIST END ****
```

TABLE 8

```
:LI,S,1,SFMTR

0001  ASMB,L,C
0002       HED FABRIC INSPECTION MESSAGE FORMATER
0003       NAM FMTR,7
0004       ENT FMTR,DIGIT
0005       EXT DNWT,DNWP,DNFT
0006       EXT DNFP,DBWT,DBWP
0007       EXT DBFT,DBFP,DIT
0008       EXT DIP,DOT,DOP
0009       EXT Y100,YNWD,YNWP
0010       EXT YNFD,YNFP,YBWD
0011       EXT YBWP,YBFD,YBFP
0012       EXT YID,YIP,YOD
0013       EXT YSEAM,SNWD,SNWP
0014       EXT SNFD,SNFP,SBWD
```

```
0015            EXT SBWP,SBFD,SBFP
0016            EXT SID,SIP,SOD
0017            EXT QULTY,QDFT,QPTS
0018            EXT QAVE
0019            EXT WDMIN,WDMAX
0020            EXT HSTAK,HSTNX
0021            EXT HSTEN,BUGQ
0022    *
0023    *
0024    *
0025    *       CONVERTS FABRIC INSPECTION SYSTEM MESAGES
0026    *       FROM BINARY VALUES TO AN ASCII CHARACTER
0027    *       STRING GIVEN BUFFER ADDRESS AND FORMAT #.
0028    *
0029    *
0030    *
0031    *       DAVID GATES
0032    *
0033    *       (10/12/76)
0034    *
0035  FMTR  NOP
0036        STA TYPE        SAVE FORMAT NUMBER
0037        STB BUFAD       SAVE BUFFER ADDRESS
0038        ADA FMTS
0039        LDA A,I
0040        JMP A,I         PROCESS FORMAT CONVERSION
0041  FMTS  DEF *
0042        DEF HEADR       TYPE 1 - HEADER MESSAGE
0043        DEF DEFCT       TYPE 2 - DEFECT CALCULATION
0044        DEF YD100       TYPE 3 - 100 YARD CALCULATION
0045        DEF SEAMS       TYPE 4 - SEAM CALCULATION
0046        DEF QUAL        TYPE 5 - QUALITY CALCULATION
0047        DEF WIDTH       TYPE 6 - MIN/MAX WIDTH CALCULATION
0048        DEF MES1        TYPE 7 - MAP MESSAGE
0049        DEF MES2        TYPE 8 - 100 YARD MESSAGE
0050        DEF MES3        TYPE 9 - SEAM MESSAGE
0051        DEF MES4        TYPE 10- BLANK LINE MESSAGE
0052        DEF BALE        TYPE 11- BALE REPORT LINE
0053        DEF LOOM        TYPE 12- LOOM REPORT LINE
0054        DEF FABRC       TYPE 13- WIDTH REPORT LINE
0055        DEF STYLE       TYPE 14- STYLE REPORT LINE
0056  HEADR LDA FMT1        DEFECT HEADER MESSAGE
0057        JMP STORE
0058  DEFCT LIA 1           READ SWITCH REGISTER
0059        RAR
0060        SLA,RSS         DEBUG DUMP OF HISTORY QUEUE?
0061        JMP NORM        NO, NORMAL DEFECT REPORT
0062        LDA FMT0
0063        INA
0064        STA BUGAD       DEBUG BUFFER ADDRESS
0065        LDA .-8
0066        STA BUG#
0067  DUMP  CLA,INA         DUMP HISTORY QUEUE
0068        STA FORCE
0069        LDA BUGQ        GET VALUE ADDRESS
0070        LDA A,I         GET VALUE FROM QUEUE
0071        LDB BUGAD
0072        CCE
0073        JSB DIGIT
0074        LDB BUGAD
0075        ADB .+5
0076        STB BUGAD
0077        ISZ BUGQ
0078        ISZ BUG#
0079        JMP DUMP
0080        LDA FMT0        PRINT DEBUG LINE
0081        JMP STORE
0082  NORM  LDA DMIN
0083        LDB .DMIN
0084        ADB .+3
0085        CCE
0086        JSB DIGIT
0087        LDA .DMIN
0088        ADA DOFF
0089        LDB DMIN
0090        JSB DASH#
```

```
0091        LDA DNWT
0092        LDB .DNW
0093        ADB .-1
0094        CLE
0095        JSB DIGIT
0096        LDA DNFP        NARROW FILL DEFECT
0097        LDB .DNF
0098        ADB .+3
0099        CCE
0100        JSB DIGIT
0101        LDA .DNF
0102        ADA DOFF
0103        LDB DNFP
0104        JSB DASHR
0105        LDA DNFT
0106        LDB .DNF
0107        ADB .-1
0108        CLE
0109        JSB DIGIT
0110        LDA DBWP        BROAD WARP DEFECT
0111        LDB .DBW
0112        ADB .+3
0113        CCE
0114        JSB DIGIT
0115        LDA .DBW
0116        ADA DOFF
0117        LDB DBWP
0118        JSB DASHR
0119        LDA DBWT
0120        LDB .DBW
0121        ADB .-1
0122        CLE
0123        JSB DIGIT
0124        LDA DBFP        BROAD FILL DEFECT
0125        LDB .DBF
0126        ADB .+3
0127        CCE
0128        JSB DIGIT
0129        LDA .DBF
0130        ADA DOFF
0131        LDB DBFP
0132        JSB DASHR
0133        LDA DBFT
0134        LDB .DBF
0135        ADB .-1
0136        CLE
0137        JSB DIGIT
0138        LDA DIP         ISOLATED DEFECT
0139        LDB .DI
0140        ADB .+3
0141        CCE
0142        JSB DIGIT
0143        LDA .DI
0144        ADA DOFF
0145        LDB DIP
0146        JSB DASHR
0147        LDA DIT
0148        LDB .DI
0149        ADB .-1
0150        CLE
0151        JSB DIGIT
0152        LDA DOP         SPECIAL DEFECT
0153        LDB .DO
0154        ADB .+3
0155        STA B,I
0156        ADB .-1
0157        CPA =B20040
0158        RSS
0159        LDA DASH
0160        STA B,I
0161        CLB
0162        CPA DASH
0163        INB
0164        STB FORCE
0165        LDA DOT
```

```
0166        LDB .DO
0167        ADB .-1
0168        CLE
0169        JSB DIGIT
0170        LDA FMT2        DEFECT MESSAGE
0171        JMP STORE
0172  YD100 LDA Y100
0173        LDB FMT5        100 YARD MESSAGE
0174        CCE
0175        JSB DIGIT
0176        LDA YNWP        NARROW WARP TOTALS
0177        LDB .YNW
0178        ADB .+3
0179        CCE
0180        JSB DIGIT
0181        LDA .YNW
0182        ADA DOFF
0183        LDB YNWD
0184        JSB DASHR
0185        LDA YNWD
0186        LDB .YNW
0187        ADB .-1
0188        CLE
0189        JSB DIGIT
0190        LDA YNFP        NARROW FILL TOTALS
0191        LDB .YNF
0192        ADB .+3
0193        CCE
0194        JSB DIGIT
0195        LDA .YNF
0196        ADA DOFF
0197        LDB YNFD
0198        JSB DASHR
0199        LDA YNFD
0200        LDB .YNF
0201        ADB .-1
0202        CLE
0203        JSB DIGIT
0204        LDA YBWP        BROAD WARP TOTALS
0205        LDB .YBW
0206        ADB .+3
0207        CCE
0208        JSB DIGIT
0209        LDA .YBW
0210        ADA DOFF
0211        LDB YBWD
0212        JSB DASHR
0213        LDA YBWD
0214        LDB .YBW
0215        ADB .-1
0216        CLE
0217        JSB DIGIT
0218        LDA YBFP        BROAD FILL TOTALS
0219        LDB .YBF
0220        ADB .+3
0221        CCE
0222        JSB DIGIT
0223        LDA .YBF
0224        ADA DOFF
0225        LDB YBFD
0226        JSB DASHR
0227        LDA YBFD
0228        LDB .YBF
0229        ADB .-1
0230        CLE
0231        JSB DIGIT
0232        LDA YIP         ISOLATED TOTALS
0233        LDB .YI
0234        ADB .+3
0235        CCE
0236        JSB DIGIT
0237        LDA .YI
0238        ADA DOFF
0239        LDB YID
0240        JSB DASHR
0241        LDA YID
```

```
0242        LDA  .YT
0243        ADB  .-1
0244        CLE
0245        JSB  DIGIT
0246        LDA  YOD          SPECIAL TOTALS
0247        LDB  .YO
0248        ADB  .-1
0249        CLE
0250        JSB  DIGIT
0251        LDA  FMT3         100 YARD MESSAGE
0252        JMP  STORE
0253  SEAMS LDA  YSEAM        SEAM MESSAGE
0254        LDB  FMT6
0255        CCE
0256        JSB  DIGIT
0257        LDA  SNWP         NARROW WARP TOTALS
0258        LDB  .SNW
0259        ADB  .+3
0260        CCE
0261        JSB  DIGIT
0262        LDA  .SNW
0263        ADA  DOFF
0264        LDB  SNWD
0265        JSB  DASHP
0266        LDA  SNWD
0267        LDB  .SNW
0268        ADB  .-1
0269        CLE
0270        JSB  DIGIT
0271        LDA  SNFP         NARROW FILL TOTALS
0272        LDB  .SNF
0273        ADB  .+3
0274        CCE
0275        JSB  DIGIT
0276        LDA  .SNF
0277        ADA  DOFF
0278        LDB  SNFD
0279        JSB  DASHP
0280        LDA  SNFD
0281        LDB  .SNF
0282        ADB  .-1
0283        CLE
0284        JSB  DIGIT
0285        LDA  SBWP         BROAD WARP TOTALS
0286        LDB  .SBW
0287        ADB  .+3
0288        CCE
0289        JSB  DIGIT
0290        LDA  .SBW
0291        ADA  DOFF
0292        LDB  SBWD
0293        JSB  DASHP
0294        LDA  SBWD
0295        LDB  .SBW
0296        ADB  .-1
0297        CLE
0298        JSB  DIGIT
0299        LDA  SBFP         BROAD FILL TOTALS
0300        LDB  .SBF
0301        ADB  .+3
0302        CCE
0303        JSB  DIGIT
0304        LDA  .SBF
0305        ADA  DOFF
0306        LDB  SBFD
0307        JSB  DASHP
0308        LDA  SBFD
0309        LDB  .SBF
0310        ADB  .-1
0311        CLE
0312        JSB  DIGIT
0313        LDA  SIP          ISOLATED TOTALS
0314        LDB  .SI
0315        ADB  .+3
0316        CCE
0317        JSB  DIGIT
```

```
0318        LDA .51
0319        ADA DOFF
0320        LDB SID
0321        JSB DASH*
0322        LDA SID
0323        LDB .51
0324        ADB .-1
0325        CLE
0326        JSB DIGIT
0327        LDA SOD           SPECIAL TOTALS
0328        LDB .70
0329        ADB .-1
0330        CLE
0331        JSB DIGIT
0332        LDA FMT6          SEAM MESSAGE
0333        JMP STORE
0334 QUAL   LDA QULTY         QUALITY MESSAGE
0335        ADA .-1
0336        ALS
0337        ADA QMES
0338        LDB .QUAL
0339        MVW .+2
0340        CLA,INA
0341        STA FORCE
0342        CCE
0343        LDA QDFT
0344        LDB .QDFT
0345        JSB DIGIT
0346        CLA,INA
0347        STA FORCE
0348        LDA QPTS
0349        LDB .QPTS
0350        CCE
0351        JSB DIGIT
0352        CLA,INA
0353        STA FLOAT
0354        STA FORCE
0355        LDA QAVE
0356        LDB .QAVE
0357        CCE
0358        JSB DIGIT
0359        CLA
0360        STA FLOAT
0361        LDA FMT5
0362        JMP STORE
0363 WIDTH  CLA,INA           WIDTH MESSAGE
0364        STA FLOAT
0365        STA FORCE
0366        LDA WDMAX
0367        LDB .WDMX
0368        INB
0369        CCE
0370        JSB DIGIT
0371        CLA,INA
0372        STA FORCE
0373        CCE
0374        LDA WDMIN
0375        LDB .WDMN
0376        JSB DIGIT
0377        CLA
0378        STA FLOAT
0379        LDA FMT4
0380        JMP STORE
0381 MES1   LDA FMT7          MAP MESSAGE
0382        JMP STORE
0383 MES2   LDA FMT8          100 YARD MESSAGE
0384        JMP STORE
0385 MES3   LDA FMT9          SEAM MESSAGE
0386        JMP STORE
0387 MES4   LDA FMT10         BLANK LINE
0388        JMP STORE
0389 BALE   LDA HSTNX         BALE NUMBER
0390        LDA A,I
0391        LDB FMT11
0392        ADB .+6
0393        CCE
```

```
0394           JSB DIGIT
0395           LDA FMT11
0396           JMP STORE
0397  LOOM     LDA HSINX      LOOM NUMBER
0398           ADA ,+1
0399           LDA A,I
0400           LDB FMT12
0401           ADB ,+6
0402           CCE
0403           JSB DIGIT
0404           LDA FMT12
0405           JMP STORE
0406  FABRC    LDA HSINX      FABRIC WIDTH
0407           ADA ,+2
0408           LDA A,I
0409           CLB,INB
0410           JSB FLOAT
0411           CCE
0412           LDB FMT13
0413           ADB ,+6
0414           JSB DIGIT
0415           CLB
0416           STB FLOAT
0417           LDA FMT13
0418           JMP STORE
0419  STYLE    LDA HSINX      FABRIC STYLE
0420           ADA ,+3
0421           LDA FMT14
0422           ADB ,+6
0423           MVW ,+5
0424           CPA HSTEN      WRAP AROUND?
0425           LDA HSTAR,     YES
0426           STA HSINX      SET POINTER
0427           LDA FMT14
0428           JMP STORE
0429  STORE    LDB BUFAD      RETURN ASCII STRING
0430           MVW =D40
0431           JMP FMTR,I
0432  *
0433  DASH*    NOP            INSERT A DASH
0434           SZB
0435           JMP DSIGN
0436           LDB =B20040
0437           STB A,I
0438           JMP DASH*,I
0439  DSIGN    LDB DA*H
0440           STB A,I
0441           CLB,INB
0442           STA FORCE
0443           JMP DASH*,I
0444  *
0445  DIGIT    NOP            CONVERT BINARY TO ASCII
0446           STA VALUE      BINARY VALUE
0447           STB PAKAD      BUFFER ADDRESS
0448           ERA
0449           STA JUSTY
0450           LDA =B20040
0451           STA B,I        ZERO VALUE
0452           INB
0453           STA B,I
0454           INB
0455           STA B,I
0456           LDA FORCE
0457           CPA ,+0
0458           LDA VALUE
0459           SZA,RSS
0460           JMP DIGIT,I
0461           LDA VALUE
0462           LDB ZERO
0463           STB D0
0464           CLB
0465           DIV =D10000
0466           LDB ZERO
0467           ADB A
0468           STB D1         TEN THOUSANDS
0469           CLB
```

```
0470        MPY =D10000
0471        CMA,INA
0472        ADA VALUE
0473        STA VALUE
0474        CLB
0475        DIV =D1000
0476        LDB ZERO
0477        ADB A
0478        STB D2          THOUSANDS
0479        CLB
0480        MPY =D1000
0481        CMA,INA
0482        ADA VALUE
0483        STA VALUE
0484        CLB
0485        DIV =D100
0486        LDB ZERO
0487        ADB A
0488        STB D3          HUNDREDS
0489        CLB
0490        MPY =D100
0491        CMA,INA
0492        ADA VALUE
0493        STA VALUE
0494        CLB
0495        DIV =D10
0496        LDB ZERO
0497        ADB A
0498        STB D4          TENS
0499        CLB
0500        MPY =D10
0501        CMA,INA
0502        ADA VALUE
0503        LDB ZERO
0504        ADB A
0505        STB D5          ONES
0506        LDA .-5
0507        STA COUNT
0508        LDB DIGAD
0509 LEADZ  LDA B,I
0510        CPA ZERO
0511        RSS
0512        JMP INIT
0513        LDA BLANK
0514        STA B,I
0515        INB
0516        ISZ COUNT
0517        JMP LEADZ
0518 INIT   LDA .-3
0519        STA COUNT
0520        LDA FLOAT
0521        SZA,RSS
0522        JMP INTGR
0523        LDA DIGAD
0524        INA
0525        LDB DIGAD
0526        MWD .+4
0527        LDA =R56
0528        STA D4
0529 INTGR  LDB DIGAD
0530        LDA JUSTY
0531        ELA
0532 PACK   LDA B,I
0533        ALF,ALF
0534        INB
0535        IOR B,I
0536        STA PAKAD,I
0537        INB
0538        SEZ,RSS
0539        JMP PJUST
0540        CPA =R20040
0541        RSS
0542 PJUST  ISZ PAKAD
0543        ISZ COUNT
0544        JMP PACK
```

```
0545            CLA
0546            STA  FO4CE
0547            JMP  DIGIT.1
0548     *
0549     FMT0   DEF  *+1
0550            ASC  5,F
0551            ASC  5,S
0552            ASC  5,W
0553            ASC  5,W
0554            ASC  5,F
0555            ASC  5,F
0556            ASC  5,C
0557            ASC  5,P
0558     FMT1   DEF  *+1
0559            ASC  6,DEFECT
0560            ASC  6,NAR-WARP
0561            ASC  6,NAR-FILL
0562            ASC  6,WID-WARP
0563            ASC  6,WID-FILL
0564            ASC  6,ISOLATED
0565            ASC  4,SPECIAL
0566     FMT2   DEF  *+1
0567            ASC  20,
0568            ASC  20,
0569     FMT3   DEF  *+1
0570            ASC  20,
0571            ASC  20,
0572     FMT4   DEF  *+1
0573            ASC  10,WIDTH
0574            ASC  10,MINIMUM
0575            ASC  10,MAXIMUM
0576            ASC  10,
0577     FMT5   DEF  *+1
0578            ASC  10,   QUALITY
0579            ASC  10,DEFECTS
0580            ASC  10,POINTS
0581            ASC  10,AVE PTS
0582     FMT6   DEF  *+1
0583            ASC  20,
0584            ASC  20,
0585     FMT7   DEF  *+1
0586            ASC  6,   MAP
0587            ASC  6,YRD-PTS
0588            ASC  6,YRD-PTS
0589            ASC  6,YRD-PTS
0590            ASC  6,YRD-PTS
0591            ASC  6,YRD-PTS
0592            ASC  4,YRD-TYPE
0593     FMT8   DEF  *+1
0594            ASC  6,YARD
0595            ASC  6,QTY-PTS
0596            ASC  6,QTY-PTS
0597            ASC  6,QTY-PTS
0598            ASC  6,QTY-PTS
0599            ASC  6,QTY-PTS
0600            ASC  4,QTY
0601     FMT9   DEF  *+1
0602            ASC  6,SEAM
0603            ASC  6,QTY-PTS
0604            ASC  6,QTY-PTS
0605            ASC  6,QTY-PTS
0606            ASC  6,QTY-PTS
0607            ASC  6,QTY-PTS
0608            ASC  4,QTY
0609     FMT10  DEF  *+1
0610            ASC  20,
0611            ASC  20,
0612     FMT11  DEF  *+1
0613            ASC  20,PALE
0614            ASC  20,
0615     FMT12  DEF  *+1
0616            ASC  20,LOOM
0617            ASC  20,
0618     FMT13  DEF  *+1
0619            ASC  20,WIDTH
0620            ASC  20,
```

```
0621  FMT14  DEF  *+1
0622         ASC  20,STYLE
0623         ASC  20,
0624  .DMW   DEF  FMT2+6      DEFECT CALCULATION ADDRESSES
0625  .DMF   DEF  FMT2+12
0626  .DBW   DEF  FMT2+18
0627  .DBF   DEF  FMT2+24
0628  .DI    DEF  FMT2+30
0629  .DO    DEF  FMT2+36
0630  .YMW   DEF  FMT3+6      100 YARD CALCULATION ADDRESSES
0631  .YMF   DEF  FMT3+12
0632  .YBW   DEF  FMT3+18
0633  .YBF   DEF  FMT3+24
0634  .YI    DEF  FMT3+30
0635  .YO    DEF  FMT3+36
0636  .SMW   DEF  FMT6+6      SEAM CALCULATION ADDRESSES
0637  .SMF   DEF  FMT6+12
0638  .SBW   DEF  FMT6+18
0639  .SBF   DEF  FMT6+24
0640  .SI    DEF  FMT6+30
0641  .SO    DEF  FMT6+36
0642  .WDMN  DEF  FMT4+16     WIDTH CALCULATION ADDRESSES
0643  .WDMX  DEF  FMT4+25
0644  .QUAL  DEF  FMT5+1      QUALITY CONVERSION ADDRESSES
0645  .QDFT  DEF  FMT5+16
0646  .QPTS  DEF  FMT5+25
0647  .QAVE  DEF  FMT5+35
0648  *
0649  TYPE   NOP              FORMAT TYPE NUMBER
0650  BUFAD  NOP              USER BUFFER ADDRESS
0651  VALUE  NOP              BINARY NUMBER TO CONVERT
0652  COUNT  NOP              TEMPORARY COUNTER
0653  PAKAD  NOP              CONVERSION PACKED ADDRESS
0654  FLOAT  NOP              FLOATING POINT FLAG
0655  FORCE  NOP              FORCE ZERO DIGIT
0656  JUSTY  NOP              LEFT/RIGHT JUSTIFY
0657  ZERO   OCT  60          ASCII ZERO
0658  BLANK  OCT  40          ASCII BLANK
0659  QMES   DEF  *+1         QUALITY MESSAGE ADDRESS
0660         ASC  2,1ST
0661         ASC  2,2ND
0662         ASC  2,RAG
0663  DIGAD  DEF  *+1         DIGIT TABLE ADDRESS
0664  D0     OCT  60
0665  D1     NOP
0666  D2     NOP
0667  D3     NOP
0668  D4     NOP
0669  D5     NOP
0670  DOFF   DEC  2
0671  DASH   ASC  1, -
0672  BUGAD  NOP              DEBUG POINTER
0673  BUG#   NOP              DEBUG COUNTER
0674  .      EQU  32B         BASE PAGE CONSTANTS
0675  A      EQU  0
0676  B      EQU  1
0677         END
**** LIST END ****
```

Whereas, the present invention has been described with respect to specific embodiments thereof, it will be understood that various changes and modifications will be suggested to one skilled in the art, and it is intended to encompass such changes and modifications as fall within the scope of the appended claims.

What is claimed is:

1. An optical inspection system for detecting imperfections in a web of fabric having a longitudinal axis perpendicular to the width of the web and moving in a plane across an inspection area comprising:

a housing disposed above the plane of the web;

radiation means disposed in said housing above the plane of the web and transverse to the longitudinal axis of the web for directing radiant energy in the form of visible light to impinge on and across the entire width of the web at the inspection area to simulate visual inspection by a human operator;

a plurality of sensor means positioned within said housing and spaced from said radiation means and transverse to the longitudinal axis of the web for receiving reflected radiation from successive transverse portions of the entire width of the web passing across the inspection area, each of said sensor means being responsive to different discrete segments of a successive transverse portion of the web, said plurality of sensor means generating electrical output signals representing the intensity of the reflected radiation from said plurality of discrete segments;

means for scanning said electrical output signals from said plurality of sensor means corresponding to successive transverse portions of the entire width of the web;

means for storing selected ones of said scanned electrical output signals from selected ones of a plurality of said successive transverse portions of the web, such that said plurality of scanned successive transverse portions of the web defines a scanned area of a predetermined length in the direction parallel to the longitudinal axis of the web and having a length in the direction of the width of the web;

means for periodically summing said stored scanned electrical output signals from said scanned area to generate a summation signal representative of the sum of reflected radiation from said selected ones of said discrete segments within said selected ones of said plurality of successive transverse portions of the web contained within said scanned area;

means for extracting at least one of said electrical output signals corresponding to one of said discrete segments contained within said scanned area of the web from said means for storing electrical output signals; and means for comparing said extracted electrical output signal with said summation signal for generating a defect signal indicative of whether an imperfection exists within a discrete segment contained within said scanned area of the web and within one of said selected ones of said plurality of successive transverse portions of the web contained within said scanned area.

2. The inspection system of claim 1 wherein said means for generating a defect signal is operative in response to said means for comparing when the value of said electrical output signal is less than the value of said summation signal.

3. The inspection system of claim 1 wherein said means for generating a defect signal is operative in response to said means for comparing when the value of said electrical output signal is greater than the value of said summation signal.

4. The inspection system of claim 1 and further including:

means for adding a predetermined value to said extracted electrical output signal for generating a test signal; and means for comparing said test signal with said summation signal for generating a defect signal for determining whether an inperfection exists within a discrete segment of one of said successive transverse portions of the web.

5. A method of detecting imperfections in a web of moving fabric having a longitudinal axis perpendicular to the width of the web and moving across an inspection area, wherein a selected discrete portion contained within a scanned area of the web is tested for the presence of a defect by comparing reflection from the selected discrete portion to reflection from a matrix of discrete portions surrounding the selected discrete portion within the scanned area of the web comprising:

subjecting a plurality of successive transverse portions of the entire width of the web to a source of visible light to impinge on and across the entire width of the web within the scanned area to simulate visual inspection by a human operator;

detecting reflected radiation from selected ones of said plurality of successive transverse portions of the entire width of the scanned area within the moving web passing across the inspection area;

generating electrical output signals representing the intensity of the reflected radiation from said selected discrete portion and from said matrix of discrete portions contained within the scanned area;

summing said electrical output signals representative of reflection from said matrix to generate a summation signal representative of the sum of reflected radiation from selected ones of said discrete segments within selected ones of a plurality of said successive transverse portions of the web within the scanned area of the web defined by a length in the direction of the width of the web and a length in the direction parallel to the longitudinal axis of the web;

comparing said electrical output signal corresponding to said selected discrete portion with the summation signal; and generating a defect signal indicative of whether an imperfection exists within the selected discrete portion of the scanned area of the web.

6. The method of claim 5 and further including:

generating a defect signal if the value of the electrical output signal of the selected discrete portion within the matrix is greater than the value of said summation signal.

7. The method of claim 5 and further including:

generating a defect signal if the value of the electrical output signal of the selected discrete portion within the matrix is less than the value of the summation signal.

8. The method of claim 5 and further including:

moving the location of the matrix parallel to the longitudinal axis of the web.

9. The method of claim 5 and further including:

moving the location of the matrix transverse to the longitudinal axis of the web.

* * * * *

UNITED STATES PATENT AND TRADEMARK OFFICE
CERTIFICATE OF CORRECTION

Page 1 of 2

PATENT NO. : 4,170,419
DATED : October 9, 1979
INVENTOR(S) : Richard G. Van Tyne et al It is certified that error appears in the above-identified patent and that said Letters Patent are hereby corrected as shown below:

Column 2, line 16, change "of" to --or--.

Column 2, line 19, after "simulate" insert --visual--.

Column 6, line 11, change "comuter" to --computer--.

Column 6, line 19, change "fbric" to --fabric--.

Column 11, line 30, change "bearing" to --bearings--.

Column 13, line 28, change "322" to --332--.

Column 15, line 20, change "of" to --or--.

Column 20, line 61 (2nd instance) change "cells" to --cell--.

Column 22, line 51, change "repeatedon" to --repeated on--.

Column 24, line 20, change "Location" to --Locations--.

Column 24, line 58, change "Location" to --Locations--.

Column 27, line 6, change "g-v" to --q-v--.

Column 34, line 15, change "(FIG. 13)" to --(FIG. 33)--.

Column 38, line 9, change "Th" to --The--.

Column 39, line 40, change "who" to --web--.

Column 40, line 47, change "7422" to --7442--.

UNITED STATES PATENT AND TRADEMARK OFFICE
CERTIFICATE OF CORRECTION

PATENT NO. : 4,170,419
DATED : October 9, 1979
INVENTOR(S) : Richard G. Van Tyne et al It is certified that error appears in the above-identified patent and that said Letters Patent are hereby corrected as shown below:

Column 43-44 (page 95, Table 1), entries shown under "WID-WARP" should be under "ISOLATED".

Column 137, line 52 (Claim [22] 4, line 8), change "inperfection" to --imperfection--.

Signed and Sealed this

Twelfth Day of February 1980

[SEAL]

Attest:

SIDNEY A. DIAMOND

Attesting Officer

Commissioner of Patents and Trademarks